US012322515B2

United States Patent
Crouch et al.

(10) Patent No.: US 12,322,515 B2
(45) Date of Patent: Jun. 3, 2025

(54) PERSONALIZED WELLNESS SYSTEMS AND METHODS OF USE

(71) Applicant: Onikoroshi, LLC, Boulder, CO (US)

(72) Inventors: James Crouch, Boulder, CO (US); Sean Callan, Denver, CO (US)

(73) Assignee: Onikoroshi, LLC, Boulder, CO (US)

( * ) Notice: Subject to any disclaimer, the term of this patent is extended or adjusted under 35 U.S.C. 154(b) by 0 days.

(21) Appl. No.: 18/353,737

(22) Filed: Jul. 17, 2023

(65) Prior Publication Data

US 2025/0022602 A1 Jan. 16, 2025

Related U.S. Application Data

(60) Provisional application No. 63/513,589, filed on Jul. 14, 2023.

(51) Int. Cl.
*G16H 50/30* (2018.01)
*G16B 20/00* (2019.01)
*G16B 40/00* (2019.01)
*G16H 10/40* (2018.01)
*G16H 10/60* (2018.01)
*G16H 20/00* (2018.01)

(52) U.S. Cl.
CPC ............. *G16H 50/30* (2018.01); *G16B 20/00* (2019.02); *G16B 40/00* (2019.02); *G16H 10/40* (2018.01); *G16H 10/60* (2018.01); *G16H 20/00* (2018.01)

(58) Field of Classification Search
CPC ........ G16H 50/30; G16H 10/40; G16H 10/60; G16H 20/00; G16B 40/00; G16B 20/00
See application file for complete search history.

(56) References Cited

U.S. PATENT DOCUMENTS

| | | |
|---|---|---|
| 6,287,254 B1 | 9/2001 | Dodds |
| 6,358,546 B1 | 3/2002 | Bebiak et al. |
| 6,493,641 B1 | 12/2002 | Singh et al. |
| 6,537,213 B2 | 3/2003 | Dodds |
| 6,730,023 B1 | 5/2004 | Dodds |
| 7,029,441 B2 | 4/2006 | Dodds |
| 7,134,995 B2 | 11/2006 | Dodds |
| 7,548,839 B2 | 6/2009 | Dodds |
| 7,552,039 B2 | 6/2009 | Dodds |
| 7,797,145 B2 | 9/2010 | Dodds |
| 7,865,343 B2 | 1/2011 | Dodds |
| 7,873,482 B2 | 1/2011 | Stefanon et al. |
| 7,970,552 B1 | 6/2011 | Stefanon et al. |
| 8,060,354 B2 | 11/2011 | Dodds |
| 8,234,099 B2 | 7/2012 | Dodds |
| 9,242,765 B2 | 1/2016 | Oziomek et al. |
| 9,420,809 B2 | 8/2016 | Donavon et al. |
| 10,468,141 B1 | 11/2019 | Valenzuela et al. |
| 11,501,851 B2 | 11/2022 | Sams et al. |
| 2002/0022772 A1 | 2/2002 | Dodds |
| 2003/0004655 A1 | 1/2003 | Singh et al. |
| 2004/0131658 A1 | 7/2004 | Kaput |
| 2005/0065736 A1 | 3/2005 | Bauck et al. |
| 2005/0090718 A1 | 4/2005 | Dodds |
| 2005/0158734 A1 | 7/2005 | Kaput |
| 2006/0045909 A1 | 3/2006 | Friesen et al. |
| 2006/0200320 A1 | 9/2006 | Al-Murrani |
| 2006/0235625 A1 | 10/2006 | Ostrander et al. |
| 2007/0118295 A1 | 5/2007 | Al-Murrani |
| 2010/0304396 A1 | 12/2010 | Dodds |
| 2011/0153221 A1 | 6/2011 | Stefanon et al. |
| 2011/0246405 A1 | 10/2011 | Dodds |
| 2012/0185175 A1 | 7/2012 | Dodds |
| 2012/0303286 A1* | 11/2012 | Dodds ..................... G16B 50/40 702/19 |
| 2012/0309639 A1* | 12/2012 | Hakonarson ........... G16B 40/20 702/19 |
| 2014/0141131 A1 | 5/2014 | Oziomek et al. |
| 2014/0141134 A1 | 5/2014 | Johnson et al. |
| 2014/0272028 A1 | 9/2014 | Donavon et al. |
| 2015/0072048 A1 | 3/2015 | Potthoff et al. |
| 2015/0242566 A1 | 8/2015 | Samer |
| 2015/0286774 A1 | 10/2015 | Lohi et al. |
| 2016/0364522 A1* | 12/2016 | Frey ....................... G16B 40/20 |
| 2017/0220734 A1* | 8/2017 | Colavin ................. G16B 40/20 |
| 2018/0328945 A1 | 11/2018 | Nova et al. |
| 2019/0295691 A1* | 9/2019 | Garshon ................ G16B 20/20 |
| 2021/0287758 A1 | 9/2021 | Wong et al. |
| 2023/0061512 A1 | 3/2023 | Sams et al. |

(Continued)

FOREIGN PATENT DOCUMENTS

| | | |
|---|---|---|
| EP | 4062411 A1 | 9/2022 |
| EP | 4127224 A1 | 2/2023 |
| WO | WO-2020109858 A1 | 6/2020 |

(Continued)

OTHER PUBLICATIONS

Gjuvsland et al. "Bridging the Genotype-Phenotype Gap: What does it Take?" J. Physiol (2013) vol. 591, No. 8, pp. 2055-2066 (Year: 2013).*
AAFCO, PFC Committee Report/Minutes AAFCO Annual Meeting Aug. 4, 2015; Denver, CO. (2015). Available at https://www.aafco.org/wp-content/uploads/2023/01/Pet_Food_Report_2015_Annual.pdf.
Ahner et al., Protein biomarkers in serum and urine for determining presence or absence of hip dysplasia in a canine model. J Orthop Res. 37(4):916-920 (2019).
Almela et al., Selected serum oxidative stress biomarkers in dogs with non-food-induced and food-induced atopic dermatitis. Vet Dermatol. 29(3):229-e82 (2018).

(Continued)

*Primary Examiner* — Jerry Lin
(74) *Attorney, Agent, or Firm* — Wilson Sonsini Goodrich & Rosati

(57) ABSTRACT

A health and wellness system for a non-human subject comprising analyzing genetic data and phenotypic data of the non-human subject with a machine learning algorithm and making a recommendation or recommendation for products or activities for the non-human subject.

30 Claims, 16 Drawing Sheets

(56) References Cited

U.S. PATENT DOCUMENTS

| | | | |
|---|---|---|---|
| 2023/0106107 A1* | 4/2023 | Boyko | G16B 20/20 702/20 |
| 2023/0157320 A1 | 5/2023 | Roche et al. | |

FOREIGN PATENT DOCUMENTS

| | | |
|---|---|---|
| WO | WO-2021101896 A1 | 5/2021 |
| WO | WO-2021202910 A1 | 10/2021 |
| WO | WO-2021207370 A1 | 10/2021 |

OTHER PUBLICATIONS

Asahina et al., Serum canine thymus and activation-regulated chemokine (TARC/CCL17) concentrations correlate with disease severity and therapeutic responses in dogs with atopic dermatitis. Vet Dermatol. 31(6):446-455 (2020).

Axelsson et al., The genomic signature of dog domestication reveals adaptation to a starch-rich diet. Nature. 495(7441):360-364 (2013).

Basepaws Veterinary, Basepaws canine baseline genetic tests. Basepaws Veterinary by Zoetis. (2022). Available at https://basepawsvet.com/canine-products.

Basepaws Veterinary, Basepaws feline genetic & oral microbiome tests. Basepaws Veterinary by Zoetis. (2022). Available at https://basepawsvet.com/feline-products.

Bergström et al., Origins and genetic legacy of prehistoric dogs. Science. 370(6516):557-564 (2020).

Biber Ingenity: 877-Igenity. Bieber Red Angus Ranch. (2018). Available at https://bieberredangus.com/igenity/.

Cardona-Ramírez et al., The differentiating ability of four plasma biomarkers in canine hip dysplasia. Vet Clin Pathol. 48(2):320-327 (2019).

Carlos et al., Canine metabolomics advances. Metabolomics. 16(2):16 (2020).

Chon et al., Genomic tumor analysis provides clinical guidance for the management of diagnostically challenging cancers in dogs. J Am Vet Med Assoc. 261(5):668-677 (2023).

Donner et al., Genetic prevalence and clinical relevance of canine Mendelian disease variants in over one million dogs. PLoS Genet. 19(2):e1010651 (2023).

Embark, Better care for your patients is in their DNA. (2022). Available at https://embarkvet.com/vets/.

Forcada et al., A genome-wide association study identifies novel candidate genes for susceptibility to diabetes mellitus in non-obese cats. PLoS One. 16(12):e0259939 (2021).

González-Arostegui et al., Changes in biomarkers of redox status in serum and saliva of dogs with hypothyroidism. BMC Vet Res. 9(1):33 (2023).

González-Arostegui et al., Changes in the salivary metabolome in canine hypothyroidism: A pilot study. Res Vet Sci. 151:189-195 (2022).

Heishima et al., Circulating microRNA-214 and -126 as potential biomarkers for canine neoplastic disease. Sci Rep. 7(1):2301 (2017).

Hokamp et al., Renal biomarkers in domestic species. Vet Clin Pathol. 45(1):28-56 (2016).

Iams, Iams™M Pet Food + Wisdom Panel™ DNA test for Cats & Dogs (2023). Available at https://www.iams.com/wisdom-panel.

Jones, Best dog DNA tests 2023: DNA My Dog vs Wisdom Panel vs Embark vs Orivet vs EasyDNA & More. Canine Journal. May 23, 2023.

Koury et al., Phosphodiesterase 4D, miR-203 and selected cytokines in the peripheral blood are associated with canine atopic dermatitis. PLoS One. 14(6):e0218670 (2019).

Lindblad-Toh et al., Genome sequence, comparative analysis and haplotype structure of the domestic dog. Nature. 438(7069):803-819 (2005).

Marsella, Advances in our understanding of canine atopic dermatitis. Vet Dermatol. 32(6):547-e151 (2021).

Martins et al., Clinical-pathological and immunological biomarkers in dogs with atopic dermatitis. Vet Immunol Immunopathol. 205:58-64 (2018).

Mazaki-Tovi et al., Increased serum leptin and insulin concentrations in canine hypothyroidism. Vet J. 183(1):109-114 (2010).

Meddens et al., Genomic analysis of diet composition finds novel loci and associations with health and lifestyle. Mol Psychiatry. 26(6):2056-2069 (2021).

Muñoz-Prieto et al., Untargeted metabolomic profiling of serum in dogs with hypothyroidism. Res Vet Sci. 136:6-10 (2021).

Neogen, Igenity® Beef: Item No. 44—Brochure and Technical Specification sheet. (2023). Available at https://www.neogen.com/categories/igenity-profiles/igenity-beef/?min=GS_SL_44.

Neogen, Igenity® Canine Wellness. (2020). Available at https://www.neogen.com/igenity-canine-wellness/.

O'Kell et a., Untargeted metabolomic analysis in naturally occurring canine diabetes mellitus identifies similarities to human Type 1 Diabetes. Sci Rep. 7(1):9467 (2017).

O'Kell et al., Untargeted metabolomic analysis in non-fasted diabetic dogs by UHPLC-HRMS. Metabolomics. 15(2):15 (2019).

Pallotti et al., Dog-human translational genomics: state of the art and genomic resources. J Appl Genet. 63(4):703-716 (2022).

Pet Business, Iams, Wisdom Panel Partner on Genetics-Based Nutrition. Pet Business Digital mag, 2pgs. May 2023. Available at https://digitalmag.petbusiness.com/petbusiness/library/item/may_2023/4102425/.

Petdx, Early Cancer Detection in Dogs with a Simple Blood Draw. (2023). Available at https://petdx.com/.

Piras et al., Identification of genetic susceptibility factors associated with canine gastric dilatation-volvulus. Genes (Basel). 11(11):1313 (2020).

Plassais et al., Analysis of large versus small dogs reveals three genes on the canine X chromosome associated with body weight, muscling and back fat thickness. PLoS Genet. 13(3):e1006661 (2017).

Royal Canin, Discover the secrets of your dog's DNA-Genetic Health Analysis. (2023) Available at https://www.royalcanin.com/us/dogs/genetic-health-analysis.

Ryad et al., Oxidative biomarkers and lipid alterations in euthyroid and hypothyroid dogs. Comp Clin Pathol. 30:571-576 (2021).

Santoro et al., Evaluation of cutaneous and circulating (serum and exosomes) levels of chemokines (CCL17, CCL22, CCL27 and CCL28) in atopic dogs and their correlation with severity of the disease. Vet Dermatol. 33(3):195-e56 (2022).

Vidium, SearchLight DNA™ for veterinarians. (2023). Available at https://vidiumah.com/searchlight-dna/.

Wang et al.; Genome-wide association studies for canine hip dysplasia in single and multiple populations—implications and potential novel risk loci. BMC Genomics. 22(1):636 (2021).

Williams et al., Body Condition Scores. VCA Animal Hospital. (2023). Available at https://vcahospitals.com/know-your-pet/body-condition-scores.

Winiarczyk et al., Proteomic analysis of tear film obtained from diabetic dogs. Animals. 10(12):2416 (2020).

Wisdompanel, Royal Canin® Genetic Health Analysis™: disease and mutation tests. Available at https://wisdompanel.my.salesforce-sites.com/royalcaningha/, (2021).

Wood et al., Genome-wide association analysis of canine atopic dermatitis and identification of disease related SNPs. Immunogenetics. 61(11-12):765-772 (2009).

Zelezniak et al., Machine learning predicts the yeast metabolome from the quantitative proteome of kinase knockouts. Cell Syst. 7(3):269-283.e6 (2018).

McConnel, Blair. For the Future of Pet Care Genomics, Look to Livestock. Linkedin. Available at https://www.linkedin.com/pulse/future-pet-care-genomics-look-livestock-blair-mcconnel-dukce/?trackingId=VAHXLpRfYpw327ytZEdBlg%3D%3D (published Jun. 21, 2024).

PCT/US2024/037714 International Search Report and Written Opinion dated Dec. 11, 2024.

* cited by examiner

PERSONALIZED WELLNESS SYSTEMS AND METHODS OF USE

RELATED APPLICATIONS

This application claims benefit of U.S. provisional patent application No. 63/513,589, filed on Jul. 14, 2023, which is incorporated herein by reference in its entirety.

SUMMARY

Provided herein are methods and systems for assessing one or more conditions in non-human subjects using machine learning. The machine learning models are applied to genetic data and phenotypic data to create a genotype-phenotype to identify the presence of one or more conditions in the non-human subject, or a risk of developing one or more conditions in the non-human subject. The genetic data may comprise data from a plurality of genomic loci, for example, genetic variants that are associated with one or more conditions. The phenotypic data may comprise data from a plurality of phenotypic factors that are associated with one or more conditions.

Aspects disclosed herein provide methods for identifying one or more conditions in a non-human subject, the method comprising: a method for identifying one or more conditions in a non-human subject, the method comprising: (a) receiving a data set comprising: (i) genetic data at a plurality of genomic loci of the non-human subject, wherein the plurality of genomic loci are associated with the one or more conditions; and (ii) phenotypic data pertaining to a plurality of phenotypes of the non-human subject; (b) producing a genotype-phenotype profile for the non-human subject by processing the data set to determine quantitative measures of at least one genomic locus of the plurality of genomic loci, and qualitative or quantitative measures of at least one phenotype of the plurality of phenotypes; and (c) applying a machine learning prediction model to the genotype-phenotype profile of the non-human subject to identify the non-human subject as having the one or more conditions or a risk of developing the one or more conditions. In some embodiments, the methods further comprise determining a wellness probability score (WPS) from the genotype-phenotype profile. In some embodiments, the WPS is a numerical value that is indicative of the likelihood that the non-human subject has the one or more conditions or a risk of developing the one or more conditions. In some embodiments, the method comprises identifying the non-human subject as having a plurality of the one or more conditions or the risk of developing the plurality of the one or more conditions. In some embodiments, the one or more conditions comprises one or more genetic conditions, one or more nutritional conditions, one or more clinical conditions, one or more fitness conditions, one or more dermatological conditions or one or more allergy conditions, or any combination thereof. In some embodiments, the non-human subject is a mammal. In some embodiments, the mammal is a feline, a canine, or a farm animal. In some embodiments, the mammal is a companion animal. In some embodiments, the companion animal is the feline or canine. In some embodiments, the genetic data is determined by: (a) obtaining or having obtained a biological sample from the non-human subject; and (b) performing or having performed a genotyping assay on the biological sample. In some embodiments, performing or having performed the genotyping assay comprises: (i) subjecting the biological sample to conditions that are sufficient to isolate, enrich, or extract a plurality of DNA molecules from the biological sample; and (ii) analyzing the plurality of DNA molecules to generate the genetic data. In some embodiments, the analyzing the plurality of DNA molecules comprises performing whole genome sequencing, skim sequencing, quantitative PCR (qPCR), or analysis using a DNA microarray. In some embodiments, the plurality of genomic loci comprises one or more polymorphisms. In some embodiments, the one or more polymorphisms comprises a single-nucleotide polymorphism (SNP) or an indel. In some embodiments, the plurality of genomic loci comprises at least 8 distinct loci. In some embodiments, the phenotypic data comprises information obtained from a guardian of the non-human subject, a veterinarian of the non-human subject, or a combination thereof. In some embodiments, receiving the phenotypic data from an application (App) or website populated by the guardian of the non-human subject or the veterinarian of the non-human subject. In some embodiments, the phenotypic data comprises physical attributes, clinical data, behavioral traits, or any combination thereof. In some embodiments, physical attributes comprises weight, sex, age, or breed. In some embodiments, the age is the biological age of the non-human subject as determined by measuring methylation of DNA in a biological sample obtained from the non-human subject. In some embodiments, clinical data comprises medical history or family medical history. In some embodiments, the medical history or the family medical history comprises diagnosis or prognosis of one or more diseases or one or more conditions, dietary sensitivities, lameness, allergies, activity level, exercise intolerance, reproductive status, pre-existing conditions, known adverse lifetime events, or any combination thereof. In some embodiments, the medical history or the family medical history comprises the diagnosis of the one or more diseases or the one or more conditions. In some embodiments, the medical history or the family medical history comprises the prognosis of the one or more diseases or the one or more conditions. In some embodiments, the one or more diseases or the one or more conditions is a dental disease or condition. In some embodiments, behavioral traits comprises chewing, itching, aggression, neurosis, anxiety, energy level, or any combination thereof. In some embodiments, the method further comprises receiving activity information of the non-human subject. In some embodiments, the activity information comprises activity level, activity type, calories burned, time asleep, or any combination thereof. In some embodiments, the activity data comprises information obtained from an activity tracking device. In some embodiments, the activity tracking device comprises a smart device. In some embodiments, the tracking device comprises a Global Positioning System (GPS)-connected dog collar. In some embodiments, the activity data comprises information obtained from a guardian of the non-human subject, a veterinarian of the non-human subject, or a combination thereof. In some embodiments, the activity data are input into an application (App) or website by the guardian of the non-human subject or the veterinarian of the non-human subject. In some embodiments, the method further comprises receiving environmental data of the non-human subject. In some embodiments, the environmental data comprise a city environment, a rural environment, geographic location of residence, presence of allergens, time spent inside/outside, frequency of stair use, or any combination thereof. In some embodiments, the environmental data comprises information obtained from a guardian of the non-human subject, a veterinarian of the non-human subject, or a combination thereof. In some embodiments, the environmental data are input into an App or website by the guardian of the non-human subject or the veterinarian of the non-human subject. In some embodiments, the method further comprises receiving biomarker data for the non-human subject, wherein the biomarker data is obtained by assaying a biological sample from the non-human subject under conditions sufficient to detect an amount or a presence of one or more biomarkers, wherein the one or more biomarkers is associated with the one or more conditions. In some embodiments, the one or more biomarkers comprises a protein, sugar, lipid, hormone, vitamin, cell, metabolite, electrolyte, or any combination thereof. In some embodiments, the protein is an enzyme. In some embodiments, the enzyme is a digestive enzyme or a metabolic enzyme. In some embodiments, the digestive enzyme is lipase or an amylase. In some embodiments, the metabolic enzyme is a lactate dehydrogenase, a creatine phosphokinase, a gamma-glutamyl transpeptidase, a serum glutamate pyruvate transaminase, or an alkaline phosphatase. In some embodiments, the protein comprises total protein. In some embodiments, the protein is albumin, globulin, or a lipoprotein. In some embodiments, the lipoprotein is a low-density lipoprotein or a high-density lipoprotein. In some embodiments, the sugar comprises glucose. In some embodiments, the lipid comprises fatty acid. In some embodiments, the lipid comprises sterol. In some embodiments, the sterol is a cholesterol. In some embodiments, the hormone is cortisol or a thyroid hormone. In some embodiments, the thyroid hormone is triiodothyronine or thyroxine. In some embodiments, the vitamin comprises a fat-soluble vitamin or a water-soluble vitamin. In some embodiments, the cell comprises a red blood cell, a white blood cell, a platelet, or any combination thereof. In some embodiments, the metabolite is urea nitrogen, total bilirubin, or creatinine. In some embodiments, the electrolyte comprises sodium, potassium, chloride, calcium, phosphorus, or any combination thereof. In some embodiments, the biological sample comprises a tissue biopsy, peripheral blood, capillary blood, a stool sample, a urine sample, an oral buccal swab, or any combination thereof. In some embodiments, the machine learning prediction model comprises a clustering algorithm, a statistical algorithm, or any combination thereof. In some embodiments, the clustering algorithm is a centroid-based algorithm, hierarchical clustering algorithm, or spectral clustering algorithm. In some embodiments, the centroid-based algorithm comprises a k-means clustering algorithm. In some embodiments, the statistical algorithm is a genome-wide prediction algorithm or a statistical prediction model. In some embodiments, the statistical prediction model is a genomic best linear unbiased prediction (GBLUP) or a Bayesian variable selection model. In some embodiments, the Bayesian variable selection model is single-step BayesC. In some embodiments, the method further comprises validating the machine learning prediction model using samples from a validation cohort of non-human subjects of the same species that have the one or more conditions. In some embodiments, the method further comprises training the machine learning prediction model using samples from a training cohort of non-human subjects of the same species, wherein the training comprises assigning one or more labels to a training data set obtained from the training cohort using a classification algorithm to produce a plurality of clusters, wherein each cluster is assigned a distinct label. In some embodiments, the training data set comprises (i) genetic data at a plurality of genomic loci of the training cohort, wherein the plurality of genomic loci are associated with the one or more conditions; and (ii) phenotypic data pertaining to a plurality of phenotypes of the training cohort of non-human subjects. In some embodiments, the method further comprises providing a notification to a guardian of the non-human subject or a veterinarian of the non-human subject, wherein the notification comprises: (i) the one or more conditions or the risk of developing the one or more conditions in the non-human subject; (ii) the genotype-phenotype profile of the non-human subject; (iii) a recommendation for a product, a behavioral modification, or any combination thereof, for the non-human subject; (iv) a prescription of a therapeutic or prophylactic intervention for the non-human subject; or (v) any combination of (i) to (iv). In some embodiments, the notification is an electronic report. In some embodiments, the notification further comprises a personal wellness system for the non-human subject. In some embodiments, the notification comprises the recommendation for the behavioral modification. In some embodiments, the behavioral modification is related to the one or more conditions. In some embodiments, the behavioral modification comprises increasing, reducing, or avoiding one or more activities. In some embodiments, the one or more activities comprises: (i) performance of a physical exercise; (ii) ingestion of a particular food, vitamin, or supplement; (iii) ingestion of particular quantities of the food, the vitamin, or the supplement; (iv) exposure to a product; (v) usage of a product, or (vi) any combination of (i) to (v). In some embodiments, the notification comprises the recommendation for the product, wherein the product comprises a nutritional product. In some embodiments, the nutritional product comprises a food, a supplement, a treat, or any combination thereof. In some embodiments, the method further comprising performing (a) to (c) iteratively at a plurality of time points over the lifespan of the non-human subject. In some embodiments, the method further comprising providing another notification to the guardian of the non-human subject, wherein the another notification comprises: (i) a new condition of the one or more conditions or the risk of developing the new condition in the non-human subject; (ii) an updated genotype-phenotype profile of the non-human subject; (iii) an updated recommendation for a product, a behavioral modification, or any combination thereof, for the non-human subject; (iv) an updated prescription of a therapeutic or prophylactic intervention for the non-human subject; or (v) any combination of (i) to (iv).

Aspects disclosed herein provide computer-implemented systems for identifying one or more conditions in a non-human subject, the computer-implemented systems comprising a computing device comprising at least one processor, an operating system configured to perform executable instructions, a memory, and a computer program including instructions executable by the computing device to create an application comprising: (a) a first software module configured to receive a data set comprising: (i) genetic data at a plurality of genomic loci of the non-human subject, wherein the plurality of genomic loci are associated with one or more conditions; and (ii) phenotypic data pertaining to a plurality of phenotypes of the non-human subject; (b) a second software module configured to produce a genotype-phenotype profile for the non-human subject by processing the data set to determine quantitative measures of at least one genomic locus of the plurality of genomic loci, and qualitative or quantitative measures of at least one phenotype of the plurality of phenotypes; and (c) a third software module configured to apply a machine learning prediction model to the genotype-phenotype profile of the non-human subject to produce the WPS, wherein the WPS is indicative of the non-human subject as having or not having the one or more conditions or a risk of developing the one or more conditions. In some embodiments, the WPS is a numerical value that is indicative of the likelihood that the non-human subject has the one or more conditions or a risk of developing the one or more conditions. In some embodiments, the third software module is further configured to identify the non-human subject as having a plurality of the one or more conditions or the risk of developing the plurality of the one or more conditions. In some embodiments, the one or more conditions comprises one or more genetic conditions, one or more nutritional conditions, one or more clinical conditions, one or more fitness conditions, one or more dermatological conditions or one or more allergy conditions, or any combination thereof. In some embodiments, the non-human subject is a mammal. In some embodiments, the mammal is a feline, a canine, or a farm animal. In some embodiments, the mammal is a companion animal. In some embodiments, the companion animal is the feline or canine. In some embodiments, the computer-implemented system further comprises a genotype device configured to obtain the genetic data from a biological sample from the non-human subject. In some embodiments, the genotype device comprises a sequencer, quantitative PCR (qPCR) device, or a DNA microarray. In some embodiments, the plurality of genomic loci comprises one or more polymorphisms. In some embodiments, the one or more polymorphisms comprises a single-nucleotide polymorphism (SNP) or an indel. In some embodiments, the plurality of genomic loci comprises at least 8 distinct loci. In some embodiments, the phenotypic data comprises information obtained from a guardian of the non-human subject, a veterinarian of the non-human subject, or a combination thereof. In some embodiments, the phenotypic data are input into an App or website by the guardian of the non-human subject or the veterinarian of the non-human subject. In some embodiments, the phenotypic data comprises physical attributes, clinical data, behavioral traits, or any combination thereof. In some embodiments, physical attributes comprise weight, sex, age, or breed. In some embodiments, the age is the biological age of the non-human subject as determined by measuring methylation of DNA in a biological sample obtained from the non-human subject. In some embodiments, clinical data comprises medical history or family medical history. In some embodiments, the medical history or the family medical history comprises diagnosis or prognosis of one or more diseases or one or more conditions, dietary sensitivities, lameness, allergies, activity level, exercise intolerance, reproductive status, pre-existing conditions, known adverse lifetime events, or any combination thereof. In some embodiments, the medical history or the family medical history comprises the diagnosis of the one or more diseases or the one or more conditions. In some embodiments, the medical history or the family medical history comprises the prognosis of the one or more diseases or the one or more conditions. In some embodiments, the one or more diseases or the one or more conditions is a dental disease or condition. In some embodiments, the behavioral traits comprise chewing, itching, aggression, neurosis, anxiety, energy level, or any combination thereof. In some embodiments, the environmental factors comprise geographic location, home life, activity level, activities performed, or frequency of activities, or any combination thereof. In some embodiments, the first software module is further configured to receive activity information of the non-human subject. In some embodiments, the activity information comprises activity level, activity type, calories burned, time asleep, or any combination thereof. In some embodiments, the activity data comprises information obtained from an activity tracking device. In some embodiments, the activity tracking device comprises a smart device. In some embodiments, the tracking device comprises a Global Positioning System (GPS)-connected dog collar. In some embodiments, the activity data comprises information obtained from a guardian of the non-human subject, a veterinarian of the non-human subject, or a combination thereof. In some embodiments, the activity data are input into an App or website by the guardian of the non-human subject or the veterinarian of the non-human subject. In some embodiments, the first software module is further configured to receive environmental data of the non-human subject. In some embodiments, the environmental data comprise a city environment, a rural environment, geographic location of residence, presence of allergens, time spent inside/outside, frequency of stair use, or any combination thereof. In some embodiments, the environmental data comprises information obtained from a guardian of the non-human subject, a veterinarian of the non-human subject, or a combination thereof. In some embodiments, the environmental data are input into an App or website by the guardian of the non-human subject or the veterinarian of the non-human subject. In some embodiments, the first software module is further configured to receive biomarker data for the non-human subject, wherein the biomarker data is obtained by assaying a biological sample from the non-human subject under conditions sufficient to detect an amount or a presence of one or more biomarkers, wherein the one or more biomarkers is associated with the one or more conditions. In some embodiments, the one or more biomarkers comprises a protein, sugar, lipid, hormone, vitamin, cell, metabolite, electrolyte, or any combination thereof. In some embodiments, the protein is an enzyme. In some embodiments, the enzyme is a digestive enzyme or a metabolic enzyme. In some embodiments, the digestive enzyme is lipase or an amylase. In some embodiments, the metabolic enzyme is a lactate dehydrogenase, a creatine phosphokinase, a gamma-glutamyl transpeptidase, a serum glutamate pyruvate transaminase, or an alkaline phosphatase. In some embodiments, the protein comprises total protein. In some embodiments, the protein is albumin, globulin, or a lipoprotein. In some embodiments, the lipoprotein is a low-density lipoprotein or a high-density lipoprotein. In some embodiments, the sugar comprises glucose. In some embodiments, the lipid comprises fatty acid. In some embodiments, the lipid comprises sterol. In some embodiments, the sterol is a cholesterol. In some embodiments, the hormone is cortisol or a thyroid hormone. In some embodiments, the thyroid hormone is triiodothyronine or thyroxine. In some embodiments, the vitamin comprises a fat-soluble vitamin or a water-soluble vitamin. In some embodiments, the cell comprises a red blood cell, a white blood cell, a platelet, or any combination thereof. In some embodiments, the metabolite is urea nitrogen, total bilirubin, or creatinine. In some embodiments, the electrolyte comprises sodium, potassium, chloride, calcium, phosphorus, or any combination thereof. In some embodiments, the biological sample comprises a tissue biopsy, peripheral blood, capillary blood, a stool sample, a urine sample, an oral buccal swab, or any combination thereof. In some embodiments, the machine learning prediction model was validated using biopsies from a cohort of non-human subjects that have been analyzed and interpreted as corresponding to the one or more conditions being predicted by the machine learning prediction model. In some embodiments, the machine learning prediction model was trained using samples from a training cohort of non-human subjects of the same species, wherein training the machine learning prediction model comprises assigning one or more labels to a training data set obtained from the training cohort using a classification algorithm to produce a plurality of clusters, wherein each cluster is assigned a distinct label. In some embodiments, the training data set comprises (i) genetic data at a plurality of genomic loci of the training cohort, wherein the plurality of genomic loci is associated with the one or more conditions; and (ii) phenotypic data pertaining to a plurality of phenotypes of the training cohort of non-human subjects. In some embodiments, the computer-implemented system further comprises a display module communicatively coupled to the computing device, wherein the display module is configured to provide a notification to a user, wherein the user comprises a guardian of the non-human subject or a veterinarian of the non-human subject, wherein the notification comprises: (i) the one or more conditions or the risk of developing the one or more conditions in the non-human subject; (ii) the genotype-phenotype profile of the non-human subject; (iii) a recommendation for a product, a behavioral modification, or any combination thereof, for the non-human subject; (iv) a prescription of a therapeutic or prophylactic intervention for the non-human subject; or (v) any combination of (i) to (iv). In some embodiments, the notification is displayed to the user by a graphical user interface (GUI) of the computing device. In some embodiments, the notification is an electronic report visible to the user on the GUI. In some embodiments, the notification comprises the recommendation for the behavioral modification. In some embodiments, the behavioral modification is related to the one or more conditions. In some embodiments, the behavioral modification related to the one or more conditions comprises increasing, reducing, or avoiding one or more activities. In some embodiments, the activity comprises: (i) performance of a physical exercise; (ii) ingestion of a particular food, vitamin, or supplement; (iii) ingestion of particular quantities of the food, the vitamin, or the supplement; (iv) exposure to a product; (v) usage of a product; or (vi) any combination of (i) to (v). In some embodiments, the notification comprises the recommendation for the product, wherein the product comprises a nutritional product. In some embodiments, the nutritional product comprises a food, a supplement, a treat, or any combination thereof. In some embodiments, the first software module, the second software module and the third software module are further configured to analyze new data sets for the non-human subject at a plurality of time points to provide an updated WPS. In some embodiments, the display module is further configured to provide another notification to the user, wherein the another notification comprises: (i) a new condition of the one or more conditions or the risk of developing the new condition in the non-human subject; (ii) an updated genotype-phenotype profile of the non-human subject; (iii) an updated recommendation for a product, a behavioral modification, or any combination thereof, for the non-human subject; (iv) an updated prescription of a therapeutic or prophylactic intervention for the non-human subject; or (v) any combination of (i) to (iv). In some embodiments, the machine learning prediction model comprises a clustering algorithm, a statistical algorithm, or any combination thereof. In some embodiments, the clustering algorithm is a centroid-based algorithm, hierarchical clustering algorithm, or spectral clustering algorithm. In some embodiments, the centroid-based algorithm comprises a k-means clustering algorithm. In some embodiments, the statistical algorithm is a genome-wide prediction algorithm or a statistical prediction model. In some embodiments, the statistical prediction model is a genomic best linear unbiased prediction (GBLUP) or a Bayesian variable selection model. In some embodiments, the Bayesian variable selection model is single-step BayesC.

Aspects disclosed herein provide methods for identifying one or more conditions in a non-human subject, the method comprising: a method of implementing a personalized wellness system for a non-human subject, the method comprising: providing to the non-human subject a recommendation based, at least in part, on a wellness probability score (WPS) for the non-human subject, wherein the WPS is determined by: (a) applying a machine learning prediction model to a data set comprising: (i) genetic data at a plurality of genomic loci of the non-human subject and (ii) phenotypic data pertaining to a plurality of phenotypes of the non-human subject; (b) producing a genotype-phenotype profile for the non-human subject by processing the data set to determine quantitative measures of at least one genomic locus of the plurality of genomic loci, and qualitative or quantitative measures of at least one phenotype of the plurality of phenotypes; and (c) applying a machine learning prediction model to the genotype-phenotype profile of the non-human subject to produce the WPS for the non-human subject, wherein the WPS is indicative of whether the non-human subject has the one or more conditions or has a risk of developing the one or more conditions. In some embodiments, the WPS is a numerical value that is indicative of the likelihood that the non-human subject has the one or more conditions or a risk of developing the one or more conditions. In some embodiments, the recommendation comprises a product, a behavioral modification, or any combination thereof, for the non-human subject. In some embodiments, the product is consumed or used on, with, or by, or any combination thereof by the non-human subject. In some embodiments, the product that is consumed is a nutritional product, a supplement, a treat, a medicine. In some embodiments, the one or more conditions comprises one or more genetic conditions, one or more nutritional conditions, one or more clinical conditions, one or more fitness conditions, one or more dermatological conditions or one or more allergy conditions, or any combination thereof. In some embodiments, the non-human subject is a mammal. In some embodiments, the mammal is a feline, a canine, or a farm animal. In some embodiments, the mammal is a companion animal. In some embodiments, the companion animal is the feline or canine. In some embodiments, the genetic data is determined by: (a) obtaining or having obtained a biological sample from the non-human subject; and (b) performing or having performed a genotyping assay on the biological sample. In some embodiments, performing or having performed the genotyping assay comprises: (i) subjecting the biological sample to conditions that are sufficient to isolate, enrich, or extract a plurality of DNA molecules from the biological sample; and (ii) analyzing the plurality of DNA molecules to generate the genetic data. In some embodiments, the analyzing the plurality of DNA molecules comprises performing whole genome sequencing, skim sequencing, quantitative PCR (qPCR), or analysis using a DNA microarray. In some embodiments, the plurality of genomic loci comprises one or more polymorphisms. In some embodiments, the one or more polymorphisms comprises a single-nucleotide polymorphism (SNP) or an indel. In some embodiments, the plurality of genomic loci comprises at least 8 distinct loci. In some embodiments, the phenotypic data comprises information obtained from a guardian of the non-human subject, a veterinarian of the non-human subject, or a combination thereof. In some embodiments, receiving the phenotypic data from an App or website populated by the guardian of the non-human subject or the veterinarian of the non-human subject. In some embodiments, the phenotypic data comprises physical attributes, clinical data, behavioral traits, or any combination thereof. In some embodiments, physical attributes comprise weight, sex, age, or breed. In some embodiments, the age is the biological age of the non-human subject as determined by measuring methylation of DNA in a biological sample obtained from the non-human subject. In some embodiments, clinical data comprises medical history or family medical history. In some embodiments, the medical history or the family medical history comprises diagnosis or prognosis of one or more diseases or one or more conditions, dietary sensitivities, lameness, allergies, activity level, exercise intolerance, reproductive status, pre-existing conditions, known adverse lifetime events, or any combination thereof. In some embodiments, the medical history or the family medical history comprises the diagnosis of the one or more diseases or the one or more conditions. In some embodiments, the medical history or the family medical history comprises the prognosis of the one or more diseases or the one or more conditions. In some embodiments, the one or more diseases or the one or more conditions is a dental disease or condition. In some embodiments, behavioral traits comprise chewing, itching, aggression, neurosis, anxiety, energy level, or any combination thereof. In some embodiments, the method further comprises receiving activity information of the non-human subject. In some embodiments, the activity information comprises activity level, activity type, calories burned, time asleep, or any combination thereof. In some embodiments, the activity data comprises information obtained from an activity tracking device. In some embodiments, the activity tracking device comprises a smart device. In some embodiments, the tracking device comprises a Global Positioning System (GPS)-connected dog collar. In some embodiments, the activity data comprises information obtained from a guardian of the non-human subject, a veterinarian of the non-human subject, or a combination thereof. In some embodiments, the activity data are input into an App or website by the guardian of the non-human subject or the veterinarian of the non-human subject. In some embodiments, the method further comprises receiving environmental data of the non-human subject. In some embodiments, the environmental data comprise a city environment, a rural environment, geographic location of residence, presence of allergens, time spent inside/outside, frequency of stair use, or any combination thereof. In some embodiments, the environmental data comprises information obtained from a guardian of the non-human subject, a veterinarian of the non-human subject, or a combination thereof. In some embodiments, the environmental data are input into an App or website by the guardian of the non-human subject or the veterinarian of the non-human subject. In some embodiments, the method further comprises receiving biomarker data for the non-human subject, wherein the biomarker data is obtained by assaying a biological sample from the non-human subject under conditions sufficient to detect an amount or a presence of one or more biomarkers, wherein the one or more biomarkers is associated with the one or more conditions. In some embodiments, the one or more biomarkers comprises a protein, sugar, lipid, hormone, vitamin, cell, metabolite, electrolyte, or any combination thereof. In some embodiments, the protein is an enzyme. In some embodiments, the enzyme is a digestive enzyme or a metabolic enzyme. In some embodiments, the digestive enzyme is lipase or an amylase. In some embodiments, the metabolic enzyme is a lactate dehydrogenase, a creatine phosphokinase, a gamma-glutamyl transpeptidase, a serum glutamate pyruvate transaminase, or an alkaline phosphatase. In some embodiments, the protein comprises total protein. In some embodiments, the protein is albumin, globulin, or a lipoprotein. In some embodiments, the lipoprotein is a low-density lipoprotein or a high-density lipoprotein. In some embodiments, the sugar comprises glucose. In some embodiments, the lipid comprises fatty acid. In some embodiments, the lipid comprises sterol. In some embodiments, the sterol is a cholesterol. In some embodiments, the hormone is cortisol or a thyroid hormone. In some embodiments, the thyroid hormone is triiodothyronine or thyroxine. In some embodiments, the vitamin comprises a fat-soluble vitamin or a water-soluble vitamin. In some embodiments, the cell comprises a red blood cell, a white blood cell, a platelet, or any combination thereof. In some embodiments, the metabolite is urea nitrogen, total bilirubin, or creatinine. In some embodiments, the electrolyte comprises sodium, potassium, chloride, calcium, phosphorus, or any combination thereof. In some embodiments, the biological sample comprises a tissue biopsy, peripheral blood, capillary blood, a stool sample, a urine sample, an oral buccal swab, or any combination thereof. In some embodiments, the machine learning prediction model comprises a clustering algorithm, a statistical algorithm, or any combination thereof. In some embodiments, the clustering algorithm is a centroid-based algorithm, hierarchical clustering algorithm, or spectral clustering algorithm. In some embodiments, the centroid-based algorithm comprises a k-means clustering algorithm. In some embodiments, the statistical algorithm is a genome-wide prediction algorithm or a statistical prediction model. In some embodiments, the statistical prediction model is a genomic best linear unbiased prediction (GBLUP) or a Bayesian variable selection model. In some embodiments, the Bayesian variable selection model is single-step BayesC. In some embodiments, the machine learning prediction model was validated using samples from a validation cohort of non-human subjects of the same species that have the one or more conditions. In some embodiments, the machine learning prediction model was trained using samples from a training cohort of non-human subjects of the same species, wherein the training comprises assigning one or more labels to a training data set obtained from the training cohort using a classification algorithm to produce a plurality of clusters, wherein each cluster is assigned a distinct label. In some embodiments, the training data set comprises (i) genetic data at a plurality of genomic loci of a training cohort of non-human subjects, wherein the plurality of genomic loci are associated with the one or more conditions; and (ii) phenotypic data pertaining to a plurality of phenotypes of the training cohort of non-human subjects. In some embodiments, the genetic data and the phenotypic data of the training data set are stored in a data base that is curated by a network configured to transform raw data into a data structure suitable for input into the machine learning prediction model. In some embodiments, the method further comprises comprising providing a notification to a guardian of the non-human subject or a veterinarian of the non-human subject, wherein the notification comprises: (i) the one or more conditions or the risk of developing the one or more conditions in the non-human subject; (ii) a genotype-phenotype profile of the non-human subject; (iii) a recommendation for a product, a behavioral modification, or any combination thereof, for the non-human subject; (iv) a prescription of a therapeutic or prophylactic intervention for the non-human subject; or (v) any combination of (i) to (iv). In some embodiments, the notification is an electronic report. In some embodiments, the notification further comprises a personal wellness system for the non-human subject. In some embodiments, the notification comprises the recommendation for the behavioral modification. In some embodiments, the behavioral modification is related to the one or more conditions. In some embodiments, the behavioral modification comprises increasing, reducing, or avoiding one or more activities. In some embodiments, the one or more activities comprises: (i) performance of a physical exercise; (ii) ingestion of a particular food, vitamin, or supplement; (iii) ingestion of particular quantities of the food, the vitamin, or the supplement; (iv) exposure to a product; (v) usage of a product, or (vi) any combination of (i) to (v). In some embodiments, the notification comprises the recommendation for the product, wherein the product comprises a nutritional product. In some embodiments, the nutritional product comprises a food, a supplement, a treat, or any combination thereof. In some embodiments, the method further comprises delivering to the non-human subject a second nutritional product based, at least in part, on an updated wellness probability score (WPS) for the non-human subject, wherein the updated WPS is determined by performing (a) to (c) iteratively at a plurality of time points over the lifespan of the non-human subject. In some embodiments, the method further comprising providing another notification to the guardian of the non-human subject, wherein the another notification comprises: (i) a new condition of the one or more conditions or the risk of developing the new condition in the non-human subject; (ii) an updated genotype-phenotype profile of the non-human subject; (iii) an updated recommendation for a product, a behavioral modification, or any combination thereof, for the non-human subject; (iv) an updated prescription of a therapeutic or prophylactic intervention for the non-human subject; or (v) any combination of (i) to (iv).

Aspects disclosed herein provide methods for identifying one or more conditions in a non-human subject, the method comprising: a method of implementing a personalized wellness system for a non-human subject, the method comprising: (a) determining whether the non-human subject has one or more conditions or is at risk of developing the one or more conditions by: (i) obtaining or having obtained a biological sample from the non-human subject; (ii) performing or having performed a genotyping assay on the biological sample to produce genetic data; (iii) receiving phenotypic data for the non-human subject; and (iv) applying a machine learning prediction model to a data set comprising the genetic data and the phenotypic data to determine if the non-human subject has the one or more conditions or a risk of developing the one or more conditions; and (b) if the non-human subject has the one or more conditions or a risk of developing the one or more conditions, then providing to the non-human subject a recommendation to remedy the one or more conditions or the risk of developing the one or more conditions, and if the non-human subject does not have the one or more conditions or a risk of developing the one or more conditions, then providing to the subject another recommendation that would not remedy the one or more conditions or the risk of developing the one or more conditions. In some embodiments, the method further comprises calculating a wellness probability score (WPS) based, at least in part, on the genetic data and the phenotype data for the non-human subject. In some embodiments, the WPS is a numerical value that is indicative of the likelihood that the non-human subject has the one or more conditions or a risk of developing the one or more conditions. In some embodiments, the recommendation comprises a product, a behavioral modification, or any combination thereof, for the non-human subject. In some embodiments, the product is consumed or used on, with, or by, or any combination thereof by the non-human subject. In some embodiments, the product that is consumed is a nutritional product, a supplement, a treat, a medicine. In some embodiments, the another recommendation comprises a product, a behavioral modification, or any combination thereof, for the non-human subject. In some embodiments, the product is consumed or used on, with, or by, or any combination thereof by the non-human subject. In some embodiments, the product that is consumed is a nutritional product, a supplement, a treat, a medicine. In some embodiments, the method further comprises identifying the non-human subject as having a plurality of the one or more conditions or the risk of developing the plurality of the one or more conditions. In some embodiments, the one or more conditions comprises one or more genetic conditions, one or more nutritional conditions, one or more clinical conditions, one or more fitness conditions, one or more dermatological conditions or one or more allergy conditions, or any combination thereof. In some embodiments, the non-human subject is a mammal. In some embodiments, the mammal is a feline, a canine, or a farm animal. In some embodiments, the mammal is a companion animal. In some embodiments, the companion animal is the feline or canine. In some embodiments, performing the genotyping assay comprises: (i) subjecting the biological sample to conditions that are sufficient to isolate, enrich, or extract a plurality of DNA molecules from the biological sample; and (ii) analyzing the plurality of DNA molecules to generate the genetic data. In some embodiments, the analyzing the plurality of DNA molecules comprises performing whole genome sequencing, skim sequencing, quantitative PCR (qPCR), or analysis using a DNA microarray. In some embodiments, the plurality of genomic loci comprises one or more polymorphisms. In some embodiments, the one or more polymorphisms comprises a single-nucleotide polymorphism (SNP) or an indel. In some embodiments, the plurality of genomic loci comprises at least 8 distinct loci. In some embodiments, the phenotypic data comprises information obtained from a guardian of the non-human subject, a veterinarian of the non-human subject, or a combination thereof. In some embodiments, receiving the phenotypic data from an App or website populated by the guardian of the non-human subject or the veterinarian of the non-human subject. In some embodiments, the phenotypic data comprises physical attributes, clinical data, behavioral traits, or any combination thereof. In some embodiments, physical attributes comprise weight, sex, age, or breed. In some embodiments, the age is the biological age of the non-human subject as determined by measuring methylation of DNA in a biological sample obtained from the non-human subject. In some embodiments, clinical data comprises medical history or family medical history. In some embodiments, the medical history or the family medical history comprises diagnosis or prognosis of one or more diseases or one or more conditions, dietary sensitivities, lameness, allergies, activity level, exercise intolerance, reproductive status, pre-existing conditions, known adverse lifetime events, or any combination thereof. In some embodiments, the medical history or the family medical history comprises the diagnosis of the one or more diseases or the one or more conditions. In some embodiments, the medical history or the family medical history comprises the prognosis of the one or more diseases or the one or more conditions. In some embodiments, the one or more diseases or the one or more conditions is a dental disease or condition. In some embodiments, behavioral traits comprise chewing, itching, aggression, neurosis, anxiety, energy level, or any combination thereof. In some embodiments, the data set further comprises activity information of the non-human subject. In some embodiments, the activity information comprises activity level, activity type, calories burned, time asleep, or any combination thereof. In some embodiments, the activity data comprises information obtained from an activity tracking device. In some embodiments, the activity tracking device comprises a smart device. In some embodiments, the tracking device comprises a Global Positioning System (GPS)-connected dog collar. In some embodiments, the activity data comprises information obtained from a guardian of the non-human subject, a veterinarian of the non-human subject, or a combination thereof. In some embodiments, the activity data are input into an App or website by the guardian of the non-human subject or the veterinarian of the non-human subject. In some embodiments, the data set further comprises environmental data of the non-human subject. In some embodiments, the environmental data comprise a city environment, a rural environment, geographic location of residence, presence of allergens, time spent inside/outside, frequency of stair use, or any combination thereof. In some embodiments, the environmental data comprises information obtained from a guardian of the non-human subject, a veterinarian of the non-human subject, or a combination thereof. In some embodiments, the environmental data are input into an App or website by the guardian of the non-human subject or the veterinarian of the non-human subject. In some embodiments, the data set further comprises biomarker data for the non-human subject, wherein the biomarker data is obtained by assaying a biological sample from the non-human subject under conditions sufficient to detect an amount or a presence of one or more biomarkers, wherein the one or more biomarkers is associated with the one or more conditions. In some embodiments, the one or more biomarkers comprises a protein, sugar, lipid, hormone, vitamin, cell, metabolite, electrolyte, or any combination thereof. In some embodiments, the protein is an enzyme. In some embodiments, the enzyme is a digestive enzyme or a metabolic enzyme. In some embodiments, the digestive enzyme is lipase or an amylase. In some embodiments, the metabolic enzyme is a lactate dehydrogenase, a creatine phosphokinase, a gamma-glutamyl transpeptidase, a serum glutamate pyruvate transaminase, or an alkaline phosphatase. In some embodiments, the protein comprises total protein. In some embodiments, the protein is albumin, globulin, or a lipoprotein. In some embodiments, the lipoprotein is a low-density lipoprotein or a high-density lipoprotein. In some embodiments, the sugar comprises glucose. In some embodiments, the lipid comprises fatty acid. In some embodiments, the lipid comprises sterol. In some embodiments, the sterol is a cholesterol. In some embodiments, the hormone is cortisol or a thyroid hormone. In some embodiments, the thyroid hormone is triiodothyronine or thyroxine. In some embodiments, the vitamin comprises a fat-soluble vitamin or a water-soluble vitamin. In some embodiments, the cell comprises a red blood cell, a white blood cell, a platelet, or any combination thereof. In some embodiments, the metabolite is urea nitrogen, total bilirubin, or creatinine. In some embodiments, the electrolyte comprises sodium, potassium, chloride, calcium, phosphorus, or any combination thereof. In some embodiments, the biological sample comprises a tissue biopsy, peripheral blood, capillary blood, a stool sample, a urine sample, an oral buccal swab, or any combination thereof. In some embodiments, the machine learning prediction model comprises a clustering algorithm, a statistical algorithm, or any combination thereof. In some embodiments, the clustering algorithm is a centroid-based algorithm, hierarchical clustering algorithm, or spectral clustering algorithm. In some embodiments, the centroid-based algorithm comprises a k-means clustering algorithm. In some embodiments, the statistical algorithm is a genome-wide prediction algorithm or a statistical prediction model. In some embodiments, the statistical prediction model is a genomic best linear unbiased prediction (GBLUP) or a Bayesian variable selection model. In some embodiments, the Bayesian variable selection model is single-step BayesC. In some embodiments, the method further comprises validating the machine learning prediction model using samples from a validation cohort of non-human subjects of the same species that have the one or more conditions. In some embodiments, the method further comprises training the machine learning prediction model using samples from a training cohort of non-human subjects of the same species, wherein the training comprises assigning one or more labels to a training data set obtained from the training cohort using a classification algorithm to produce a plurality of clusters, wherein each cluster is assigned a distinct label. In some embodiments, the training data set comprises (i) genetic data at a plurality of genomic loci of the training cohort, wherein the plurality of genomic loci is associated with the one or more conditions; and (ii) phenotypic data pertaining to a plurality of phenotypes of the training cohort of non-human subjects. In some embodiments, the method further comprises providing a notification to a guardian of the non-human subject or a veterinarian of the non-human subject, wherein the notification comprises: (i) the one or more conditions or the risk of developing the one or more conditions in the non-human subject; (ii) the genotype-phenotype profile of the non-human subject; (iii) a recommendation for a product, a behavioral modification, or any combination thereof, for the non-human subject; (iv) a prescription of a therapeutic or prophylactic intervention for the non-human subject; or (v) any combination of (i) to (iv). In some embodiments, the notification is an electronic report. In some embodiments, the notification further comprises a personal wellness system for the non-human subject. In some embodiments, the notification comprises the recommendation for the behavioral modification. In some embodiments, the behavioral modification is related to the one or more conditions. In some embodiments, the behavioral modification comprises increasing, reducing, or avoiding one or more activities. In some embodiments, the one or more activities comprises: (i) performance of a physical exercise; (ii) ingestion of a particular food, vitamin, or supplement; (iii) ingestion of particular quantities of the food, the vitamin, or the supplement; (iv) exposure to a product; (v) usage of a product, or (vi) any combination of (i) to (v). In some embodiments, the notification comprises the recommendation for the product, wherein the product comprises a nutritional product. In some embodiments, the nutritional product comprises a food, a supplement, a treat, or any combination thereof. In some embodiments, the method further comprising performing (a) to (b) iteratively at a plurality of time points over the lifespan of the non-human subject. In some embodiments, the method further comprising providing another notification to the guardian of the non-human subject, wherein the another notification comprises: (i) a new condition of the one or more conditions or the risk of developing the new condition in the non-human subject; (ii) an updated genotype-phenotype profile of the non-human subject; (iii) an updated recommendation for a product, a behavioral modification, or any combination thereof, for the non-human subject; (iv) an updated prescription of a therapeutic or prophylactic intervention for the non-human subject; or (v) any combination of (i) to (iv).

Aspects disclosed herein provide methods for training a machine learning model, the methods comprising: (a) receiving, by the machine learning model, a plurality of training profiles obtained for a plurality of non-human animals, wherein the machine learning model comprises one or more parameters, wherein the plurality of training profiles is related to a genotype and a phenotype of a non-human animal of the plurality of non-human animals; (b) providing a recommendation indicating the non-human animal as having one or more conditions or a risk of developing the one or more conditions; (c) receiving, at the machine learning model, an updated recommendation; and (d) adjusting the one or more parameters of the machine learning model based on the updated recommendation, thereby training the machine learning model.

Aspects disclosed herein provide methods for identifying one or more conditions in a non-human animal subject, the method comprising: (a) receiving a data set comprising: (i) genetic data at a plurality of genomic loci of the non-human animal subject, wherein at least one genomic locus of the plurality of genomic loci is associated with the one or more conditions; and (ii) phenotypic data pertaining to a plurality of phenotypes of the non-human animal subject; (b) producing a genotype-phenotype profile for the non-human animal subject by processing the data set to determine quantitative measures of the at least one genomic locus of the plurality of genomic loci, and qualitative or quantitative measures of at least one phenotype of the plurality of phenotypes; and (c) applying a machine learning prediction model to the genotype-phenotype profile of the non-human animal subject to identify the non-human subject as having the one or more conditions or a risk of developing the one or more conditions. In some embodiments, the one or more conditions comprises one or more genetic conditions, one or more nutritional conditions, one or more clinical conditions, one or more fitness conditions, one or more dermatological conditions or one or more allergy conditions, or any combination thereof. In some embodiments, the non-human animal is a feline, a canine, or a farm animal. In some embodiments, the non-human animal subject is a companion animal. In some embodiments, the genetic data is determined by: (i) obtaining or having obtained a biological sample from the non-human animal subject; and (ii) performing or having performed a genotyping assay on the biological sample. In some embodiments, the method further comprises receiving the genetic data from a nucleic acid sequencing device, wherein the nucleic acid sequencing device comprises a whole genome sequencer, a skim sequencer, a quantitative PCR (qPCR) device, or a DNA microarray. In some embodiments, the at least one genomic locus comprises one or more polymorphisms. In some embodiments, the method further comprises receiving the phenotypic data from a guardian of the non-human animal subject, a veterinarian of the non-human animal subject, or a combination thereof. In some embodiments, the phenotypic data comprises one or more physical attributes, clinical information, one or more behavioral traits, or any combination thereof. In some embodiments, one or more physical attributes comprises weight, body mass index, sex, age, or breed of the non-human animal subject. In some embodiments, the clinical data comprises medical history of the non-human animal subject or medical history of a biological relative of the non-human animal subject. In some embodiments, the one or more behavioral traits comprises chewing, itching, aggression, neurosis, anxiety, energy level, or any combination thereof. In some embodiments, the method further comprises: (d) receiving activity data of the non-human animal subject; (e) updating the data set with the activity data to produce an updated data set; and (f) applying the machine learning model to the updated data set. In some embodiments, the activity data comprises activity level, activity type, calories burned, time asleep, or any combination thereof. In some embodiments, the activity data comprises information obtained from an activity tracking device. In some embodiments, the method further comprises: (d) receiving environmental data of the non-human animal subject; (e) updating the data set with the environmental data to produce an updated data set; and (f) applying the machine learning model to the updated data set. In some embodiments, the environmental data comprise a city environment, a rural environment, geographic location of residence, presence of allergens, time spent inside/outside, frequency of stair use, or any combination thereof. In some embodiments, the method further comprises: (d) receiving biomarker data for the non-human animal subject, wherein the biomarker data comprises a presence or a level of one or more biomarkers detected in a biological sample obtained from the non-human animal subject, wherein the one or more biomarkers comprises a protein, sugar, lipid, hormone, vitamin, cell, metabolite, electrolyte or mineral, or any combination thereof; (e) updating the data set with the biomarker data a to produce an updated data set; and (f) applying the machine learning model to the updated data set. In some embodiments, the machine learning prediction model comprises a clustering algorithm, a decision tree algorithm, a statistical algorithm, gradient boosted machine (GBM), or any combination thereof. In some embodiments, the clustering algorithm is a centroid-based clustering algorithm. In some embodiments, the statistical prediction model is a genomic best linear unbiased prediction (GBLUP) or a Bayesian variable selection model. In some embodiments, the method further comprises validating the machine learning prediction model using samples from a validation cohort of non-human animal subjects of the same species that have the one or more conditions. In some embodiments, the method further comprises training the machine learning prediction model using samples from a training cohort of non-human animal subjects of the same species. In some embodiments, the training data set comprises: (i) genetic data at a plurality of genomic loci of the training cohort, wherein the plurality of genomic loci is associated with the one or more conditions; and (ii) phenotypic data pertaining to a plurality of phenotypes of the training cohort of non-human animal subjects. In some embodiments, the method further comprises providing a notification to a guardian of the non-human animal subject or a veterinarian of the non-human animal subject, wherein the notification comprises: (i) the one or more conditions or the risk of developing the one or more conditions in the non-human subject; (ii) the genotype-phenotype profile of the non-human subject; (iii) a recommendation for a product, a behavioral modification, or any combination thereof, for the non-human subject; (iv) a prescription of a therapeutic or prophylactic intervention for the non-human subject; or (v) any combination of (i) to (iv). In some embodiments, the behavioral modification comprises increasing, reducing, or avoiding one or more activities. In some embodiments, the one or more activities comprises: (i) performance of a physical exercise; (ii) ingestion of a type or quantity of food, supplement, or treat; (iii) exposure to the product; (iv) usage of the product, or (v) any combination of (i) to (iv). In some embodiments, the product is a food, supplement or a treat that is manufactured to improve, ameliorate, or prevent the one or more conditions in the non-human animal subject. In some embodiments, the method further comprises: (d) performing (a) to (c) iteratively at a plurality of time points over a lifespan of the non-human animal subject with biomarker data, environmental data, activity data, or phenotype data to produce an updated data set; and (e) applying the machine learning prediction model to the updated data set to identify the non-human subject as having the one or more conditions or the risk of developing the one or more conditions. In some embodiments, the method further comprises providing a notification to a guardian of the non-human animal subject or a veterinarian of the non-human animal subject at one or more of the plurality of time points, wherein the notification comprises: (i) the one or more conditions or the risk of developing the one or more conditions in the non-human subject; (ii) the genotype-phenotype profile of the non-human subject; (iii) a recommendation for a product, a behavioral modification, or any combination thereof, for the non-human subject; (iv) a prescription of a therapeutic or prophylactic intervention for the non-human subject; or (v) any combination of (i) to (iv).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents and patent applications incorporated by reference contradict the disclosure contained in the specification, the specification is intended to supersede and/or take precedence over any such contradictory material.

BRIEF DESCRIPTION OF THE DRAWINGS

The novel features of the inventive concept are set forth with particularity in the appended claims. A better understanding of the features and advantages of the present inventive concept will be obtained by reference to the following detailed description that sets forth illustrative embodiments, in which the principles of the inventive concept are utilized, and the accompanying drawings (also "Figure" and "FIG." herein), of which:

FIG. 5A depicts a non-limiting example GUI for viewing a DNA report, genotypic data, or phenotypic data of an animal. FIG. 5B depicts a non-limiting example GUI for viewing genotypic data of an animal. FIG. 5C depicts a non-limiting example GUI for viewing and/or editing activity and consumption data of an animal. FIG. 5D depicts a non-limiting example GUI for viewing and/or editing activity data of an animal.

FIG. 6A depicts a non-limiting view of the GUI displaying one or more elements regarding food deliveries. FIG. 6B depicts a non-limiting view of the GUI displaying one or more elements regarding upcoming and current deliveries.

FIG. 7A depicts a non-limiting view of the GUI displaying one or more elements for initializing a login or creation of an account. FIG. 7B depicts a non-limiting view of the GUI displaying one or more elements regarding location data of a user. FIG. 7C depicts a non-limiting view of the GUI displaying one or more elements regarding user data. FIG. 7D depicts a non-limiting view of the GUI displaying one or more elements regarding security data for a user. FIG. 7E depicts a non-limiting view of the GUI displaying one or more elements for inputting profile data. FIG. 7F depicts a non-limiting view of the GUI displaying one or more elements regarding representation of the animal. FIG. 7G depicts a non-limiting view of the GUI displaying one or more elements regarding confirmation or editing of representation of the animal.

FIG. 8A depicts a non-limiting view of the GUI displaying one or more elements for beginning activation of a kit or assisting with collecting a sample. FIG. 8B depicts a non-limiting view of the GUI displaying one or more elements regarding preparing to collect a sample. FIG. 8C depicts a non-limiting view of the GUI displaying one or more elements for activating a kit for sample collection.

DETAILED DESCRIPTION

Figure 1:
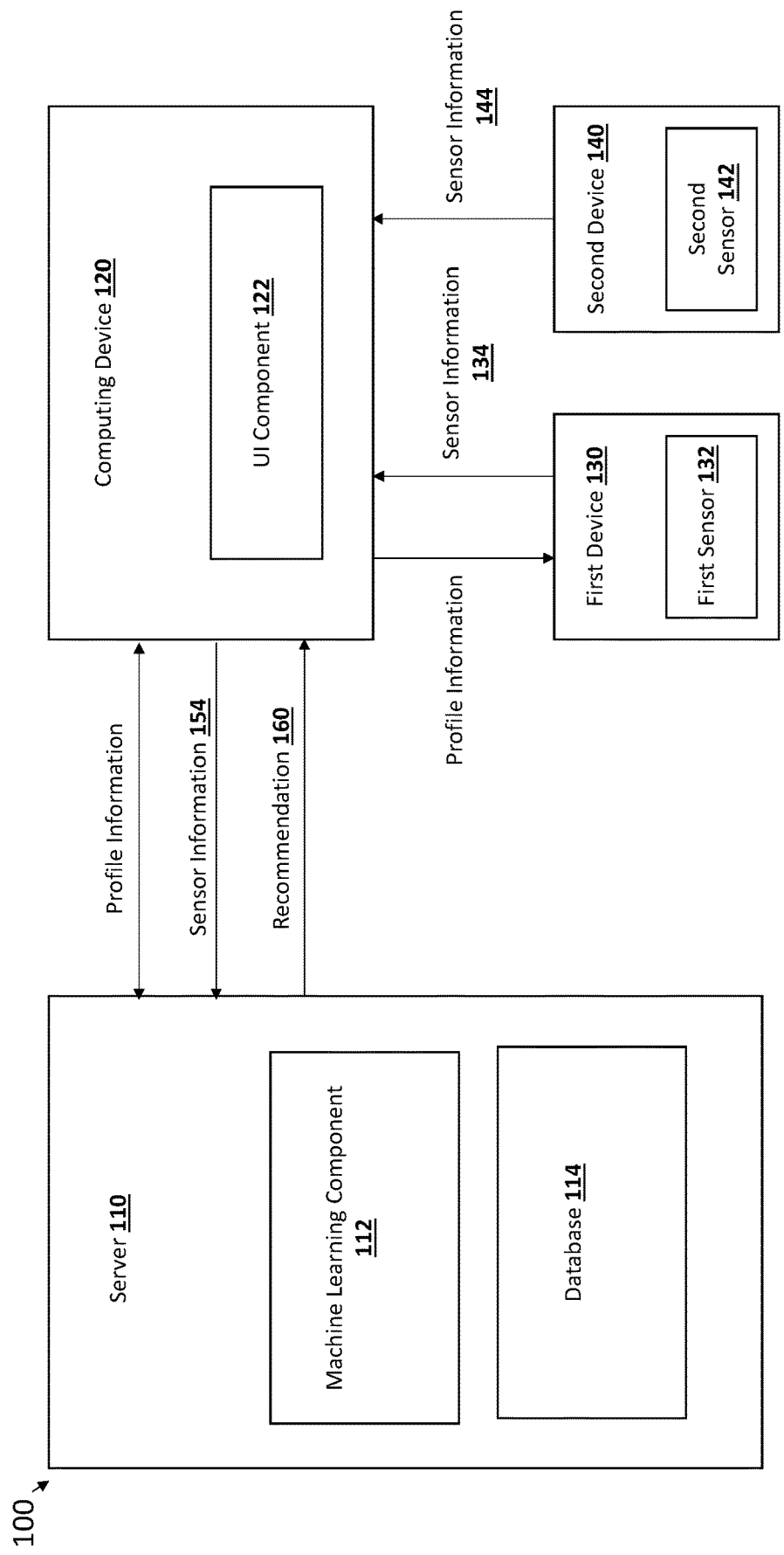
FIG. 1 depicts a non-limiting example of a system for identifying an animal as having one or more conditions or at a risk of developing the one or more conditions.

Current foods on the market for animals are one size fits all. However, all animals are different, even those within the same species or breed. Disclosed herein are personalized wellness systems and methods of their use to generate custom recommendations for an animal disclosed herein, such as a non-human animal. The personalized wellness systems disclosed herein provide a wellness probability score (WPS) predictive of whether an animal has, or is at risk to develop, one or more conditions. The WPS disclosed herein is useful for a variety of purposes, including, but not limited to, selecting a treatment regimen for the animal, proscribing a diet to the animal, recommending a product (e.g., food, supplements, vitamins, exercise, skin care, hair care, and the like) to the animal.

Methods

Disclosed herein are methods of producing a personalized wellness system for a subject disclosed herein, such as a companion animal or a farm animal. The personalized wellness systems disclosed herein are based on an analysis of a genotype, a phenotype or a combination of a genotype and phenotype of the subject. Such genotype and phenotype information may be used to generate a genotype-phenotype profile for the subject. In some embodiments, the personalized wellness systems are additionally based on the environment, the activity, or the behavior, of the subject. The methods disclosed herein may be computer-implemented. In a non-limiting example, the genotype-phenotype profile and/or environmental data, activity data, and/or behavior data can be input into a machine learning model, which can predict a likelihood that the subject an animal has, or is at risk to develop, one or more conditions disclosed herein. In some embodiments, the result from the machine learning model is in the form of a score, such as a wellness probability score (WPS). Also provided are methods of recommending a nutritional product, a behavior modification, or a therapeutic intervention based, at least in part, on the WPS for the subject. The WPS or recommendations may be communicated to an individual by an Application (App) on a personal electronic device (e.g., smartphone or tablet).

The personalized wellness system for the subject can be modified throughout the life of the subject. For example, a companion animal having, or having a susceptibility to developing, a particular disease or condition may be monitored using the personalized wellness system on a regular basis. Regular check-ups at the veterinarian may include measuring one or more biomarkers disclosed herein (e.g., RNA, protein, metabolite, sugar, lipid, hormone vitamin, cell, electrolyte, or mineral). Such biomarker data can be input into the machine learning model to update the WPS for the subject. Additional information, such as clinical information (e.g., disease onset, relapse, progression, severity) may be input into the machine learning model to update the WPS. In some cases, the recommendations may change over time, depending on changes to the WPS for the subject. Thus, methods disclosed herein also comprise methods of detecting one or more biomarkers or a genotype in the subject.

Figure 12:
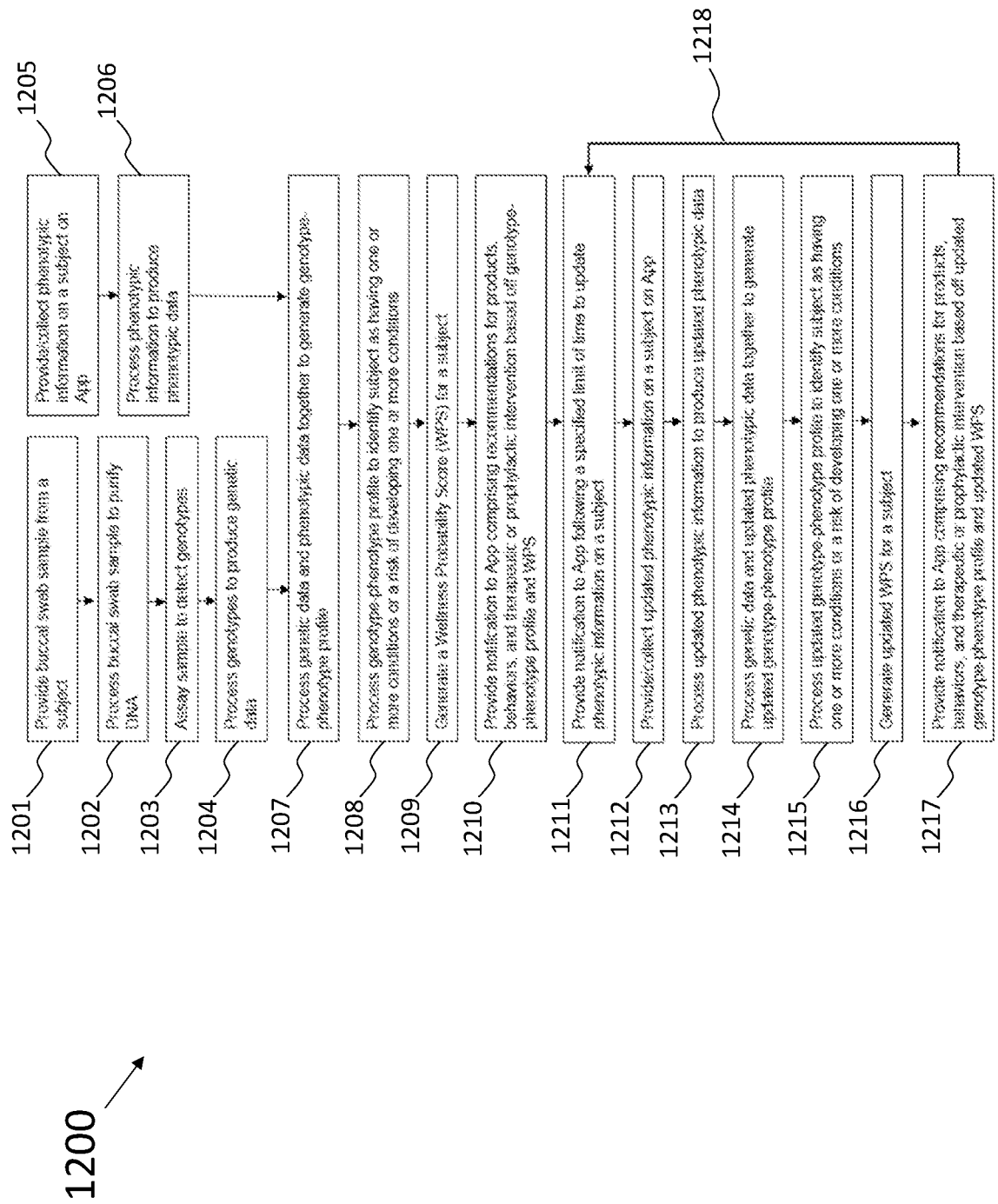
FIG. 12 shows a non-limiting workflow according to an embodiment of the present disclosure for processing a biological sample obtained from a non-human subject to generate a genotype-phenotype profile to identify a non-human subject as having one or more conditions or a risk of developing one or more conditions and a wellness probability score (WPS), and subsequently provide recommendations for products, behaviors, and therapeutic or prophylactic intervention based off the genotype-phenotype profile and the WPS.

A non-limiting example of a method of the present disclosure is illustrated in FIG. 12. Referring to FIG. 12, methods disclosed herein can provide a personalized wellness system 1200. The genetic data 1204 can be generated following sample collection 1201, DNA isolation 1202, and genotyping assays 1203. The phenotypic data 1206 can be generated from phenotypic information provided on an App 1205. Together the genetic data 1204 and phenotypic data 1206 can be processed together to generate a genotype-phenotype profile 1207. The genotype-phenotype profile 1207 can be processed to identify the subject as having one or more condition or a risk of developing the one or more conditions 1208. The genotype-phenotype profile 1207 and the risk assessment 1208 can be used, at least in part, to develop a wellness probability score (WPS) 1209. The WPS can be calculated using a machine learning model disclosed elsewhere herein. Based off the genotype-phenotype profile 1207 and the WPS 1209 a notification can be provided through an App comprising recommendations for products, behaviors, and interventions 1210. After a period of time another notification can be provided through the App comprising a reminder to provide updated information 1211. Once the updated information is collected in the App 1212, the updated information 1211 can be processed to produce the updated data 1213. An updated genotype-phenotype profile 1214 can be generated from the new data and can be used on a new risk assessment 1215 and can be used to generate an updated WPS 1216. Based off the updated genotype-phenotype profile 1214 and the updated WPS 1216 a new notification can be provided through the App 1217 comprising recommendations for products, behaviors, and interventions 1217. The collection, processing, and updating of information and data can be continued throughout use of the personalized wellness system 1218.

Methods of Detection

Described herein are methods for determining a presence or a level of one or more biomarkers in a subject (e.g., animal or non-human subject). In some embodiments, the one or more biomarkers is a genotype (e.g., genetic variants), a ribonucleic acid (RNA), a protein, a metabolite, a sugar, a lipid, a hormone, a vitamin, a cell, an electrolyte, and/or a mineral. In some embodiments, the methods disclosed herein comprise measuring a presence or an absence of the one or more biomarkers, such as for example, an allele associated with an incidence of a particular phenotype disclosed herein (case v. control). In some embodiments, the methods disclosed herein comprise measuring a level of the one or more biomarkers and comparing that level with a control level of the one or more biomarkers. In some embodiments, the control level is obtained from the subject at a different time point in a longitudinal analysis. In some embodiments, the control level of the one or more biomarkers is obtained from a healthy (or non-diseased) subject. In some embodiments, the control level of the one or more biomarkers is obtained from a subject has the phenotype, but does not have the one or more biomarker of interest. In some embodiments, the control level is an index obtained from a group of control subjects.

Methods disclosed herein are generally suitable for analyzing a sample obtained from a subject. Similarly, methods disclosed herein comprises processing and/or analysis of the sample. In some embodiments, the sample is obtained directly, or indirectly, from the subject. In some embodiments, the sample is obtained by a fluid draw, swab, fluid collection, or biopsy. In some embodiments, the sample comprises whole blood, peripheral blood, plasma, serum, saliva, cheek swab, urine, feces, hair roots or other bodily fluid or tissue. In some embodiments, the sample is analyzed from a biopsy. In some embodiments, the biopsy is from a tumor. In some embodiments, the biopsy is from a growth. In some embodiments, the tissue biopsy is from an organ.

Non-limiting examples of organs include muscles, skin, liver, kidney, intestinal tract, stomach, pancreas, and lungs. In some embodiments, the sample is analyzed from feces. In some embodiments, the sample is analyzed from blood. In some embodiments, the sample is analyzed from urine. In some embodiments, the blood and/or urine sample from the subject is analyzed after fasting. In some embodiments, the subject fasts for a range of about 8 hours to about 16 hours. In some embodiments, the subject fasts for a range of about 10 hours to about 14 hours. In some embodiments, the subject fasts for about 12 hours. In some embodiments, the guardian of the subject obtains the sample of the subject and provides the sample to a laboratory for processing and analysis. In some embodiments, a veterinarian obtains the sample of the subject and provides the sample to a laboratory for processing and analysis.

Subjects

Provided herein are subjects in need of a personalized wellness system according to various embodiments disclosed herein. In some embodiments, the subject is an animal. In some embodiments, the subject is non-human. In some embodiments, the subject is a mammal. Non-limiting examples of mammals include non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In some embodiments, the subject is a reptile. Non-limiting examples of reptiles include birds, snakes, lizards, and turtles. In some embodiments, the subject is an amphibian. Non-limiting examples of amphibians include frogs, toads, salamanders, and newts. In some embodiments, the subject is a marsupial. Non-limiting examples of marsupials include sugar gliders, crest-tailed marsupial mice, kangaroos, and opossums. In some embodiments, a non-human subject is a camelid such as an alpaca, llama, or camel. In some embodiments, the camelid is used for producing therapeutics. In some embodiments, the camelid is used for wool production. In some embodiments, a subject is a pet. In some embodiments, the subject is known to have one or more conditions. In some embodiments, the subject is known to be at risk of developing one or more conditions. In some embodiments, the subject does not have a known condition. In some embodiments, the subject does not have a known risk of developing a condition. In some embodiments, the subject is suspected of having one or more conditions. In some embodiments, the subject is suspected of being at risk of developing one or more conditions.

Genotype

Provided herein are genotypes associated with a high or a low likelihood of having or developing a disease or a condition disclosed herein relative to one or more control subjects. In some embodiments, the genotypes comprise one or more genetic variants. In some embodiments, the one or more genetic variants comprises a single nucleotide polymorphism (SNP), an insertion or deletion (indels) of one or more nucleotides, or a copy-number variant (CNV). In some embodiments, the SNP, the indel, or the CNV may fall within coding regions of a gene, a non-coding region of a gene, or in an intergenic region between genes. In some embodiments, the genotype is associated with dilated cardiomyopathy, Imerslund-Grasbeck Syndrome, Factor VII deficiency, epilepsy, diabetes, behavioral traits, hip dysplasia, hyperthyroidism, hypercalcemia, feline eosinophilic keratoconjunctivitis, inflammatory bowel disease, or hypertrophic cardiomyopathy as a few non-limiting examples. In some embodiments, the genotypes associated with the disease or the condition with a p-value of less than 0.05. In some embodiments, the p-value is at most about $1.0 \times 10^{-6}$, about $1.0 \times 10^{-7}$, about $1.0 \times 10^{-8}$, about $1.0 \times 10^{-9}$, about $1.0 \times 10^{-10}$, about $1.0 \times 10^{-20}$, about $1.0 \times 10^{-30}$, about $1.0 \times 10^{-40}$, about $1.0 \times 10^{-50}$, about $1.0 \times 10^{-60}$, about $1.0 \times 10^{-70}$, about $1.0 \times 10^{-80}$, about $1.0 \times 10^{-90}$, or about $1.0 \times 10^{-100}$.

Disclosed herein are methods of detecting one or more genotypes of a subject (e.g., non-human subject or animal). In some embodiments, methods comprise analyzing a sample obtained from the subject. In some embodiments, genetic material is extracted from the sample obtained from the subject. In some embodiments, the genetic material comprises a denatured DNA molecule or fragment thereof. In some embodiments, the genetic material comprises DNA selected from: genomic DNA, viral DNA, mitochondrial DNA, plasmid DNA, amplified DNA, circular DNA, circulating DNA, cell-free DNA, or exosomal DNA. In some embodiments, the DNA is single-stranded DNA (ssDNA), double-stranded DNA, denaturing double-stranded DNA, synthetic DNA, and combinations thereof. The circular DNA may be cleaved or fragmented.

In some embodiments, genetic variants are detected in the genetic material from the sample obtained from a subject using a nucleic acid-based detection assay (e.g., genotyping array, quantitative polymerase chain reaction (qPCR), whole genome sequencing, skim sequencing, and/or fluorogenic qPCR). In some embodiments, the nucleic acid-based detection assay comprises qPCR, gel electrophoresis (including for e.g., Northern or Southern blot), immunochemistry, in situ hybridization such as fluorescent in situ hybridization (FISH), cytochemistry, or sequencing. In some embodiments, the sequencing technique comprises next generation sequencing. In some embodiments, the methods involve a hybridization assay such as fluorogenic qPCR (e.g., TaqMan™ or SYBR green), which involves a nucleic acid amplification reaction with a specific primer pair, and hybridization of the amplified nucleic acid probes comprising a detectable moiety or molecule that is specific to a target nucleic acid sequence. An additional exemplary nucleic acid-based detection assay comprises the use of nucleic acid probes conjugated or otherwise immobilized on a bead, multi-well plate, array, or other substrate, wherein the nucleic acid probes are configured to hybridize with a target nucleic acid sequence. In some embodiments, the nucleic acid probe is specific to a genetic variant (e.g., SNP or indel) is used. In some embodiments, the nucleic acid probe specific to a SNP comprises a nucleic acid probe sequence sufficiently complementary to a risk or protective allele of interest, such that hybridization is specific to the risk or protective allele. In some embodiments, the nucleic acid probe specific to an indel comprises a nucleic acid probe sequence sufficiently complementary to an insertion of a nucleobase within a polynucleotide sequence flanking the insertion, such that hybridization is specific to the indel. In some embodiments, the nucleic acid probe specific to an indel comprises a probe sequence sufficiently complementary to a polynucleotide sequence flanking a deletion of a nucleobase within the polynucleotide sequence, such that hybridization is specific to the indel. In some embodiments, a plurality of nucleic acid probes are required to detect a CNV, specific to various regions within a polynucleotide sequence comprising the CNV. In a non-limiting example, a plurality of nucleic acid probes specific to a single exon CNV within a gene may comprise a high-density of between 2 and 3, 3 and 4, 4 and 5, 5 and 6, and 6 and 7 nucleic acid probes, each nucleic acid probe sufficiently complementary to exonic regions of the gene may be used. In another non-limiting example, long CNVs may be detected utilizing a plurality of nucleic acid probes dispersed throughout the genome of the individual.

In some embodiments, the DNA analyzed may be autosomal DNA. In some embodiments, the DNA analyzed may have a known pattern of inheritance. In some embodiments, the DNA analyzed may be for genes and correspond to being recessive or dominant. In some embodiments, the DNA analyzed may be from a tumor. In some embodiments, the DNA analyzed may be cell-free DNA. In some embodiments, the cell-free DNA is from a tumor. In some embodiments, the DNA analyzed from the tumor comprises utilization for diagnosis, prognosis, recurrence monitoring, or any combination thereof. In some embodiments, the DNA analyzed is from microbes. In some embodiments, the microbes comprise the microbiota of a subject. In some embodiments, the microbiota is for the entire subject. In some embodiments, the microbiota is for a specific area of the subject. In some embodiments, the microbiota is specific to the gut of a subject. In some embodiments, the microbiota is specific to the skin of a subject. In some embodiments, the microbiota are specific to the mouth of a subject. Non-limiting area for collection for analysis of the microbiota include skin, mouth, and feces. In some embodiments, the DNA being analyzed is epigenetic DNA. In some embodiments, the epigenetic DNA is analyzed to determine a subject's age. In some embodiments, the epigenetic DNA is analyzed to determine a subject's genetic age. In some embodiments, the epigenetic DNA is analyzed to determine environmental effects of the subject. In some embodiments, the disease associated variants associated with a disease or condition in a canine subject disclosed herein are provided in "Genetic prevalence and clinical relevance of canine Mendelian disease variants in over one million dogs," Donner J, Freyer, et al. (2023) Genetic prevalence and clinical relevance of canine Mendelian disease variants in over one million dogs. PLOS Genetics 19(2): e1010651, which is here by incorporated by reference in its entirety.

In some embodiments, the nucleic acid-based assay comprises a nucleic acid amplification assay. In some embodiments, the amplification assay comprises qPCR, self-sustained sequence replication, transcriptional amplification system, Q-Beta Replicase, rolling circle replication, or any suitable other nucleic acid amplification technique. A suitable nucleic acid amplification technique is configured to amplify a region of a nucleic acid sequence comprising the risk variant (e.g., SNP, CNV, or indel). In some embodiments, the amplification assays require primers. The known nucleic acid sequence for the genes, or genetic variants, within the genotype is sufficient to enable one of skill in the art to select primers to amplify any portion of the gene or genetic variants. A DNA sample suitable as a primer may be obtained, e.g., by polymerase chain reaction (PCR) amplification of genomic DNA, fragments of genomic DNA, fragments of genomic DNA ligated to adaptor sequences or cloned sequences. Any suitable computer program can be used to design primers with the desired specificity and optimal amplification properties, such as PrimerQuest (IDT).

In some embodiments, detecting the presence or absence of a genotype comprises sequencing genetic material from a sample obtained from the subject. In some embodiments, the sequence comprises whole genome sequencing or skim sequencing. Sequencing can be performed with any appropriate sequencing technology, including but not limited to single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis. Sequencing methods also include next-generation sequencing, e.g., modern sequencing technologies such as Illumina sequencing (e.g., Solexa), Roche 454 sequencing, Ion Torrent sequencing, PacBio sequencing, and SOLiD sequencing. In some cases, next-generation sequencing involves high-throughput sequencing methods. Additional sequencing methods available to one of skill in the art may also be employed.

RNA

Provided herein are biomarkers comprising RNA that are associated with a high or a low likelihood of having or developing a disease or a condition disclosed herein relative to one or more control subjects (e.g., non-human subject or animal). In some embodiments, the level of the RNA is associated with atopic dermatitis. In some embodiments, the level of the RNA is an expression level. In some embodiments, the RNA comprises miR-203. In some embodiments, the level of the RNA is associated with cancer. For In some embodiments, reduced expression of miR-1 and miR-133b may be indicative of osteosarcoma(s). In some embodiments, increased expression of miR-214 or miR-126 mat be indicative of a variety of cancers. Non-limiting examples of these cancers include thyroid carcinoma, mammary carcinoma, osteosarcoma, histiocytic sarcoma, chondrosarcoma, hemangiosarcoma, hepatocellular carcinoma, squamous cell carcinoma, transitional cell carcinoma, adenocarcinoma, mast cell tumor, and melanoma. In some embodiments, the level of the RNA is associated with heart disease. In some embodiments, increased expression of FN1 And ETV7 being linked with heart disease.

Described herein are methods for determining a presence or a level of expression of a ribonucleic acid (RNA) of a subject. In some embodiments, genetic material is extracted from the sample obtained from the non-human subject. In some embodiments, the RNA comprises fragmented RNA. In some embodiments, the RNA comprises partially degraded RNA. In some embodiments, the RNA comprises a microRNA or portion thereof. In some embodiments, the RNA comprises an RNA molecule or a fragmented RNA molecule (RNA fragments) selected from: a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, an RNA transcript, a synthetic RNA, and combinations thereof. In some embodiments, the presence or level of expression of RNA of a non-human subject comprises quantitative polymerase chain reaction (qPCR), gel electrophoresis (including for e.g., Northern blot), immunochemistry, in situ hybridization such as fluorescent in situ hybridization (FISH), cytochemistry, or sequencing. In some embodiments, the sequencing technique comprises next generation sequencing. In some embodiments, the methods involve a hybridization assay such as fluorogenic qPCR (e.g., TaqMan™ or SYBR green), which involves a nucleic acid amplification reaction with a specific primer pair, and hybridization of the amplified nucleic acid probes comprising a detectable moiety or molecule that is specific to a target nucleic acid sequence. An additional exemplary nucleic acid-based detection assay comprises the use of nucleic acid probes conjugated or otherwise immobilized on a bead, multi-well plate, array, or other substrate, wherein the nucleic acid probes are configured to hybridize with a target nucleic acid sequence.

Protein

Provided herein are biomarkers comprising a protein that is associated with a high or a low likelihood of having or developing a disease or a condition disclosed herein relative to one or more control subjects. In some embodiments, a protein disclosed herein may be used to assess a high or a low likelihood of having or developing a disease or a condition disclosed herein relative to one or more control subjects.

In some embodiments, the protein is an enzyme. In some embodiments, the enzyme comprises lipase, amylase or gamma-glutamyl transpeptidase. In some embodiments, the protein is an antibody or antigen-binding fragment thereof. In some embodiments, the antibody or antigen binding fragment comprises a neutralizing antibody, immunoglobulin E, immunoglobulin G, immunoglobulin A, immunoglobulin D, immunoglobulin M, or a combination thereof. In some embodiments, the one or more serological markers comprises anti-*Saccharomyces cerevisiae* antibody (ASCA), an anti-neutrophil cytoplasmic antibody (ANCA), antibody against *E. coli* outer membrane porin protein C (anti-OmpC), anti-chitin antibody, pANCA antibody, anti-I2 antibody, and anti-Cbir1 flagellin antibody. In some embodiments, the antibody or antigen-binding fragment comprises a therapeutic agent disclosed herein. In some embodiments, the protein is a fibrous protein. In some embodiments, the fibrous protein comprises albumin, keratin, insulin, or collagen.

In some embodiments, the level of the protein is associated with hip dysplasia. In some embodiments, the level of the protein is an expression level. In some embodiments, the level of the protein is an activity level. In some embodiments, the level of the protein is a concentration of the protein. In some embodiments, the level is compared with a control level of the protein in one or more control subjects. In some embodiments, the level of the protein is decreased as compared to a control level. In some embodiments, the level of the protein is increased as compared to a control level. In some embodiments, the control level is obtained from a control subject that does not have hip dysplasia. In some embodiments, the protein comprises C-telopeptide of type I collagen (CTX-I), C-telopeptide of type II collagen (CTX-II), tissue inhibitor of metalloproteases 1 (TIMP-1), matrix metalloproteinase 9 (MMP-9), or C-propeptide of type II procollagen (PIICP), collagen type II cleavage (CIIC), keratan sulfate (KS), prostaglandin E2 (PGE2), or any combination thereof. In some embodiments, the PIICP is detected from serum. In some embodiments, the PIICP is detected from plasma. In some embodiments, the level of PIICP is between about 25 and about 10 ng/mL. In some embodiments, the level of PIICP is between about 22 and about 12 ng/mL. In some embodiments, the level of PIICP is between about 20 and about 14 ng/mL. In some embodiments, the level of PIICP is between about 18 and about 15 ng/mL. In some embodiments, the level of PIICP is between about 17 and about 16 ng/mL. In some embodiments, the CIIC is detected from plasma. In some embodiments, the level of CIIC is between about 160 and about 60 ng/mL. In some embodiments, the level of CIIC is between about 150 and about 80 ng/mL. In some embodiments, the level of CIIC is between about 140 and about 100 ng/mL. In some embodiments, the level of CIIC is between about 130 and about 120 ng/mL. In some embodiments, the level of CIIC is between about 130 and about 125 ng/mL. In some embodiments, the KS is detected from plasma. In some embodiments, the level of KS is between about 80 and about 60 ng/mL. In some embodiments, the level of KS is between about 70 and about 65 ng/mL. In some embodiments, the PGE2 is detected from plasma. In some embodiments, the level of PGE2 is between about 100 and about 400 µg/mL. In some embodiments, the level of PGE2 is between about 150 and about 300 µg/mL. In some embodiments, the level of PGE2 is between about 200 and about 250 µg/mL. In some embodiments, the biomarkers associated with hip dysplasia are detected in a sample obtained from the subject, such as a blood serum, blood plasma, or urine.

In some embodiments, the level of the protein is associated with diabetes. In some embodiments, the level of the protein is an expression level. In some embodiments, the level of the protein is an activity level. In some embodiments, the level is compared with a control level of the protein in one or more control subjects. In some embodiments, the level of the protein is decreased as compared to a control level. In some embodiments, the level of the protein is increased as compared to a control level. In some embodiments, the control level is obtained from a control subject that does not have diabetes. In some embodiments, the protein comprises SRC kinase signaling inhibitor 1 (SRCIN1), phosphatidylinositol-4 kinase type 2 alpha (PI4KIIα), Pro-melanin concentrating hormone (Pro-MCH), Flotillin-1, Protein mono-ADP ribosyltransferase, GRIP and coiled coil domain containing protein 2, tetratricopeptide repeat protein 36, serpin, alanine aminotransferase (ALT), alkaline phosphatase (ALP), aspartate aminotransferase (AST) and Prelamin A/C, or any combination thereof. In some embodiments, the ALT is greater than about 109 U/L. In some embodiments, the ALP is greater than about 114 U/L. In some embodiments, the AST is greater than about 15 U/L. In some embodiments, the biomarkers associated with diabetes are detected in a sample obtained from the subject, such as a blood serum, blood plasma, tear film, or urine.

In some embodiments, the level of the protein is associated with atopic dermatitis. In some embodiments, the level of the protein is an expression level. In some embodiments, the level of the protein is an activity level. In some embodiments, the level of the protein is a concentration of the protein. In some embodiments, the level is compared with a control level of the protein in one or more control subjects. In some embodiments, the level of the protein is decreased as compared to a control level. In some embodiments, the level of the protein is increased as compared to a control level. In some embodiments, the control level is obtained from a control subject that does not have atopic dermatitis. In some embodiments, the protein comprises thymus and activation-regulated chemokine (TARC) (also known as C—C chemokine ligand 17 (CCL17)), C—C—C chemokine ligand 22 (CCL22), C—C chemokine ligand 28 (CCL28), protein inhibitor of activated stat 1 (PIAS1), retinoic acid receptor (RAR)-related orphan receptor alpha (RORA), SH2B adaptor protein 1 (SH2B1), interleukin 34 (IL-34), interleukin 31 (IL-31), Macrophage migration inhibitory factor (MIF) and phosphodiesterase 4D (PDE4D), or any combination thereof.

In some embodiments, the level of the protein is associated with thyroid function. In some embodiments, the level of the protein is an expression level. In some embodiments, the level of the protein is an activity level. In some embodiments, the level of the protein is a concentration of the protein. In some embodiments, the level of the protein is in a ratio to other proteins. In some embodiments, the level is compared with a control level of the protein in one or more control subjects. In some embodiments, the level of the protein is decreased as compared to a control level. In some embodiments, the level of the protein is increased as compared to a control level. In some embodiments, the control level is obtained from a control subject that does not have thyroid dysfunction. In some embodiments, the protein comprises thiobarbituric acid reactive substances (TBARS).

In some embodiments, the protein comprises lipase. High levels of lipase in the blood could indicate a bowel obstruction, pancreatic cancer, kidney failure, or one of several other conditions. In some embodiments, the protein comprises amylase. High levels of amylase could indicate a problem with the pancreas, such as for example, pancreatitis. Low levels of amylase could indicate liver or kidney problems, or one of several other conditions. In some embodiments, the protein comprises gamma-glutamyl transpeptidase. High levels of gamma-glutamyl transpeptidase could indicate liver problems. In some embodiments, the protein comprises albumin. Low albumin levels could indicate liver or kidney problems. High albumin levels could indicate dehydration. In some embodiments, the protein comprises globulin. High levels of globulin could indicate an autoimmune disease, an infection, or cancer. Described herein are methods for determining a presence or a level of a protein in a subject (e.g., animal or non-human subject). In some embodiments, multiple proteins are analyzed. In some embodiments, the multiple proteins analyzed are for a single condition or disease. In some embodiments, the multiple proteins analyzed are for multiple conditions or diseases. In some embodiments, different proteins from different sample types are used to assess a high or a low likelihood of having or developing a disease or a condition disclosed herein relative to one or more control subjects. In some embodiments, the protein is analyzed using an immunoassay. Non-limiting examples of types of immunoassays include immunohistochemistry, radioimmunoassay, enzyme immunoassay such as enzyme-linked immunosorbent assay (ELISA), fluoroimmunoassay, chemiluminescence immunoassay, immunonephelometry, dipstick-based immunoassay, and immunoturbidimetry. In some embodiments, greater than or equal to one protein is analyzed. In some embodiments, greater than or equal to 2, 3, 4, 5, 6, 7, 8, 9, or 10 proteins are analyzed. In some embodiments, from about 1 to about 10, about 2 to about 9, about 3 to about 8, about 4 to about 7, or about 5 to about 6 proteins are analyzed.

Metabolite

Provided herein are biomarkers comprising a metabolite that is associated with a high or a low likelihood of having or developing a disease or a condition disclosed herein relative to one or more control subjects. Non-limiting examples of metabolites being assessed include urea nitrogen, ketones, creatinine, and amino acids (e.g., arginine, histidine, methionine, valine, and taurine).

In some embodiments, the level of the metabolite is associated with hip dysplasia. In some embodiments, the level is compared with a control level of the protein in one or more control subjects. In some embodiments, the biomarkers associated with hip dysplasia are detected in a sample obtained from the subject, such as a blood serum or urine.

In some embodiments, the level of the metabolite is associated with diabetes. In some embodiments, the level is compared with a control level of the protein in one or more control subjects. In some embodiments, the metabolite comprises picolinic acid, indoxyl sulfate, anthranilate, or any combination thereof. In some embodiments, the biomarkers associated with diabetes are detected in a sample obtained from the subject, such as a blood serum or urine.

In some embodiments, the level of the metabolite is associated with atopic dermatitis. In some embodiments, the level is compared with a control level of the protein in one or more control subjects. In some embodiments, the metabolite comprises picolinic acid, indoxyl sulfate, anthranilate, or any combination thereof. In some embodiments, the biomarkers associated with atopic dermatitis are detected in a sample obtained from the subject, such as a blood serum or urine.

In some embodiments, the level of the metabolite is associated with thyroid function. In some embodiments, the level is compared with a control level of the protein in one or more control subjects. In some embodiments, the metabolite comprises picolinic acid, indoxyl sulfate, anthranilate, or any combination thereof. In some embodiments, the metabolite associated with thyroid function is detected in blood plasma, blood serum, saliva, or urine.

In some embodiments, the metabolite comprises urea nitrogen. Urea nitrogen levels can indicate kidney performance. In some embodiments, the metabolite comprises ketones. The presence of ketones can indicate uncontrolled diabetes or starvation. In some embodiments, the metabolite comprises creatinine. Creatinine levels can indicate kidney performance. In some embodiments, the metabolite comprises an amino acid (e.g., arginine, histidine, methionine, valine, and taurine). In some embodiments, the amino acid comprises taurine. Low levels of taurine have been linked to dilated cardiomyopathy in dogs. In some embodiments, the metabolite comprises symmetric dimethylarginine (SDMA). In some embodiments, the level of SDMA is increased as compared to a control. In some embodiments, the level of SDMA is indicative of reduced renal function. In some embodiments, the level of SDMA is above about 14 µg/dl. Described herein are methods for determining a presence or a level of a metabolite in a subject (e.g., animal or non-human subject). In some embodiments, multiple metabolites are analyzed. In some embodiments, the multiple metabolites analyzed are for a single condition or disease. In some embodiments, the multiple metabolites analyzed are for multiple conditions or diseases. In some embodiments, different metabolites from different sample types are used to assess a high or a low likelihood of having or developing a disease or a condition disclosed herein relative to one or more control subjects. In some embodiments, the metabolite is analyzed using instrumentation. In some embodiments, the instrumentation is chromatography. In some embodiments, the chromatography is liquid chromatography or gas chromatography. In some embodiments, the chromatography is followed by mass spectrometry (MS). In some embodiments, MS-MS is performed. In some embodiments, the metabolite is detected using an immunoassay. Non-limiting examples of types of immunoassays include radioimmunoassay, enzyme immunoassay such as enzyme-linked immunosorbent assay (ELISA), fluoroimmunoassay, chemiluminescence immunoassay, immunonephelometry, dipstick-based immunoassay, and immunoturbidimetry. In some embodiments, the metabolite is detected using cupric reducing antioxidant capacity (CUPRAC). In some embodiments, the metabolite is detected using ferrous oxidation-xylenol orange (FOX). In some embodiments, the metabolite is detected using ferric reducing ability of the plasma (FRAP). In some embodiments, the metabolite is detected using trolox equivalent antioxidant capacity (TEAC). In some embodiments, greater than or equal to one metabolite is analyzed. In some embodiments, greater than or equal to 2, 3, 4, 5, 6, 7, 8, 9, or 10 metabolites are analyzed. In some embodiments, from about 1 to about 10, about 2 to about 9, about 3 to about 8, about 4 to about 7, or about 5 to about 6 metabolites are analyzed.

Sugar

Provided herein are biomarkers comprising a sugar that is associated with a high or a low likelihood of having or developing a disease or a condition disclosed herein relative to one or more control subjects. In some embodiments, the sugar comprises glucose. Glucose levels can indicate diabetes. Generally, if glucose levels are high, the pancreas is not producing insulin, the pancreas is not making enough insulin, or the subject has become insulin resistant. In some embodiments, the glucose is greater than about 119 mg/dL. In some embodiments, the sugar is fructosamine. In some embodiments, the level of fructosamine is greater than about 320 µmol/L. In some embodiments, the level of fructosamine is less than about 850 µmol/L. In some embodiments, the level of fructosamine is between about 320 to about 850 µmol/L. In some embodiments, the sugar comprise glucose, fructosamine, keto-hexose, deoxy-hexose, or any combination thereof. In some embodiments, the amount of glucose that is stuck to hemoglobin cells is measured. In some embodiments, the biomarkers associated with diabetes are detected in a sample obtained from the subject, such as a blood serum, blood plasma, tear film, or urine. Described herein are methods for determining a presence or a level of a sugar in a subject (e.g., animal or non-human subject). In some embodiments, multiple sugars are analyzed. In some embodiments, the multiple sugars analyzed are for a single condition or disease. In some embodiments, the multiple sugars analyzed are for multiple conditions or diseases. In some embodiments, different sugars from different sample types are used to assess a high or a low likelihood of having or developing a disease or a condition disclosed herein relative to one or more control subjects. In some embodiments, the sugar is analyzed using an electrical current. In some embodiments, the level of the sugar is determined through an enzyme reaction. In some embodiments, the level of the sugar is determined through two sequential enzyme reactions. In some embodiments, the product of the enzyme reaction(s) is measured by photometrically. In some embodiments, the product of the enzyme reaction(s) is measured amperometrically and photometrically. Non-limiting examples of sugars being assessed include glucose. In some embodiments, greater than or equal to one sugar is analyzed. In some embodiments, greater than or equal to 2, 3, 4, 5, 6, 7, 8, 9, or 10 sugars are analyzed. In some embodiments, from about 1 to about 10, about 2 to about 9, about 3 to about 8, about 4 to about 7, or about 5 to about 6 sugars are analyzed.

Lipid

Provided herein are biomarkers comprising a lipid that is associated with a high or a low likelihood of having or developing a disease or a condition disclosed herein relative to one or more control subjects. In some embodiments, a lipid disclosed herein may be used to assess a high or a low likelihood of having or developing a disease or a condition disclosed herein relative to one or more control subjects. Non-limiting examples of lipids analyzed includes cholesterol, cholesterol esters, triglycerides, free fatty acids, phosphatidylcholine, phosphatidylethanolamine, phosphatidylserine, phospholipids, and sphingolipids.

In some embodiments, the lipid comprises cholesterol. High levels of cholesterol can lead to heart disease. In some embodiments, the lipid comprises a triglyceride. High levels of triglyceride can lead to heart disease. In some embodiments, the lipid is associated with atopic dermatitis. In some embodiments, the lipid comprises paraoxonase-1 (PON1). In some embodiments, the lipid is associated with diabetes. In some embodiments the lipid comprises lysophosphatidylethanolamine. Described herein are methods for determining a presence or a level of a lipid in a subject (e.g., animal or non-human subject). In some embodiments, multiple lipids are analyzed. In some embodiments, the multiple lipids analyzed are for a single condition or disease. In some embodiments, the multiple lipids analyzed are for multiple conditions or diseases. In some embodiments, different lipids from different sample types are used to assess a high or a low likelihood of having or developing a disease or a condition disclosed herein relative to one or more control subjects. In some embodiments, the lipid is analyzed using chromatography. Non-limiting examples of chromatography include thin layer chromatography, glass paper chromatography, gas chromatography, and liquid chromatography. In some embodiments, the lipid is analyzed using mass spectrometry (MS). In some embodiments, the lipid is analyzed using MS-MS. In some embodiments, the lipid is analyzed using chromatography and MS. In some embodiments, the lipid is analyzed using chromatography and MS-MS. In some embodiments, the lipid is analyzed through an enzyme reaction. In some embodiments, the lipid is analyzed through two enzyme reactions. In some embodiments, the lipid is analyzed through three enzyme reactions. In some embodiments, the enzyme reactions are sequential. In some reactions the lipid is analyzed fluorometrically. In some embodiments, the enzyme reaction product is measured fluorometrically. In some embodiments, the lipid is analyzed calorimetrically. In some embodiments, the enzyme reaction product is measured calorimetrically. In some embodiments, greater than or equal to one lipid is analyzed. In some embodiments, greater than or equal to 2, 3, 4, 5, 6, 7, 8, 9, or 10 lipids are analyzed. In some embodiments, from about 1 to about 10, about 2 to about 9, about 3 to about 8, about 4 to about 7, or about 5 to about 6 lipids are analyzed.

Hormone

Provided herein are biomarkers comprising a hormone that is associated with a high or a low likelihood of having or developing a disease or a condition disclosed herein relative to one or more control subjects. In some embodiments, a hormone disclosed herein may be used to assess a high or a low likelihood of having or developing a disease or a condition disclosed herein relative to one or more control subjects. Non-limiting examples of hormones include cortisol, triiodothyronine, thyroxine, thyroid stimulating hormone, adrenocorticotropic hormone, and androgens/estrogens.

In some embodiments, the hormone comprises cortisol. High or low levels of cortisol can indicate an adrenal gland disorder. Adrenal gland disorders are common in dogs with the most prevalent disorder, Cushing's disease, resulting in the overproduction of cortisol. In some embodiments, the hormones are associated with diabetes. In some embodiments, the hormones include leptin, insulin, or any combination thereof. In some embodiments, the hormone is associated with neoplasia. In some embodiments, the hormone includes estradiol, progesterone, 17-hydroxyprogesterone, testosterone, androstenedione, or any combination thereof. In some embodiments, the level of estradiol is greater than about 25 µg/mL. In some embodiments, the level of estradiol is less than about 55 µg/mL. In some embodiments, the level of estradiol is between about 25 to about 55 µg/mL. In some embodiments, the level of progesterone is greater than about 0.2 ng/mL. In some embodiments, the level of progesterone is greater than about 0.4 ng/mL. In some embodiments, the level of progesterone is less than about 1.1 ng/mL. In some embodiments, the level of progesterone is less than about 0.2 ng/mL. In some embodiments, the level of progesterone is between about 0.4 to about 1.1 ng/mL. In some embodiments, the level of progesterone is between about 0.2 to about 1.1 ng/mL. In some embodiments, the level of progesterone is between about 0 and about 0.2 ng/mL. In some embodiments, the level of 17-hydroxyprogesterone is greater than about 0.4 ng/mL. In some embodiments, the level of 17-hydroxyprogesterone is greater than about 0.5 ng/mL. In some embodiments, the level of 17-hydroxyprogesterone is less than about 1.5 ng/mL. In some embodiments, the level of 17-hydroxyprogesterone is less than about 0.4 ng/mL. In some embodiments, the level of 17-hydroxyprogesterone is between about 0.5 to about 1.5 ng/mL. In some embodiments, the level of progesterone is between about 0.4 to about 1.5 ng/mL. In some embodiments, the level of progesterone is between about 0 and about 0.4 ng/mL. In some embodiments, the level of testosterone is less than about 15 ng/mL. In some embodiments, the level of testosterone is less than about 24 ng/mL. In some embodiments, the level of testosterone is less than about 42 ng/mL. In some embodiments, the level of testosterone is less than about 15 to about 42 ng/mL. In some embodiments, the level of testosterone is less than about 15 to about 24 ng/mL. In some embodiments, the level of testosterone is between about 0 to about 42 ng/mL. In some embodiments, the level if testosterone is between about 15 to about 24 ng/mL. In some embodiments, the level of androstenedione is less than about 3 ng/mL. In some embodiments, the level of androstenedione is greater than about 0.05 ng/mL. In some embodiments, the level of androstenedione less than about 0.36 ng/mL. In some embodiments, the level of androstenedione is greater than about 0.24 ng/mL. In some embodiments, the level of androstenedione is between about 0.05 and about 2.90 ng/mL. In some embodiments, the level of androstenedione is between about 0.05 and about 0.36 ng/mL. The level of androstenedione is between about 0.24 and about 2.90 ng/mL.

In some embodiments, the hormone comprises a thyroid hormone. In some embodiments, the thyroid hormone comprises triiodothyronine, thyroxine, thyroid stimulating hormone, or any combination thereof. Levels of thyroid hormones outside the normal range can indicate a thyroid condition, such as hyperthyroidism. In some embodiments, the thyroid condition is hypothyroidism. Hormones associated with hypothyroidism comprise thyrotropin, thyroxine (free or total), triiodothyronine, leptin, and insulin. In some embodiments, the level of triiodothyronine is less than about 45 nmol/L. In some embodiments, the level of thyroxine is less than about 19 nmol/L. In some embodiments, the level of thyroxine is less than about 14 nmol/L. In some embodiments, the level of thyroxine is less than about 12 nmol/L. In some embodiments, the level of thyroxine is less than about 10 nmol/L. In some embodiments, the level of thyrotropin is greater than about 0.5 ng/L. In some embodiments, the thyroid condition is hyperthyroidism. Hormones associated with hyperthyroidism comprise thyrotropin, thyroxine (free or total), and triiodothyronine. In some embodiments, the level of triiodothyronine is greater than about 150 nmol/L. In some embodiments, the level of thyroxine is greater than about 45 nmol/L. In some embodiments, the level of thyroxine is greater than about 50 nmol/L. In some embodiments, the hormone comprises a sex hormone. In some embodiments, the sex hormone is an androgen or an estrogen. Increased levels of sex hormones can indicate tumors on sex organs (e.g., testes or ovaries). In some embodiments, the sex hormones are monitored for fertility or pregnancy in the subject.

Described herein are methods for determining a presence or a level of a hormone in a subject (e.g., animal or non-human subject). In some embodiments, multiple hormones are analyzed. In some embodiments, the multiple hormones analyzed are for a single condition or disease. In some embodiments, the multiple hormones analyzed are for multiple conditions or diseases. In some embodiments, different hormones from different sample types are used to assess a high or a low likelihood of having or developing a disease or a condition disclosed herein relative to one or more control subjects. In some embodiments, the hormone is analyzed with an immunoassay. Non-limiting examples of types of immunoassays include immunohistochemistry, radioimmunoassay, enzyme immunoassay such as enzyme-linked immunosorbent assay (ELISA), fluoroimmunoassay, chemiluminescence immunoassay, immunonephelometry, dipstick-based immunoassay, and immunoturbidimetry. In some embodiments, the hormone is analyzed with mass spectrometry (MS). In some embodiments, the hormone is analyzed with chromatography. Non-limiting examples of chromatography include gel filtration chromatography, gas chromatography, and liquid chromatography. In some embodiments, the chromatography is followed by mass spectrometry (MS). In some embodiments, MS-MS is performed. In some embodiments, the metabolite is detected using an immunoassay. In some embodiments, the hormone is analyzed using precipitation (e.g., polyethylene glycol precipitation). In some embodiments, greater than or equal to one hormone is analyzed. In some embodiments, greater than or equal to 2, 3, 4, 5, 6, 7, 8, 9, or 10 hormones are analyzed. In some embodiments, from about 1 to about 10, about 2 to about 9, about 3 to about 8, about 4 to about 7, or about 5 to about 6 hormones are analyzed.

Vitamin

Provided herein are biomarkers comprising a vitamin that is associated with a high or a low likelihood of having or developing a disease or a condition disclosed herein relative to one or more control subjects. In some embodiments, a vitamin disclosed herein may be used to assess a high or a low likelihood of having or developing a disease or a condition disclosed herein relative to one or more control subjects. Non-limiting examples of vitamins include vitamin A, vitamin B (e.g., thiamin, riboflavin, niacin/nicotinic acid, pantothenic acid, pyridoxal/pyridoxine/pyridoxamine, biotin, folate/folic acid, B12), vitamin C, vitamin D, and vitamin K.

In some embodiments, the vitamin comprises vitamin A. In some embodiments, the amount of vitamin A is too high. In some embodiments, the vitamin comprises vitamin B. In some embodiments, vitamin B comprises thiamin, riboflavin, niacin/nicotinic acid, pantothenic acid, pyridoxal/pyridoxine/pyridoxamine, biotin, folate/folic acid, B12, or any combination thereof. In some embodiments, the vitamin B vitamin comprises B12. In some embodiments, the vitamin comprises vitamin D.

Described herein are methods for determining a presence or a level of a vitamin in a subject (e.g., animal or non-human subject). In some embodiments, multiple vitamins are analyzed. In some embodiments, the multiple vitamins analyzed are for a single condition or disease. In some embodiments, the multiple vitamins analyzed are for multiple conditions or diseases. In some embodiments, different vitamins from different sample types are used to assess a high or a low likelihood of having or developing a disease or a condition disclosed herein relative to one or more control subjects. In some embodiments, the vitamin is analyzed with chromatography. Non-limiting examples of chromatography include gas chromatography and liquid chromatography. In some embodiments, the chromatography is followed by mass spectrometry (MS). In some embodiments, MS-MS is performed. In some embodiments, the chromatography is coupled with electrochemical detection. In some embodiments, the chromatography is coupled with ultraviolet light detection. In some embodiments, the vitamin is analyzed though electrophoresis, such as for example, capillary electrophoresis. In some embodiments, the vitamin is analyzed through immunoassays. Non-limiting examples of types of immunoassays include immunohistochemistry, radioimmunoassay, enzyme immunoassay such as enzyme-linked immunosorbent assay (ELISA), fluoroimmunoassay, chemiluminescence immunoassay, immunonephelometry, dipstick-based immunoassay, and immunoturbidimetry. In some embodiments, the vitamin is analyzed with a spectrophotometric assay. In some embodiments, the vitamin is analyzed with a fluorometric assay. In some embodiments, greater than or equal to one vitamin is analyzed. In some embodiments, greater than or equal to 2, 3, 4, 5, 6, 7, 8, 9, or 10 vitamins are analyzed. In some embodiments, from about 1 to about 10, about 2 to about 9, about 3 to about 8, about 4 to about 7, or about 5 to about 6 vitamins are analyzed.

Cell Types

Provided herein are biomarkers comprising a cell type that is associated with a high or a low likelihood of having or developing a disease or a condition disclosed herein relative to one or more control subjects. In some embodiments, a cell type disclosed herein may be used to assess a high or a low likelihood of having or developing a disease or a condition disclosed herein relative to one or more control subjects. Non-limiting examples of cells include red blood cells, white blood cells, epithelial cells, muscle cells, liver cells, kidney cells, intestinal cells, and lung cells.

In some embodiments, the cell type comprises a red blood cell. In some embodiments the red blood cell is analyzed by obtaining a count of red blood cells. A red blood cell count can indicate conditions such as anemia, malnutrition, and some cancers. In some embodiments, the red blood cells are analyzed for hemoglobin. In some embodiments, the red blood cells are analyzed for the concentration of red blood cells. In some embodiments, the red blood cells are analyzed to determine the average size of the red blood cells. In some embodiments, the cell type comprises a white blood cell. In some embodiments the white blood cell is analyzed by obtaining a count of white blood cells. A white blood cell count can indicate if a subject is fighting an infection or at an increased risk of infection. In some embodiments, the cell type is analyzed through histology. In some embodiments, the cell type morphology differs from that of control cell type morphology. In some embodiments, the cell type comprises cell types of the intestinal lining. Cell types collected from the intestinal lining can show loss of villi which aid in nutrient absorption. In some embodiments, the cell type is associated with atopic dermatitis. In some embodiments, the cell type comprises neutrophils, lymphocytes, CD4$^+$ T-cells, CD8$^+$ T-cells, CD21$^+$ B-cells, CD14$^+$ monocytes, or any combination thereof. In some embodiments, the cell type is associated with anemia. In some embodiments, the anemia is non regenerative. In some embodiments, the cell type comprises red blood cells.

Described herein are methods for determining a presence, level, or morphology of a cell type in a subject (e.g., animal or non-human subject). In some embodiments, multiple cell types are analyzed. In some embodiments, the multiple cell types analyzed are for a single condition or disease. In some embodiments, the multiple cell types analyzed are for multiple conditions or diseases. In some embodiments, different cell types from different sample types are used to assess a high or a low likelihood of having or developing a disease or a condition disclosed herein relative to one or more control subjects. In some embodiments, the cell type is analyzed with microscopy. Non-limiting examples of characteristics identified through microscopic analysis of cell type includes cell count, cell size, cell shape, and general appearance of cells. In some embodiments, the cell type is analyzed using flow cytometry. In some embodiments, the cell type is analyzed using an immunoassay. Non-limiting examples of types of immunoassays include immunohistochemistry, radioimmunoassay, enzyme immunoassay such as enzyme-linked immunosorbent assay (ELISA), fluoroimmunoassay, chemiluminescence immunoassay, immunonephelometry, immunophenotyping, and immunoturbidimetry. In some embodiments, greater than or equal to one cell type is analyzed. In some embodiments, greater than or equal to 2, 3, 4, 5, 6, 7, 8, 9, or 10 cell types are analyzed. In some embodiments, from about 1 to about 10, about 2 to about 9, about 3 to about 8, about 4 to about 7, or about 5 to about 6 cell types are analyzed.

Electrolyte and/or Mineral

Provided herein are biomarkers comprising an electrolyte or mineral that is associated with a high or a low likelihood of having or developing a disease or a condition disclosed herein relative to one or more control subjects. In some embodiments, an electrolyte or mineral disclosed herein may be used to assess a high or a low likelihood of having or developing a disease or a condition disclosed herein relative to one or more control subjects. Non-limiting examples of electrolytes include sodium, potassium, magnesium, calcium, and chloride. Non-limiting examples of minerals include iodine, fluoride, iron, manganese, copper, selenium, and zinc.

In some embodiments, the electrolyte comprises sodium. Low sodium levels can indicate dehydration, excess hydration, or problems with the heart, kidney or liver. In some embodiments, the electrolyte comprises calcium. Low calcium levels can lead to dry skin and brittle hair, as well as more serious conditions such as osteoporosis. In some embodiments, the mineral comprises iron. Low iron levels can lead to anemia. In some embodiments, the mineral comprises copper. Copper deficiency can cause dry hair and hair loss in patches. In some embodiments, the mineral comprises zinc. Zinc deficiencies can lead to hair loss and skin ulcers.

Described herein are methods for determining a presence or a level of an electrolyte or mineral in a subject (e.g., animal or non-human subject). In some embodiments, multiple electrolytes and/or minerals are analyzed. In some embodiments, the multiple electrolytes and/or minerals analyzed are for a single condition or disease. In some embodiments, the multiple electrolytes and/or minerals analyzed are for multiple conditions or diseases. In some embodiments, different electrolytes and/or minerals from different sample types are used to assess a high or a low likelihood of having or developing a disease or a condition disclosed herein relative to one or more control subjects. In some embodiments, the electrolyte and/or mineral is measured using flame photometry. In some embodiments, the electrolyte and/or mineral is measured using ion selective electrodes. In some embodiments, the electrolyte and/or mineral is measured using inductively-coupled plasma mass spectrometry (MS). In some embodiments, the electrolyte and/or mineral is measured using inductively-coupled plasma optical emission spectroscopy. In some embodiments, greater than or equal to one electrolyte or mineral is analyzed. In some embodiments, greater than or equal to 2, 3, 4, 5, 6, 7, 8, 9, or 10 electrolytes or minerals are analyzed. In some embodiments, from about 1 to about 10, about 2 to about 9, about 3 to about 8, about 4 to about 7, or about 5 to about 6 electrolytes or minerals are analyzed.

In some embodiments, a binary cutoff may be determined for a biomarker by either the presence of the genotype that predisposes to medically-relevant dysregulation or based on a clinical odds ratio of risk for the manifestation of symptomology. In some embodiments, the information for biomarkers of a subject may be assessed through diagnostic testing. Non limiting examples of diagnostic testing include complete blood count, serum chemistry, urinalysis, cytological methods, and lateral flow methods. In some embodiments, the cytological methods comprise analysis of blood, fine needle aspiration of a mass, urine sedimentation, fecal flotation or any combination thereof. In some embodiments, the lateral flow methods comprise analysis for heartworm. In some embodiments, the lateral flow methods comprise analysis for tick-borne illness. In some embodiments, the diagnostic test may comprise allergy testing, additional blood chemistry testing, advanced staining cytology, genetics, hematology testing, hematology testing for coagulopathies, histopathology, immunology, vaccine titers, microbiology, toxicology, molecular biology. In some embodiments, the biomarkers disclosed herein will be compared to reference values. Non-limiting examples of reference values for biomarkers in canines are listed in Table 1. In some embodiments, standard laboratory tests may be performed and compared to reference values. Table 2 shows reference ranges of canines and felines for items measured in a CBC (complete blood panel) blood test. Table 3 shows reference ranges of canines and felines for items measured in a serum chemistry blood test. Table 4 shows reference ranges of canines and felines for gases and pH measured in a blood test. Table 5 shows reference ranges of canine and felines for individual tests that can be analyzed for a companion animal. In some embodiments, the results of one or more tests may be higher. In some embodiments, the results of one or more tests may be lower. In some embodiments, the results of one or more tests may be within the reference ranges or amounts.

TABLE 1

| | Reference Values |
|---|---|
| Hormones | |
| Cortisol- resting | 1.0-5.0 ug/dL |
| Cortisol- post ACTH | 5.5-2.0 ug/dL |
| ACTH | 13-46 pg/ml |
| Testosterone Neutered Male | <0.7 nmol/L |
| Progesterone (female) | 10-90 ng/ml |
| Vitamins | |
| Vitamin B9 (Folate) | 7.7-24.4 µg/L |
| Vitamin B12 (Cobalamin) | 251-908 ng/L |
| Vitamin D | 14-155 ng/mL |
| Vitamin A | 208-612 µg/100 mL |
| Vitamin E | 2.7-12.4 µg/mL |
| thiamine | 46-112 µg/L |

TABLE 1-continued

| | Reference Values |
|---|---|
| Cell Types | |
| Red blood cells | 4.95-7.87 × $10^6$/mcL |
| White blood cells | 5.0-14.1 × $10^3$/mcL |
| Band neutrophils | 0.0-0.3 × $10^3$/mcL |
| Segmented neutrophils | 3.0-11.4 × $10^3$/mcL |
| Lymphocytes | 1.0-4.8 × $10^3$/mcL |
| Monocytes | 0.15-1.35 × $10^3$/mcL |
| Eosinophils | 0.1-0.75 × $10^3$/mcL |
| Basophils | 0.0-0.1 × $10^3$/mcL |
| Electrolytes and Minerals | |
| Sodium | 142-152 mEq/L |
| Potassium | 3.9-5.1 mEq/L |
| Magnesium | 1.6-2.4 mg/dL |
| Calcium | 2.3-2.9 mmol/L |
| Chloride | 110-124 mmol/L |
| Copper | 0.2-0.8 ppm |
| Zinc | 0.70-2 ppm |

TABLE 2

| | Units (USA) | Canine | Feline |
|---|---|---|---|
| PCV | % | 35-57 | 30-45 |
| Hgb | g/dL | 11.9-18.9 | 9.8-15.4 |
| RBCs | ×$10^6$/mcL | 4.95-7.87 | 5.0-10.0 |
| Reticulocytes | % | 0-1.0 | 0-0.6 |
| Absolute reticulocyte count | ×$10^3$/mcL | <80 | <60 |
| MCV | fL | 66-77 | 39-55 |
| MCH | pg | 21.0-26.2 | 13-17 |
| MCHC | g/dL | 32.0-36.3 | 30-36 |
| Platelets | ×$10^3$/mcL | 211-621 | 300-800 |
| MPV | fL | 6.1-10.1 | 12-18 |
| WBCs | ×$10^3$/mcL | 5.0-14.1 | 5.5-19.5 |
| Neutrophils (segmented) | % | 58-85 | 45-64 |
| | ×$10^3$/mcL | 2.9-12.0 | 2.5-12.5 |
| Neutrophils (band) | % | 0-3 | 0-2 |
| | ×$10^3$/mcL | 0-0.45 | 0-0.3 |
| Lymphocytes | % | 8-21 | 27-36 |
| | ×$10^3$/mcL | 0.4-2.9 | 1.5-7.0 |
| Monocytes | % | 2-10 | 0-5 |
| | ×$10^3$/mcL | 0.1-1.4 | 0-0.9 |
| Eosinophils | % | 0-9 | 0-4 |
| | ×$10^3$/mcL | 0-1.3 | 0-0.8 |
| Basophils | % | 0-1 | 0-1 |
| | ×$10^3$/mcL | 0-0.14 | 0-0.2 |
| M:E | | 0.75-2.5 | 0.6-3.9 |
| Plasma proteins | g/dL | 6.0-7.5 | 6.0-7.5 |
| Plasma fibrinogen | mg/dL | 150-300 | 150-300 |

MCV = mean corpuscular volume; MCH = mean corpuscular hemoglobin; MCHC = mean corpuscular hemoglobin concentration; MPV = mean platelet volume; M:E = myeloid:erythroid ratio

TABLE 3

| | Units (USA) | Canine | Feline |
|---|---|---|---|
| ALT | U/L | 10-109 | 25-97 |
| Amylase | U/L | 226-1,063 | 550-1,458 |
| Alk phos | U/L | 1-114 | 0-45 |
| AST | U/L | 13-15 | 7-38 |
| CK | U/L | 52-368 | 69-214 |
| GGT | U/L | | |
| LDH | U/L | 0-236 | 58-120 |
| SDH | U/L | | |
| Bicarbonate | mEq/L | 17-24 | 17-24 |
| Bilirubin | mg/dL | 0-0.3 | 0-0.1 |
| Calcium | mg/dL | 9.1-11.7 | 8.7-11.7 |
| Chloride | mEq/L | 110-124 | 115-130 |
| Cholesterol | mg/dL | 135-278 | 71-156 |
| Creatinine | mg/dL | 0.5-1.7 | 0.9-2.2 |
| Glucose | mg/dL | 76-119 | 60-120 |

TABLE 3-continued

|  | Units (USA) | Canine | Feline |
|---|---|---|---|
| Magnesium | mg/dL | 1.6-2.4 | 1.7-2.6 |
| Phosphorus | mg/dL | 2.9-5.3 | 3.0-6.1 |
| Potassium | mEq/L | 3.9-5.1 | 3.7-6.1 |
| Total protein | g/dL | 5.4-7.5 | 6.0-7.9 |
| Albumin | g/dL | 2.3-3.1 | 2.8-3.9 |
| Globulin | g/dL | 2.7-4.4 | 2.6-5.1 |
| Sodium | mEq/L | 142-152 | 146-156 |
| Urea nitrogen | mg/dL | 8-28 | 19-34 |
| Bicarbonate | mmol/L | 17-24 | 17-24 |
| Bilirubin | mcmol/L | 0-5.1 | 0-1.7 |
| Calcium | mmol/L | 2.3-2.9 | 2.2-2.9 |
| Chloride | mmol/L | 110-124 | 115-130 |
| Cholesterol | mmol/L | 3.5-7.2 | 1.8-4.0 |
| Creatinine | mcmol/L | 44-150 | 80-194 |
| Glucose | mmol/L | 4.2-6.6 | 3.3-6.7 |
| Magnesium | mmol/L | 0.7-1.0 | 0.7-1.1 |
| Phosphorus | mmol/L | 0.9-1.7 | 1.0-2.0 |
| Potassium | mmol/L | 3.9-5.1 | 3.7-6.1 |
| Protein | g/L | 54-75 | 60-79 |
| Albumin | g/L | 23-31 | 28-39 |
| Globulin | g/L | 27-44 | 26-51 |
| Sodium | mmol/L | 142-152 | 146-156 |
| Urea nitrogen | mmol/L | 2.9-10.0 | 6.8-12.1 |

ALT = alanine aminotransferase; Alk phos = alkaline phosphatase; AST = aspartate aminotransferase; CK = creatine kinase; GGT = gamma glutamyltransferase; LDH = lactate dehydrogenase; SDH = sorbitol dehydrogenase

TABLE 4

|  | Units | Canine | Feline |
|---|---|---|---|
| pH | N/A USA | 7.31-7.42 | 7.24-7.40 |
| $HCO_3$ | mEq/L | 17-24 | 17-24 |
| $pCO_2$ | mmHg | 29-42 | 29-42 |
| $pO_2$ | mmHg SI | 85-95 | 85-95 |
| $HCO_3$ | mcmol/L | 17-24 | 17-24 |
| $pCO_2$ | kPa | 3.86-5.60 | 3.86-5.60 |
| $pO_2$ | kPa | 11.3-12.66 | 11.3-12.66 |

TABLE 5

|  | Units (USA) | Canine | Feline |
|---|---|---|---|
| T4 | μg/dL | 0.5-10.0 | 0.5-20.0 |
| T4 | nmol/L | 6.4-128.7 | 6.4-257.4 |
| Taurine- Whole Blood | μM | 200-350 | 300-600 |
| Taurine- Plasma | μM | 60-120 | 80-120 |
| Bile Acids (8 hr fast) | μmol/L | 13 |  |
| Bile Acids (2 hours post feeding) | μmol/L | <30 |  |
| TLI | μg/L | 5.7-45.2 | 12-82.0 |
| B12 | ng/L | 251-908 | 290-1500 |
| Folate | μg/L | 7.7-24.4 | 9.7-21.6 |
| Protein C | % | 75-135 | 65-120 |
| cPLI | μg/L | 0-200 |  |
| cPLI- retest recommended | μg/L | 201-399 |  |

TLI = Trypsin-like Immunoreactivity; cPLI = canine pancreatic lipase immunoreactivity In some embodiments, methods of detection may include a physical examination. In some embodiments, the physical examination is performed during a visit to a medical professional. In some embodiments, the physical examination is performed during a visit to a veterinarian. In some embodiments, the physical examination is performed during a hospital stay. In some embodiments, the physical examination is performed daily during a hospital stay. Non-limiting examples of data collected during a physical exam include temperature, respiration rate, heart rate, examination of gums, capillary refill time, assessment of vision, palpation of limbs, palpation of the abdomen, body condition score, blood pressure, and electrocardiogram.

Methods of Generating a Profile

Described herein are methods of generating a profile based, at least in part on genotype, phenotype, environmental, activity, clinical, or behavior data of the subject (e.g., animal or non-human subject). In some embodiments, the profile comprises a genetic profile. In some embodiments, the profile comprises a phenotypic profile. In some embodiments, the profile comprises an environmental profile. In some embodiments, the profile comprises an activity profile. In some embodiments, the profile comprises a clinical profile. In some embodiments, the profile comprises a genotype-phenotype profile, encompassing both genotype data and phenotype data for the non-human subject. In some embodiments, the genotype-phenotype profile is combined with one or more profiles described herein, such as an environmental profile, an activity profile, and so forth. In some embodiments, the profile for the non-human subject is analyzed with a machine learning model to calculate a wellness probability score (WPS) for the non-human subject. In some embodiments, the WPS is indicative of whether the subject is at a high likelihood to develop a certain phenotype disclosed here, such as a disease or a condition disclosed herein.

Genotype Data

Disclosed herein are methods for receiving, obtaining, or analyzing genotype data to generate a profile for the subject (e.g., animal or non-human subject). In some embodiments, the genotype data comprises the genotypes disclosed herein (e.g., genetic variants, such as SNPs, indels, CNVs, etc.) or epigenetic data. In some embodiments, the epigenetic data comprises histone modifications. Non-limiting examples of histone modifications include histone acetylation, histone methylation, histone phosphorylation, histone deamination, histone ubiquitylation, and histone sumoylation. In some embodiments, the genotype data comprises DNA methylation data. Table 6 shows common clinical examples with a genetic component for canines and felines.

TABLE 6

| Canine | Feline |
|---|---|
| Behavior | Hypertrophic Cardiomyopathy |
| Diabetes mellitus | Polycystic Kidney Disease |
| Obesity | Hepatic Lipidosis |
| Atopy | Obesity |
| Blindness | Feline Infectious Peritonitis |
| Lymphoma | Hyperthyroidism |
| Mammary Cancer | Behavior |
| Cataracts | Diabetes mellitus |
| Osteosarcoma | Arthritis |
| IVDD |  |
| Epilepsy |  |
| Mast Cell Tumor |  |
| Hemangiosarcoma |  |
| Osteoarthritis |  |
| Patellar Luxation |  |
| Deafness |  |
| CCL rupture |  |
| Upper airway syndrome |  |
| Hypothyroidism |  |
| Dilated Cardiomyopathy |  |
| Brachycephaly |  |
| Squamous Cell Carcinoma |  |
| Urolithiasis |  |

In some embodiments, the number of loci analyzed is in a range of about 1 to about 200,000 loci, about 100 to about 200,000 loci, about 1,000 to about 200,000 loci, about 10,000 to about 200,000 loci, about 50,000 to about 200,000 loci, or about 100,000 to about 200,000 loci. The genotypes disclosed herein can comprise at least or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more polymorphisms. In some embodiments, the CNV comprises at least or about two, three, four, five, six, seven, eight, nine, ten, twenty, thirty, forty or fifty nucleic acid molecules. In some embodiments, the genotype is heterozygous. In some embodiments, the genotype is homozygous.

In some embodiments, the genotype data are generated using the methods of detection disclosed herein. In some embodiments, a single genetic variant is used to generate the genotype data. In some embodiments, two genetic variants are used to generate the genotype data. In some embodiments, three genetic variants are used to generate the genotype data. In some embodiments, four genetic variants are used to generate the genotype data. In some embodiments, five genetic variants are used to generate the genotype data. In some embodiments, six genetic variants are used to generate the genotype data. In some embodiments, seven genetic variants are used to generate the genotype data. In some embodiments, eight genetic variants are used to generate the genotype data. In some embodiments, nine genetic variants are used to generate the genotype data. In some embodiments, ten genetic variants are used to generate the genotype data. In some embodiments, at least about two genetic variants are used to generate the genotype data. In some embodiments, at least about three genetic variants are used to generate the genotype data. In some embodiments, at least about four genetic variants are used to generate the genotype data. In some embodiments, at least about five genetic variants are used to generate the genotype data. In some embodiments, at least about six genetic variants are used to generate the genotype data. In some embodiments, at least about seven genetic variants are used to generate the genotype data. In some embodiments, at least about eight genetic variants are used to generate the genotype data. In some embodiments, at least about nine genetic variants are used to generate the genotype data. In some embodiments, at least about ten genetic variants are used to generate the genotype data.

In some embodiments, the report on the genetic traits may classify the subject as affected. In some embodiments, the report on the genetic traits may classify the subject as carrier. In some embodiments, the report on the genetic traits may classify the subject as free. In some embodiments, the report on the genetic traits may classify the subject as at risk. In some embodiments, the report on the genetic traits may classify the subject as clear. In some embodiments, the report on the genetic traits will be reported and explained to the user. In some embodiments, the report on the genetic traits will be reported and explained to a veterinarian. In some embodiments, the report on the genetic traits will be reported and explained to the user by the veterinarian. In some embodiments, the report on the genetic traits will be reported and explained to the user by the pet wellness system. Non-limiting examples of genetic variants associated with one or more diseases or conditions disclosed herein include chondrodystrophy and intervertebral disc disease risk (CDDY), degenerative myelopathy (DM), cone-rod dystrophy (cord1-PRA/crd4), progressive rod-cone degeneration (prcd-PRA), bald thigh syndrome, cystinuria Type I-B (SLC7A9 p.A217T), hyperuricosuria (HUU), cystinuria Type I-A (SLC3A1 p.I192V), cystinuria Type I-A (SLC3A1 p.S698G), dilated cardiomyopathy risk factor (PDK-4 related), collie eye anomaly (CEA), exercise-induced collapse (EIC), dilated cardiomyopathy risk factor (TTN-related), Multidrug resistance 1 (MDR1) medication sensitivity, ichthyosis, von Willebrand's disease Type I (vWD 1), canine multifocal retinopathy 1 (CMR1), and Stargardt disease.

Phenotype Data

Disclosed herein are methods for receiving, obtaining, or analyzing phenotype data to generate a profile of a subject (e.g., non-human subject or animal). In some embodiments, the phenotype data comprises clinical information. In some embodiments, the phenotype data comprises physical attribute information. In some embodiments, the phenotype data comprises clinical information and physical attribute information. In some embodiments, the clinical information comprises a medical history of the non-human subject. In some embodiments, the clinical information comprises a family medical history of the non-human subject. In some embodiments, the clinical information comprises a diagnosis or prognosis of one or more diseases or one or more conditions. In some embodiments, the diagnosis or prognosis comprises dietary sensitivities. In some embodiments, the dietary sensitivity comprises gluten sensitivity, glycan sensitivity, or lactose sensitivity. In some embodiments, the diagnosis or prognosis comprises lameness. In some embodiments, the lameness stems from a joint. In some embodiments, the joint comprises one or both hips, one or both shoulders, one or both knees, one or both elbows, or one or both hocks. In some embodiments, the diagnosis or prognosis comprises allergies. In some embodiments, the allergy comprises a skin allergy, a dust allergy, an insect sting allergy, a food allergy, an eye allergy, a drug allergy, a latex allergy, a mold allergy, and/or a pest allergy. In some embodiments, the allergy trait comprises allergic inflammation. In some embodiments, the pest allergy comprises an allergy to mites. In some embodiments, the diagnosis or prognosis comprises exercise intolerance. In some embodiments, the exercise intolerance comprises aerobic performance, difficulty losing weight, endurance, power, fitness benefits, reduced heartbeat response to exercise, lean body mass, muscle soreness, muscle damage risk, muscle repair impairment, stress fracture, overall injury risk, potential for obesity, or resting metabolic rate impairment. In some embodiments, the diagnosis or prognosis comprises reproductive status. In some embodiments, the diagnosis or prognosis comprises pre-existing conditions. In some embodiments, the diagnosis or prognosis comprises known adverse lifetime events for the non-human subject. In some embodiments, the adverse lifetime events comprises surgery, joint damage, severe trauma, or fractures. In some embodiments, the physical attribute information comprises age of the non-human subject. In some embodiments, the physical attribute information comprises sex of the non-human subject. In some embodiments, the physical attribute information comprises weight of the non-human subject. In some embodiments, the physical attribute information comprises breed of the non-human subject. In some embodiments, the clinical information comprises biomarker information for the non-human subject. In some embodiments, the biomarkers comprise one or more of a protein, a sugar, a lipid, a hormone, a vitamin, a cell, a metabolite, or an electrolyte. In some embodiments, the phenotype data is provided by the guardian of the non-human subject. In some embodiments, the phenotype data is provided by the veterinarian of the non-human subject.

In some embodiments, the phenotype data are generated using the methods of detection disclosed herein. In some embodiments, a single phenotype data is used. In some embodiments, two phenotype data are used. In some embodiments, three phenotype data are used. In some embodiments, four phenotype data are used. In some embodiments, five phenotype data are used. In some embodiments, six phenotype data are used. In some embodiments, seven phenotype data are used. In some embodiments, eight phenotype data are used. In some embodiments, nine phenotype data are used. In some embodiments, ten phenotype data are used. In some embodiments, at least about two phenotype data are used. In some embodiments, at least about three phenotype data are used. In some embodiments, at least about four phenotype data are used. In some embodiments, at least about five phenotype data are used. In some embodiments, at least about six phenotype data are used. In some embodiments, at least about seven phenotype data are used. In some embodiments, at least about eight phenotype data are used. In some embodiments, at least about nine phenotype data are used. In some embodiments, at least about ten phenotype data are used.

Genotype-Phenotype Profile

Disclosed herein are methods for generating a genotype-phenotype profile for subject (e.g., animal or non-human subject). In some embodiments, the profile is generated using the methods disclosed herein. In some embodiments, the methods disclosed herein to generate the profile encompasses the system. In some embodiments, the genotype-phenotype profile is generated from a combination of genotype data and phenotype data. In some embodiments, the profile changes throughout the lifespan of the non-human subject. In some embodiments, genetic and phenotypic testing may be utilized by a recursive algorithm. In some embodiments, the recursive algorithm may make increasingly intelligent recommendations for pet owners. In some embodiments, the recursive algorithm may allow for solutions that better capture the total health needs of their pet than traditional pet nutrition options.

Activity Data

Disclosed herein are methods for generating the activity data for the subject (e.g., animal or non-human subject). In some embodiments, the exercise and/or activity data comprises activity level, activity type, calories burned, or time asleep for the non-human subject. In some embodiments, the activity data is obtained from an activity tracking device worn by the non-human subject. Non-limiting examples of activity data include types of activity or activities, frequency of activity or activities, and duration of activity or activities. In some embodiments, the activity data is provided by the guardian of the non-human subject. In some embodiments, the activity data is provided by the veterinarian of the non-human subject.

In some embodiments, the activity data comprises consumption data for the subject (e.g., animal or non-human subject). In some embodiments, the consumption data comprises calories or water consumed or food preferences of the non-human subject. In some embodiments, the consumption data comprises a vitamin deficiency, a mineral deficiency, an antioxidant deficiency, a metabolic imbalance, a metabolic impairment, a metabolic sensitivity, an allergy, satiety, and/or the effectiveness of a healthy diet. Non-limiting examples of consumption data include loss of appetite, food preference, and caloric intake. In some embodiments, the consumption data is provided by the guardian of the non-human subject. In some embodiments, the consumption data is provided by the veterinarian of the non-human subject.

Behavioral Data

Disclosed herein are methods for generating the behavioral data for the subject (e.g., animal or non-human subject). In some embodiments, the behavioral data comprises chewing, itching, aggression, neurosis, anxiety, or energy level of the non-human subject. Non-limiting examples of behavioral data include biting, scratching, scooting, and sighing. In some embodiments, the behavioral data is provided by the guardian of the non-human subject. In some embodiments, the behavioral data is provided by the veterinarian of the non-human subject.

Environmental Data

Disclosed herein are methods for generating the environmental data for the subject (e.g., animal or non-human subject). In some embodiments, the environmental data comprises geographic location and time spent inside/outside for the non-human subject. For example the geographic location may be a urban (e.g., city), a rural environment, or a suburban environment. In some embodiments, the environmental data is provided by the guardian of the non-human subject. In some embodiments, the environmental data is provided by the veterinarian of the non-human subject.

Wellness Probability Score

Disclosed herein are methods for calculating a wellness probability score (WPS) representing a likelihood that a subject (e.g., animal or non-human subject) has, or is at risk to develop, one or more diseases or conditions. In some embodiments, the WPS is calculated using the profile (e.g., genotype-phenotype profile) disclosed herein. In some embodiments, the WPS is calculated using the activity data disclosed herein. In some embodiments, the WPS is calculated using the behavioral data disclosed herein. In some embodiments, the WPS is calculated using the environmental data disclosed herein. In some embodiments, the WPS is calculated using biomarker data disclosed herein. In some embodiments, the WPS is calculated using a combination of data. In some embodiments, multiple WPSs are generated. Non-limiting examples of multiple WPSs include activity WPS, chronic condition WPS, nutritional WPS, allergy WPS, acute condition WPS, and overall WPS.

The WPS can be calculated using a variety of suitable methodologies. In some embodiments, the WPS is on a scale of 0 to 1, where a presence of a risk factor associated with a disease or a condition disclosed herein is assigned a 1, and an absence of the genetic variant a 0. However, it should be noted that the numeric assignments (0,1) could be flipped (where 1 is assigned to an absence of the risk factor and 0 is assigned to the presence of the risk factor). In some embodiments, more than one risk factor is detected, and a combined risk score is calculated considering the sum of the individual WPS for a given disease or condition. In some embodiments, more than one risk factor is considered and a combined score is calculated considering the sum of individual WPS for multiple diseases or conditions. In some embodiments, weights are applied to the individual WPS for a given disease or indication. For example, where there are multiple risk factors associated with a disease or condition, a weight may be applied to the score attributed to the presence of each risk factor depending on their relative association (e.g., p-value, odds ratio, relative risk) with the disease or the condition. In some embodiments, the risk factor comprises a genetic variant, one or more biomarkers, an environmental factor, a behavior trait, a phenotype (e.g., weight, BMI) or an activity factor (e.g., frequency or intensity of exercise, time or quality of sleep, etc.), or any combination thereof. In some embodiments, where a risk factor is detected, the WPS of 1 is indicative of an inclusive need or an exclusive need. For example, the presence of a genetic variant associated with Taurine deficiency in the subject is indicative that the subject has an inclusive need (for more Taurine) in the subject's diet. In another example, the presence of a genetic variant associated with copper toxicosis (an inherited metabolic disorder that can lead to liver failure when copper levels are higher than normal) in a subject ingesting more than normal copper is indicative that the subject has an exclusive need (for less copper) in the subject's diet.

In some embodiments, the WPS accounts for the relative risk that a presence of a risk factor may pose to a likelihood that the subject has or will develop the disease or the condition. For example, the WPS may be calculated by determining a linear correlation between a presence of a risk factor and presence of the disease or the condition. Linear correlations may be determined using a Pearson coefficient, where the score is on a scale of 1 to −1. In some embodiments, a score between 0 and 1 indicates a positive correlation, a score of 0 indicates no correlation, and a score between 0 and −1 indicates a negative correlation with the disease or the condition. In some embodiments, the relative risk is determined using an odds ratio (OR) or relative risk (RR) calculation. For example, an OR of 1 indicates that presence of the risk factor does not affect the odds of the subject having or developing the disease or condition, and OR of more than 1 is indicative of a higher odd that the subject has or will develop the disease or condition, and an OR of less than one is indicate of a lesser odd that the subject has or will develop the disease or the condition. In some embodiments, the confidence interval (CI) for the OR or RR is greater than or equal to about 90%, 91%, 92%, 93%, 94%, 95%, 96%, 97%, 98%, or 99%. In some embodiments, the CI is 100%. In some embodiments, the CI is 95%. In some embodiments, the probability that a risk factor will increase risk of the subject developing the disease or the condition involves calculating the log-odds and calculating the probability from the log-odds. In some embodiments, the probability is on a scale of 0-1. For example, the WPS for a given risk factor may be 0.1, 0.2, 0.3, 0.4, 0.5, 0.6, 0.7, 0.8, 0.9, or 1.0 (or any value in between these values). In some embodiments, where there is more than one risk factor considered, a combined score is calculated considering the sum of individual WPS for multiple diseases or conditions. In some embodiments, weights are applied to the individual WPS for a given disease or indication as described elsewhere herein. In some embodiments, a cutoff is determined to identify whether the WPS is indicative of an inclusive or an exclusive need. In some embodiments, WPS for a reference population of subjects having or not having the disease or the condition are analyzed using logistic regression, and an optimal cutoff is determined using the Youden index. In some embodiments, a WPS above the cutoff is indicative of an inclusive need or an exclusive need as described elsewhere herein.

In some embodiments, the WPS for each disease or condition are ranked depending on the relative severity of the diseases or the conditions. For example, if a subject is determined to have a high risk of developing hip dysplasia and a high risk of developing cardiomyopathy, the cardiomyopathy may be ranked above the hip dysplasia in terms of indicating the inclusive need or exclusive need. For example, the high risk of developing cardiomyopathy may indicate an inclusive need for a diuretic early in disease progression and regular cardiovascular exercise, whereas the high risk of developing hip dysplasia may indicate an exclusive need for less exercise high impact exercise and an inclusive need for more joint health supplements, pain medications, nonsteroidal anti-inflammatory drugs (NSAIDs), etc. The ultimate combined score in this example would take into consideration the percentage of subjects having cardiomyopathy that result in loss of life versus the percentage of subjects having hip dysplasia that result in loss of life to rank the inclusive or exclusive needs assigned to the combine risk score. While this example uses loss of life as a measure for how deleterious each individual risk may be to the subject, other measures are contemplated. Such means may include, but are not limited to, quality of life or life span. In this example, cardiomyopathy is far more likely to cause loss of life than hip dysplasia, so the combined score would indicate a primary need for a diuretic a regular cardiovascular exercise that is low impact (e.g., swimming), a secondary need for joint health supplements, pain medications, or nonsteroidal anti-inflammatory drugs (NSAIDs) (to the extent these do not cause drug-drug interactions with the diuretic). In some embodiments, a generated recommendation may include the ranking of the diseases or the conditions. In some embodiments, the WPS for each disease or condition may be combined to generate an overall WPS. In some embodiments, a generated recommendation may include the overall WPS.

In some embodiments, certain risk factors are used as a statistical moderator on the machine learning model such that they modulate the degree of risk. For example, if the subject having the high risk for developing cardiomyopathy and a high risk for hip dysplasia could not regularly exercise due to its environment being in a city (e.g., without a swimming pool), then the primary need for a diuretic will be given a greater significance in recommendation to the guardian or medical health care professional of the subject. In some embodiments, the risk factor serving as a statistical moderator comprises a genetic variant, one or more biomarkers, an environmental factor, a behavior trait, a phenotype (e.g., weight, BMI) or an activity factor (e.g., frequency or intensity of exercise, time or quality of sleep, etc.), or any combination thereof.

In some embodiments, the WPS is on a scale of 0 to 1. In some embodiments, the WPS is on a scale of −1 to 1. In some embodiments, the WPS is on a scale of 0 to 3. In some embodiments, the WPS is on a scale of 1 to 3. In some embodiments, the WPS is on a scale of 1 to 10. In some embodiments, the WPS is on a scale of 1 to 100. In some embodiments, a higher number in the scale corresponds to an increased risk of one or more conditions. In some embodiments, a higher number in the scale corresponds to an increased severity of one or more conditions. In some embodiments, a higher number in the scale corresponds to an increased number of conditions. In some embodiments, a lower number in the scale corresponds to an increased risk of one or more conditions. In some embodiments, a lower number in the scale corresponds to an increased severity of one or more conditions. In some embodiments, a lower number in the scale corresponds to an increased number of conditions.

In some embodiments, the WPS indicates a subject as being in the $25^{th}$ percentile for a disease or condition. In some embodiments, the WPS indicates a subject as being in the $25^{th}$ percentile for one or more diseases or conditions. In some embodiments, the WPS indicates a subject as being in the $50^{th}$ percentile for a disease or condition. In some embodiments, the WPS indicates a subject as being in the $50^{th}$ percentile for one or more diseases or conditions. In some embodiments, the WPS indicates a subject as being in the $75^{th}$ percentile for a disease or condition. In some embodiments, the WPS indicates a subject as being in the $75^{th}$ percentile for one or more diseases or conditions. In some embodiments, the WPS indicates a subject as being in one percentile for one disease or condition and in another percentile for another disease or condition. In some embodiments, the WPS indicates an overall percentile for the overall health and wellness of a subject, wherein the overall health and wellness of a subject relates to the subject having one or more conditions or a risk of developing one or more conditions. In some embodiments, the WPS indicates a subject as being in the $50^{th}$, $40^{th}$, $30^{th}$, $20^{th}$, or $10^{th}$ percentile. In some embodiments, the WPS indicates a subject as being in the $45^{th}$, $35^{th}$, $25^{th}$, $15^{th}$ or $5^{th}$ percentile. In some embodiments, the WPS indicates a subject as being in the $60^{th}$, $70^{th}$, $80^{th}$ of $90^{th}$ percentile. In some embodiments, the WPS indicates a subject as being in the $65^{th}$, $75^{th}$, $85^{th}$, or $95^{th}$ percentile. In some embodiments, the higher the percentile assigned to the subject the lower the chance the subject has a disease or condition or a risk of developing a disease or condition. In some embodiments, the higher the percentile assigned to the subject the lower the chance the subject has one or more diseases or conditions or a risk of developing one or more diseases or conditions. In some embodiments, the WPS indicates a percent risk that the subject has a condition or disease. In some embodiments, the WPS indicates a percent risk that the subject has one or more conditions or diseases. In some embodiments, the WPS indicates a percent risk that the subject is at risk of developing a disease or condition. In some embodiments, the WPS indicates a percent risk that the subject is at risk of developing one or more diseases or conditions. In some embodiments, the percent risk 5%. In some embodiments, the percent risk is 10%. In some embodiments, the percent risk is 15%. In some embodiments, the percent risk 20%. In some embodiments, the percent risk is 25%. In some embodiments, the percent risk is 30%. In some embodiments, the percent risk 35%. In some embodiments, the percent risk is 40%. In some embodiments, the percent risk is 45%. In some embodiments, the percent risk 50%. In some embodiments, the percent risk is 55%. In some embodiments, the percent risk is 60%. In some embodiments, the percent risk 65%. In some embodiments, the percent risk is 70%. In some embodiments, the percent risk is 75%. In some embodiments, the percent risk 80%. In some embodiments, the percent risk is 85%. In some embodiments, the percent risk is 90%. In some embodiments, the percent risk 95%. In some embodiments, the percent risk is between about 0% and about 10%. In some embodiments, the percent risk is between about 10% and about 20%. In some embodiments, the percent risk is between about 20% and about 30%. In some embodiments, the percent risk is between about 30% and about 40%. In some embodiments, the percent risk is between about 40% and about 50%. In some embodiments, the percent risk is between about 50% and about 60%. In some embodiments, the percent risk is between about 60% and about 70%. In some embodiments, the percent risk is between about 70% and about 80%. In some embodiments, the percent risk is between about 80% and about 90%. In some embodiments, the percent risk is between about 90% and about 100%. In some embodiments, the percent risk is less than 25%. In some embodiments, the percent risk is less than 50%. In some embodiments, the percent risk is less than 75%. In some embodiments, the percent risk is less than 100%. In some embodiments, the percent risk is greater than 0%. In some embodiments, the percent risk is greater than 25%. In some embodiments, the percent risk is greater than 50%. In some embodiments, the percent risk is greater than 75%. In some embodiments, the higher the percent risk the higher the chance the subject has a disease or condition or a risk of developing a disease or condition. In some embodiments, the higher the percent risk the higher the chance the subject has one or more diseases or conditions or a risk of developing one or more diseases or conditions.

Also provided are methods for monitoring the subject over a period of time (e.g., their lifetime). In some embodiments, the WPS changes over the lifespan of the non-human subject. For example, in some embodiments, the WPS is updated with an updated activity data, behavior data, environmental data, or any combination thereof. In some embodiments, the profile for the subject is updated. For example, a non-human subject may visit the veterinarian or medical provider for routine check-up during which time one or more biomarkers disclosed herein are measured in a sample obtained from the subject. In some embodiments, the sample is a blood sample. In some embodiments, the presence or level of the one or more biomarkers is added to the genotype-phenotype profile. In some embodiments, the WPS is updated every week, two weeks, three weeks, one month, two months, three months, four months, five months, six months, seven months, eight months, nine months, ten months, eleven months, one year, two years, three years, four years, five years, six years, seven years, eight years, nine years, ten years, or more.

Methods of Creating a Recommendation

Disclosed herein are methods comprising recommending a product (e.g., nutritional product), a therapeutic strategy, a behavior modification, or any combination thereof. In some embodiments, the recommendation is provided to the subject. In the case of the non-human subject, in some embodiments, the recommendation is provided to a guardian, medical care provider (e.g., veterinarian), or both of the non-human subject. In some embodiments, the recommendation is based on the WPS calculated for the subject. For example, the recommendation may relate to the likelihood that the subject has, or will develop the one or more conditions disclosed herein. In some embodiments, the recommendation relates to multiple WPSs, such as, for example, where multiple conditions are predicted.

In some embodiments, the recommendation is communicated to a user (e.g., subject, guardian, medical care provider) by an Application (App) on a personal electronic device of the user. Such App may be configured to display on a graphical user interface (GUI) of the personal electronic device the WPS(s), the recommendation(s), or a combination thereof. In some embodiments, the recommendation is communicated to the user in the form of a report that is delivered to the user, wherein the report comprises the WPS(s), the recommendation(s), or the combination thereof. In the case of an updated WPS(s), the report may also highlight important changes from previous WPS(s), such as the most recent WPS.

Diseases or Conditions

Disclosed herein are methods for predicting whether a subject disclosed herein (e.g., animal or non-human subject) has, or is at risk for developing, one or more diseases or conditions. In some embodiments, the subject is suffering from a condition or conditions, or symptoms related to the condition or conditions. In some embodiments, the one or more conditions comprises a deficiency disease or condition, a hereditary disease or condition, or behavioral disease or condition. In some embodiments, the condition comprises an immunological disease or condition and/or a metabolic disease or condition. In some embodiments, the immunological disease/condition comprises an autoimmune disease, disorder, or condition. Non-limiting examples of an autoimmune disease, disorder, or condition include Grave's disease, autoimmune thyroiditis (AIT), systemic lupus erythematosus (lupus), granulomatous meningoencephalomyelitis (GME), rheumatoid arthritis, inflammatory bowel disease, ulcerative colitis, and cancer. Non-limiting examples of metabolic diseases or conditions include Type 1 diabetes, Type 2 diabetes, diseases/conditions affecting absorption of macronutrients (e.g., amino acids, carbohydrates, or lipids), diseases/conditions affecting absorption of micronutrients (e.g., vitamins or minerals), diseases/conditions affecting mitochondrial function, diseases/conditions affecting liver function, and diseases/conditions affecting kidney function.

Product Recommendations

Disclosed herein are methods to creating a product recommendation or product recommendations. In some embodiments, the recommendation comprises a nutritional product. In some embodiments, the nutritional product is a food, a supplement, or a treat. In some embodiments, the nutritional product is a food. In some embodiments, the nutritional product is a supplement. In some embodiments, the nutritional product is a treat. In some embodiments, the recommendation comprises multiple nutritional products. In some embodiments, the recommendation comprises a food, a supplement, and a treat. In some embodiments, the recommendation comprises a food and a supplement. In some embodiments, the recommendation comprises a food and two supplements. In some embodiments, the recommendation comprises a food and a treat. In some embodiments, the recommendation comprises a food and two treats.

In some embodiments, food for a subject (e.g., non-human subject or animal) contains minimum percentages based on dry matter for macronutrients (e.g., protein, carbohydrate, fat, etc.). These percentages can be altered based on the one or more conditions of the subject or the risk of developing the one or more conditions for the subject. In some embodiments, the minimum percentage of protein is 5%. In some embodiments, the minimum percentage of protein is less than 5%. In some embodiments, the minimum percentage of protein is greater than 5%. In some embodiments, the minimum percentage of protein is 8%. In some embodiments, the minimum percentage of protein is less than 8%. In some embodiments, the minimum percentage of protein is greater than 8%. In some embodiments, the minimum percentage of protein is 12%. In some embodiments, the minimum percentage of protein is less than 12%. In some embodiments, the minimum percentage of protein is greater than 12%. In some embodiments, the minimum percentage of protein is 18%. In some embodiments, the minimum percentage of protein is less than 18%. In some embodiments, the minimum percentage of protein is greater than 18%. In some embodiments, the minimum percentage of protein is 30%. In some embodiments, the minimum percentage of protein is less than 30%. In some embodiments, the minimum percentage of protein is greater than 30%. In some embodiments, the minimum percentage of protein is 35%. In some embodiments, the minimum percentage of protein is less than 35%. In some embodiments, the minimum percentage of protein is greater than 35%. In some embodiments, the minimum percentage of protein is 40%. In some embodiments, the minimum percentage of protein is less than 40%. In some embodiments, the minimum percentage of protein is greater than 40%. In some embodiments, the minimum percentage of protein is 45%. In some embodiments, the minimum percentage of protein is less than 45%. In some embodiments, the minimum percentage of protein is greater than 45%. In some embodiments, the minimum percentage of protein is 50%. In some embodiments, the minimum percentage of protein is less than 50%. In some embodiments, the minimum percentage of protein is greater than 50%. In some embodiments, the minimum percentage of protein is 55%. In some embodiments, the minimum percentage of protein is less than 55%. In some embodiments, the minimum percentage of protein is greater than 55%. In some embodiments, the minimum percentage of protein is 60%. In some embodiments, the minimum percentage of protein is less than 60%. In some embodiments, the minimum percentage of protein is greater than 60%. In some embodiments, the minimum percentage of protein is 65%. In some embodiments, the minimum percentage of protein is less than 65%. In some embodiments, the minimum percentage of protein is greater than 65%. In some embodiments, the minimum percentage of protein is about 5% to about 65%. In some embodiments, the minimum percentage of protein is about 10% to about 60%. In some embodiments, the minimum percentage of protein is about 12% to about 55%. In some embodiments, the minimum percentage of protein is about 14% to about 50%. In some embodiments, the minimum percentage of protein is about 15% to about 45%. In some embodiments, the minimum percentage of protein is about 16% to about 40%. In some embodiments, the minimum percentage of protein is about 17% to about 35%. In some embodiments, the minimum percentage of protein is about 18% to about 30%. In some embodiments, the minimum percentage of carbohydrates is 5%. In some embodiments, the minimum percentage of carbohydrates is less than 5%. In some embodiments, the minimum percentage of carbohydrates is greater than 5%. In some embodiments, the minimum percentage of carbohydrates is 15%. In some embodiments, the minimum percentage of carbohydrates is less than 15%. In some embodiments, the minimum percentage of carbohydrates is greater than 15%. In some embodiments, the minimum percentage of carbohydrates is 25%. In some embodiments, the minimum percentage of carbohydrates is less than 25%. In some embodiments, the minimum percentage of carbohydrates is greater than 25%. In some embodiments, the minimum percentage of carbohydrates is 30%. In some embodiments, the minimum percentage of carbohydrates is less than 30%. In some embodiments, the minimum percentage of carbohydrates is greater than 30%. In some embodiments, the minimum percentage of carbohydrates is 40%. In some embodiments, the minimum percentage of carbohydrates is less than 40%. In some embodiments, the minimum percentage of carbohydrates is greater than 40%. In some embodiments, the minimum percentage of carbohydrates is 50%. In some embodiments, the minimum percentage of carbohydrates is less than 50%. In some embodiments, the minimum percentage of carbohydrates is greater than 50%. In some embodiments, the minimum percentage of carbohydrates is 55%. In some embodiments, the minimum percentage of carbohydrates is less than 55%. In some embodiments, the minimum percentage of carbohydrates is greater than 55%. In some embodiments, the minimum percentage of carbohydrates is 60%. In some embodiments, the minimum percentage of carbohydrates is less than 60%. In some embodiments, the minimum percentage of carbohydrates is greater than 60%. In some embodiments, the minimum percentage of carbohydrates is 65%. In some embodiments, the minimum percentage of carbohydrates is less than 65%. In some embodiments, the minimum percentage of carbohydrates is greater than 65%. In some embodiments, the minimum percentage of carbohydrates is 70%. In some embodiments, the minimum percentage of carbohydrates is less than 70%. In some embodiments, the minimum percentage of carbohydrates is greater than 70%. In some embodiments, the minimum percentage of carbohydrates is about 5% to about 70%. In some embodiments, the minimum percentage of carbohydrates is about 15% to about 70%. In some embodiments, the minimum percentage of carbohydrates is about 20% to about 70%. In some embodiments, the minimum percentage of carbohydrates is about 25% to about 65%. In some embodiments, the minimum percentage of carbohydrates is about 30% to about 60%. In some embodiments, the minimum percentage of carbohydrates is about 40% to about 60%. In some embodiments, the minimum percentage of carbohydrates is about 45% to about 55%. In some embodiments, the minimum percentage of fat is 5%. In some embodiments, the minimum percentage of fat is less than 5%. In some embodiments, the minimum percentage of fat is greater than 5%. In some embodiments, the minimum percentage of fat is 10%. In some embodiments, the minimum percentage of fat is less than 10%. In some embodiments, the minimum percentage of fat is greater than 10%. In some embodiments, the minimum percentage of fat is 15%. In some embodiments, the minimum percentage of fat is less than 15%. In some embodiments, the minimum percentage of fat is greater than 15%. In some embodiments, the minimum percentage of fat is 20%. In some embodiments, the minimum percentage of fat is less than 20%. In some embodiments, the minimum percentage of fat is greater than 20%. In some embodiments, the minimum percentage of fat is 25%. In some embodiments, the minimum percentage of fat is less than 25%. In some embodiments, the minimum percentage of fat is greater than 25%. In some embodiments, the minimum percentage of fat is 30%. In some embodiments, the minimum percentage of fat is less than 30%. In some embodiments, the minimum percentage of fat is greater than 30%. In some embodiments, the minimum percentage of fat is 40%. In some embodiments, the minimum percentage of fat is less than 40%. In some embodiments, the minimum percentage of fat is greater than 40%. In some embodiments, the minimum percentage of fat is 50%. In some embodiments, the minimum percentage of fat is less than 50%. In some embodiments, the minimum percentage of fat is greater than 50%. In some embodiments, the minimum percentage of fat is 60%. In some embodiments, the minimum percentage of fat is less than 60%. In some embodiments, the minimum percentage of fat is greater than 60%. In some embodiments, the minimum percentage of carbohydrates is about 5% to about 60%. In some embodiments, the minimum percentage of carbohydrates is about 5% to about 50%. In some embodiments, the minimum percentage of carbohydrates is about 5% to about 40%. In some embodiments, the minimum percentage of carbohydrates is about 5% to about 30%. In some embodiments, the minimum percentage of carbohydrates is about 5% to about 25%. In some embodiments, the minimum percentage of carbohydrates is about 5% to about 25%. In some embodiments, the minimum percentage of carbohydrates is about 10% to about 20%. In some embodiments, the food for a subject contains recommendations based on dry matter for micronutrients such as vitamins and minerals. These percentages can be altered based on the one or more conditions of the subject or the risk of developing the one or more conditions for the subject. In some embodiments, the minimum percentage of calcium is 0.2%. In some embodiments, the minimum percentage of calcium is less than 0.2%. In some embodiments, the minimum percentage of calcium is greater than 0.2%. In some embodiments, the minimum percentage of calcium is 0.4%. In some embodiments, the minimum percentage of calcium is less than 0.4%. In some embodiments, the minimum percentage of calcium is greater than 0.4%. In some embodiments, the minimum percentage of calcium is 0.5%. In some embodiments, the minimum percentage of calcium is less than 0.5%. In some embodiments, the minimum percentage of calcium is greater than 0.5%. In some embodiments, the minimum percentage of calcium is 0.6%. In some embodiments, the minimum percentage of calcium is less than 0.6%. In some embodiments, the minimum percentage of calcium is greater than 0.6%. In some embodiments, the minimum percentage of calcium is 0.8%. In some embodiments, the minimum percentage of calcium is less than 0.8%. In some embodiments, the minimum percentage of calcium is greater than 0.8%. In some embodiments, the minimum percentage of calcium is 1%. In some embodiments, the minimum percentage of calcium is less than 1%. In some embodiments, the minimum percentage of calcium is greater than 1%. In some embodiments, the minimum percentage of calcium is 1.2%. In some embodiments, the minimum percentage of calcium is less than 1.2%. In some embodiments, the minimum percentage of calcium is greater than 1.2%. In some embodiments, the minimum percentage of calcium is 1.4%. In some embodiments, the minimum percentage of calcium is less than 1.4%. In some embodiments, the minimum percentage of calcium is greater than 1.4%. In some embodiments, the minimum percentage of calcium is 1.6%. In some embodiments, the minimum percentage of calcium is less than 1.6%. In some embodiments, the minimum percentage of calcium is greater than 1.6%. In some embodiments, the minimum percentage of calcium is 1.8%. In some embodiments, the minimum percentage of calcium is less than 1.8%. In some embodiments, the minimum percentage of calcium is greater than 1.8%. In some embodiments, the minimum percentage of calcium is 2%. In some embodiments, the minimum percentage of calcium is less than 2%. In some embodiments, the minimum percentage of calcium is greater than 2%. In some embodiments, the minimum percentage of calcium is 2.2%. In some embodiments, the minimum percentage of calcium is less than 2.2%. In some embodiments, the minimum percentage of calcium is greater than 2.2%. In some embodiments, the minimum percentage of calcium is 2.4%. In some embodiments, the minimum percentage of calcium is less than 2.4%. In some embodiments, the minimum percentage of calcium is greater than 2.4%. In some embodiments, the minimum percentage of calcium is 2.6%. In some embodiments, the minimum percentage of calcium is less than 2.6%. In some embodiments, the minimum percentage of calcium is greater than 2.6%. In some embodiments, the percentage of calcium is about 0.2% to about 2.6%. In some embodiments, the percentage of calcium is about 0.4% to about 2.0%. In some embodiments, the percentage of calcium is about 0.5% to about 1.5%. In some embodiments, the percentage of calcium is about 0.5% to about 1.2%. In some embodiments, the percentage of calcium is about 0.6% to about 1.0%. In some embodiments, the minimum percentage of phosphorus is 0.2%. In some embodiments, the minimum percentage of phosphorus is less than 0.2%. In some embodiments, the minimum percentage of phosphorus is greater than 0.2%. In some embodiments, the minimum percentage of phosphorus is 0.4%. In some embodiments, the minimum percentage of phosphorus is less than 0.4%. In some embodiments, the minimum percentage of phosphorus is greater than 0.4%. In some embodiments, the minimum percentage of phosphorus is 0.5%. In some embodiments, the minimum percentage of phosphorus is less than 0.5%. In some embodiments, the minimum percentage of phosphorus is greater than 0.5%. In some embodiments, the minimum percentage of phosphorus is 0.6%. In some embodiments, the minimum percentage of phosphorus is less than 0.6%. In some embodiments, the minimum percentage of phosphorus is greater than 0.6%. In some embodiments, the minimum percentage of phosphorus is 0.8%. In some embodiments, the minimum percentage of phosphorus is less than 0.8%. In some embodiments, the minimum percentage of phosphorus is greater than 0.8%. In some embodiments, the minimum percentage of phosphorus is 1%. In some embodiments, the minimum percentage of phosphorus is less than 1%. In some embodiments, the minimum percentage of phosphorus is greater than 1%. In some embodiments, the minimum percentage of phosphorus is 1.2%. In some embodiments, the minimum percentage of phosphorus is less than 1.2%. In some embodiments, the minimum percentage of phosphorus is greater than 1.2%. In some embodiments, the minimum percentage of phosphorus is 1.4%. In some embodiments, the minimum percentage of phosphorus is less than 1.4%. In some embodiments, the minimum percentage of phosphorus is greater than 1.4%. In some embodiments, the minimum percentage of phosphorus is 1.6%. In some embodiments, the minimum percentage of phosphorus is less than 1.6%. In some embodiments, the minimum percentage of phosphorus is greater than 1.6%. In some embodiments, the percentage of phosphorus is about 0.2% to about 1.6%. In some embodiments, the percentage of phosphorus is about 0.4% to about 1.4%. In some embodiments, the percentage of phosphorus is about 0.4% to about 1.0%. In some embodiments, the percentage of phosphorus is about 0.5% to about 1.0%. In some embodiments, the percentage of phosphorus is about 0.5% to about 0.8%. In some embodiments, the minimum percentage of potassium is 0.4%. In some embodiments, the minimum percentage of potassium is less than 0.4%. In some embodiments, the minimum percentage of potassium is greater than 0.4%. In some embodiments, the minimum percentage of potassium is 0.5%. In some embodiments, the minimum percentage of potassium is less than 0.5%. In some embodiments, the minimum percentage of potassium is greater than 0.5%. In some embodiments, the minimum percentage of potassium is 0.6%. In some embodiments, the minimum percentage of potassium is less than 0.6%. In some embodiments, the minimum percentage of potassium is greater than 0.6%. In some embodiments, the minimum percentage of potassium is 0.7%. In some embodiments, the minimum percentage of potassium is less than 0.7%. In some embodiments, the minimum percentage of potassium is greater than 0.7%. In some embodiments, the minimum percentage of potassium is 0.8%. In some embodiments, the minimum percentage of potassium is less than 0.8%. In some embodiments, the minimum percentage of potassium is greater than 0.8%. In some embodiments, the percentage of potassium is about 0.4% to about 0.8%. In some embodiments, the percentage of potassium is about 0.5% to about 0.7%. In some embodiments, the minimum percentage of sodium is 0.06%. In some embodiments, the minimum percentage of sodium is less than 0.06%. In some embodiments, the minimum percentage of sodium is greater than 0.06%. In some embodiments, the minimum percentage of sodium is 0.08%. In some embodiments, the minimum percentage of sodium is less than 0.08%. In some embodiments, the minimum percentage of sodium is greater than 0.08%. In some embodiments, the minimum percentage of sodium is 0.1%. In some embodiments, the minimum percentage of sodium is less than 0.1%. In some embodiments, the minimum percentage of sodium is greater than 0.1%. In some embodiments, the minimum percentage of sodium is 0.2%. In some embodiments, the minimum percentage of sodium is less than 0.2%. In some embodiments, the minimum percentage of sodium is greater than 0.2%. In some embodiments, the minimum percentage of sodium is 0.3%. In some embodiments, the minimum percentage of sodium is less than 0.3%. In some embodiments, the minimum percentage of sodium is greater than 0.3%. In some embodiments, the minimum percentage of sodium is 0.4%. In some embodiments, the minimum percentage of sodium is less than 0.4%. In some embodiments, the minimum percentage of sodium is greater than 0.4%. In some embodiments, the percentage of sodium is about 0.06% to about 0.4%. In some embodiments, the percentage of sodium is about 0.08% to about 0.3%. In some embodiments, the percentage of sodium is about 0.1% to about 0.3%. In some embodiments, the percentage of sodium is about 0.1% to about 0.2%. In some embodiments, the minimum percentage of chloride is 0.1%. In some embodiments, the minimum percentage of chloride is less than 0.1%. In some embodiments, the minimum percentage of chloride is greater than 0.1%. In some embodiments, the minimum percentage of chloride is 0.15%. In some embodiments, the minimum percentage of chloride is less than 0.15%. In some embodiments, the minimum percentage of chloride is greater than 0.15%. In some embodiments, the minimum percentage of chloride is 0.2%. In some embodiments, the minimum percentage of chloride is less than 0.2%. In some embodiments, the minimum percentage of chloride is greater than 0.2%. In some embodiments, the minimum percentage of chloride is 0.25%. In some embodiments, the minimum percentage of chloride is less than 0.25%. In some embodiments, the minimum percentage of chloride is greater than 0.25%. In some embodiments, the minimum percentage of chloride is 0.3%. In some embodiments, the minimum percentage of chloride is less than 0.3%. In some embodiments, the minimum percentage of chloride is greater than 0.3%. In some embodiments, the minimum percentage of chloride is 0.35%. In some embodiments, the minimum percentage of chloride is less than 0.35%. In some embodiments, the minimum percentage of chloride is greater than 0.35%. In some embodiments, the minimum percentage of chloride is 0.4%. In some embodiments, the minimum percentage of chloride is less than 0.4%. In some embodiments, the minimum percentage of chloride is greater than 0.4%. In some embodiments, the minimum percentage of chloride is 0.45%. In some embodiments, the minimum percentage of chloride is less than 0.45%. In some embodiments, the minimum percentage of chloride is greater than 0.45%. In some embodiments, the minimum percentage of chloride is 0.5%. In some embodiments, the minimum percentage of chloride is less than 0.5%. In some embodiments, the minimum percentage of chloride is greater than 0.5%. In some embodiments, the percentage of chloride is about 0.1% to about 0.5%. In some embodiments, the percentage of chloride is about 0.12% to about 0.45%. In some embodiments, the percentage of chloride is about 0.15% to about 0.4%. In some embodiments, the percentage of chloride is about 0.2% to about 0.4%. In some embodiments, the percentage of chloride is about 0.25% to about 0.35%. In some embodiments, the minimum percentage of magnesium is 0.02%. In some embodiments, the minimum percentage of magnesium is less than 0.02%. In some embodiments, the minimum percentage of magnesium is greater than 0.02%. In some embodiments, the minimum percentage of magnesium is 0.04%. In some embodiments, the minimum percentage of magnesium is less than 0.04%. In some embodiments, the minimum percentage of magnesium is greater than 0.04%. In some embodiments, the minimum percentage of magnesium is 0.06%. In some embodiments, the minimum percentage of magnesium is less than 0.06%. In some embodiments, the minimum percentage of magnesium is greater than 0.06%. In some embodiments, the minimum percentage of magnesium is 0.08%. In some embodiments, the minimum percentage of magnesium is less than 0.08%. In some embodiments, the minimum percentage of magnesium is greater than 0.08%. In some embodiments, the minimum percentage of magnesium is 0.1%. In some embodiments, the minimum percentage of magnesium is less than 0.1%. In some embodiments, the minimum percentage of magnesium is greater than 0.1%. In some embodiments, the percentage of magnesium is about 0.02% to about 0.1%. In some embodiments, the percentage of magnesium is about 0.04% to about 0.08%. In some embodiments, the percentage of magnesium is about 0.05% to about 0.07%. In some embodiments, the dry matter basis of iron is 25 mg/kg. In some embodiments, the dry matter basis of iron is less than 25 mg/kg. In some embodiments, the dry matter basis of iron is greater than 25 mg/kg. In some embodiments, the dry matter basis of iron is 30 mg/kg. In some embodiments, the dry matter basis of iron is less than 30 mg/kg. In some embodiments, the dry matter basis of iron is greater than 30 mg/kg. In some embodiments, the dry matter basis of iron is 35 mg/kg. In some embodiments, the dry matter basis of iron is less than 35 mg/kg. In some embodiments, the dry matter basis of iron is greater than 35 mg/kg. In some embodiments, the dry matter basis of iron is 40 mg/kg. In some embodiments, the dry matter basis of iron is less than 40 mg/kg. In some embodiments, the dry matter basis of iron is greater than 40 mg/kg. In some embodiments, the dry matter basis of iron is 45 mg/kg. In some embodiments, the dry matter basis of iron is less than 45 mg/kg. In some embodiments, the dry matter basis of iron is greater than 45 mg/kg. In some embodiments, the dry matter basis of iron is 50 mg/kg. In some embodiments, the dry matter basis of iron is less than 50 mg/kg. In some embodiments, the dry matter basis of iron is greater than 50 mg/kg. In some embodiments, the dry matter basis of iron is 55 mg/kg. In some embodiments, the dry matter basis of iron is less than 55 mg/kg. In some embodiments, the dry matter basis of iron is greater than 55 mg/kg. In some embodiments, the dry matter basis of iron is 60 mg/kg. In some embodiments, the dry matter basis of iron is less than 60 mg/kg. In some embodiments, the dry matter basis of iron is greater than 60 mg/kg. In some embodiments, the dry matter basis of iron is 65 mg/kg. In some embodiments, the dry matter basis of iron is less than 65 mg/kg. In some embodiments, the dry matter basis of iron is greater than 65 mg/kg. In some embodiments, the dry matter basis of iron is 70 mg/kg. In some embodiments, the dry matter basis of iron is less than 70 mg/kg. In some embodiments, the dry matter basis of iron is greater than 70 mg/kg. In some embodiments, the dry matter basis of iron is 75 mg/kg. In some embodiments, the dry matter basis of iron is less than 75 mg/kg. In some embodiments, the dry matter basis of iron is greater than 75 mg/kg. In some embodiments, the dry matter basis of iron is 80 mg/kg. In some embodiments, the dry matter basis of iron is less than 80 mg/kg. In some embodiments, the dry matter basis of iron is greater than 80 mg/kg. In some embodiments, the dry matter basis of iron is 85 mg/kg. In some embodiments, the dry matter basis of iron is less than 85 mg/kg. In some embodiments, the dry matter basis of iron is greater than 85 mg/kg. In some embodiments, the dry matter basis of iron is 90 mg/kg. In some embodiments, the dry matter basis of iron is less than 90 mg/kg. In some embodiments, the dry matter basis of iron is greater than 90 mg/kg. In some embodiments, the dry matter basis of iron is 95 mg/kg. In some embodiments, the dry matter basis of iron is less than 95 mg/kg. In some embodiments, the dry matter basis of iron is greater than 95 mg/kg. In some embodiments, the dry matter basis of iron is 100 mg/kg. In some embodiments, the dry matter basis of iron is less than 100 mg/kg. In some embodiments, the dry matter basis of iron is greater than 100 mg/kg. In some embodiments, the dry matter basis of iron is about 25 mg/kg to about 100 mg/kg. In some embodiments, the dry matter basis of iron is about 35 mg/kg to about 90 mg/kg. In some embodiments, the dry matter basis of iron is about 40 mg/kg to about 80 mg/kg. In some embodiments, the dry matter basis of copper is 2.5 mg/kg. In some embodiments, the dry matter basis of copper is less than 2.5 mg/kg. In some embodiments, the dry matter basis of copper is greater than 2.5 mg/kg. In some embodiments, the dry matter basis of copper is 5 mg/kg. In some embodiments, the dry matter basis of copper is less than 5 mg/kg. In some embodiments, the dry matter basis of copper is greater than 5 mg/kg. In some embodiments, the dry matter basis of copper is 7.5 mg/kg. In some embodiments, the dry matter basis of copper is less than 7.5 mg/kg. In some embodiments, the dry matter basis of copper is greater than 7.5 mg/kg. In some embodiments, the dry matter basis of copper is 10 mg/kg. In some embodiments, the dry matter basis of copper is less than 10 mg/kg. In some embodiments, the dry matter basis of copper is greater than 10 mg/kg. In some embodiments, the dry matter basis of copper is 12.5 mg/kg. In some embodiments, the dry matter basis of copper is less than 12.5 mg/kg. In some embodiments, the dry matter basis of copper is greater than 12.5 mg/kg. In some embodiments, the dry matter basis of copper is 15 mg/kg. In some embodiments, the dry matter basis of copper is less than 15 mg/kg. In some embodiments, the dry matter basis of copper is greater than 15 mg/kg. In some embodiments, the dry matter basis of copper is 17.5 mg/kg. In some embodiments, the dry matter basis of copper is less than 17.5 mg/kg. In some embodiments, the dry matter basis of copper is greater than 17.5 mg/kg. In some embodiments, the dry matter basis of copper is about 2.5 mg/kg to about 17.5 mg/kg. In some embodiments, the dry matter basis of copper is about 5 mg/kg to about 15 mg/kg. In some embodiments, the dry matter basis of copper is about 7.5 mg/kg to about 7.5 mg/kg. In some embodiments, the dry matter basis of manganese is 4.5 mg/kg. In some embodiments, the dry matter basis of manganese is less than 4.5 mg/kg. In some embodiments, the dry matter basis of manganese is greater than 4.5 mg/kg. In some embodiments, the dry matter basis of manganese is 5 mg/kg. In some embodiments, the dry matter basis of manganese is less than 5 mg/kg. In some embodiments, the dry matter basis of manganese is greater than 5 mg/kg. In some embodiments, the dry matter basis of manganese is 5.5 mg/kg. In some embodiments, the dry matter basis of manganese is less than 5.5 mg/kg. In some embodiments, the dry matter basis of manganese is greater than 5.5 mg/kg. In some embodiments, the dry matter basis of manganese is 6 mg/kg. In some embodiments, the dry matter basis of manganese is less than 6 mg/kg. In some embodiments, the dry matter basis of manganese is greater than 6 mg/kg. In some embodiments, the dry matter basis of manganese is 6.5 mg/kg. In some embodiments, the dry matter basis of manganese is less than 6.5 mg/kg. In some embodiments, the dry matter basis of manganese is greater than 6.5 mg/kg. In some embodiments, the dry matter basis of manganese is 7 mg/kg. In some embodiments, the dry matter basis of manganese is less than 7 mg/kg. In some embodiments, the dry matter basis of manganese is greater than 7 mg/kg. In some embodiments, the dry matter basis of manganese is 7.5 mg/kg. In some embodiments, the dry matter basis of manganese is less than 7.5 mg/kg. In some embodiments, the dry matter basis of manganese is greater than 7.5 mg/kg. In some embodiments, the dry matter basis of manganese is 8 mg/kg. In some embodiments, the dry matter basis of manganese is less than 8 mg/kg. In some embodiments, the dry matter basis of manganese is greater than 8 mg/kg. In some embodiments, the dry matter basis of manganese is 8.5 mg/kg. In some embodiments, the dry matter basis of manganese is less than 8.5 mg/kg. In some embodiments, the dry matter basis of manganese is greater than 8.5 mg/kg. In some embodiments, the dry matter basis of manganese is about 4.5 mg/kg to about 8.5 mg/kg. In some embodiments, the dry matter basis of manganese is about 5 mg/kg to about 7.5 mg/kg. In some embodiments, the dry matter basis of manganese is about 7 mg/kg to about 7.5 mg/kg. In some embodiments, the dry matter basis of manganese is about 7 mg/kg to about 8 mg/kg. In some embodiments, the dry matter basis of zinc is 65 mg/kg. In some embodiments, the dry matter basis of zinc is less than 65 mg/kg. In some embodiments, the dry matter basis of zinc is greater than 65 mg/kg. In some embodiments, the dry matter basis of zinc is 70 mg/kg. In some embodiments, the dry matter basis of zinc is less than 70 mg/kg. In some embodiments, the dry matter basis of zinc is greater than 70 mg/kg. In some embodiments, the dry matter basis of zinc is 75 mg/kg. In some embodiments, the dry matter basis of zinc is less than 75 mg/kg. In some embodiments, the dry matter basis of zinc is greater than 75 mg/kg. In some embodiments, the dry matter basis of zinc is 80 mg/kg. In some embodiments, the dry matter basis of zinc is less than 80 mg/kg. In some embodiments, the dry matter basis of zinc is greater than 80 mg/kg. In some embodiments, the dry matter basis of zinc is 85 mg/kg. In some embodiments, the dry matter basis of zinc is less than 85 mg/kg. In some embodiments, the dry matter basis of zinc is greater than 85 mg/kg. In some embodiments, the dry matter basis of zinc is 90 mg/kg. In some embodiments, the dry matter basis of zinc is less than 90 mg/kg. In some embodiments, the dry matter basis of zinc is greater than 90 mg/kg. In some embodiments, the dry matter basis of zinc is 95 mg/kg. In some embodiments, the dry matter basis of zinc is less than 95 mg/kg. In some embodiments, the dry matter basis of zinc is greater than 95 mg/kg. In some embodiments, the dry matter basis of zinc is 100 mg/kg. In some embodiments, the dry matter basis of zinc is less than 100 mg/kg. In some embodiments, the dry matter basis of zinc is greater than 100 mg/kg. In some embodiments, the dry matter basis of zinc is 105 mg/kg. In some embodiments, the dry matter basis of zinc is less than 105 mg/kg. In some embodiments, the dry matter basis of zinc is greater than 105 mg/kg. In some embodiments, the dry matter basis of zinc is 110 mg/kg. In some embodiments, the dry matter basis of zinc is less than 110 mg/kg. In some embodiments, the dry matter basis of zinc is greater than 100 mg/kg. In some embodiments, the dry matter basis of zinc is about 65 mg/kg to about 110 mg/kg. In some embodiments, the dry matter basis of zinc is about 70 mg/kg to about 105 mg/kg. In some embodiments, the dry matter basis of zinc is about 75 mg/kg to about 100 mg/kg. In some embodiments, the dry matter basis of zinc is about 70 mg/kg to about 80 mg/kg. In some embodiments, the dry matter basis of zinc is about 75 mg/kg to about 85 mg/kg. In some embodiments, the dry matter basis of zinc is about 95 mg/kg to about 105 mg/kg. In some embodiments, the dry matter basis of iodine is 0.2 mg/kg. In some embodiments, the dry matter basis of iodine is less than 0.2 mg/kg. In some embodiments, the dry matter basis of iodine is greater than 0.2 mg/kg. In some embodiments, the dry matter basis of iodine is 0.6 mg/kg. In some embodiments, the dry matter basis of iodine is less than 0.6 mg/kg. In some embodiments, the dry matter basis of iodine is greater than 0.6 mg/kg. In some embodiments, the dry matter basis of iodine is 1 mg/kg. In some embodiments, the dry matter basis of iodine is less than 1 mg/kg. In some embodiments, the dry matter basis of iodine is greater than 1 mg/kg. In some embodiments, the dry matter basis of iodine is 1.4 mg/kg. In some embodiments, the dry matter basis of iodine is less than 1.4 mg/kg. In some embodiments, the dry matter basis of iodine is greater than 1.4 mg/kg. In some embodiments, the dry matter basis of iodine is 1.8 mg/kg. In some embodiments, the dry matter basis of iodine is less than 1.8 mg/kg. In some embodiments, the dry matter basis of iodine is greater than 1.8 mg/kg. In some embodiments, the dry matter basis of iodine is 2.2 mg/kg. In some embodiments, the dry matter basis of iodine is less than 2.2 mg/kg. In some embodiments, the dry matter basis of iodine is greater than 2.2 mg/kg. In some embodiments, the dry matter basis of iodine is about 0.2 mg/kg to about 2.2 mg/kg. In some embodiments, the dry matter basis of iodine is about 0.6 mg/kg to about 1.8 mg/kg. In some embodiments, the dry matter basis of iodine is about 0.9 mg/kg to about 1.1 mg/kg. In some embodiments, the dry matter basis of selenium is 0.2 mg/kg. In some embodiments, the dry matter basis of selenium is less than 0.2 mg/kg. In some embodiments, the dry matter basis of selenium is greater than 0.2 mg/kg. In some embodiments, the dry matter basis of selenium is 0.25 mg/kg. In some embodiments, the dry matter basis of selenium is less than 0.25 mg/kg. In some embodiments, the dry matter basis of selenium is greater than 0.25 mg/kg. In some embodiments, the dry matter basis of selenium is 0.3 mg/kg. In some embodiments, the dry matter basis of selenium is less than 0.3 mg/kg. In some embodiments, the dry matter basis of selenium is greater than 0.3 mg/kg. In some embodiments, the dry matter basis of selenium is 0.35 mg/kg. In some embodiments, the dry matter basis of selenium is less than 0.35 mg/kg. In some embodiments, the dry matter basis of selenium is greater than 0.35 mg/kg. In some embodiments, the dry matter basis of selenium is 0.4 mg/kg. In some embodiments, the dry matter basis of selenium is less than 0.4 mg/kg. In some embodiments, the dry matter basis of selenium is greater than 0.4 mg/kg. In some embodiments, the dry matter basis of selenium is 0.45 mg/kg. In some embodiments, the dry matter basis of selenium is less than 0.45 mg/kg. In some embodiments, the dry matter basis of selenium is greater than 0.45 mg/kg. In some embodiments, the dry matter basis of selenium is about 0.2 mg/kg to about 0.45 mg/kg. In some embodiments, the dry matter basis of selenium is about 0.25 mg/kg to about 0.35 mg/kg. In some embodiments, the dry matter basis of selenium is about 0.25 mg/kg to about 0.4 mg/kg. In some embodiments, the dry matter basis of selenium is about 0.3 mg/kg to about 0.4 mg/kg. In some embodiments, the dry matter basis of vitamin K is 0.05 mg/kg. In some embodiments, the dry matter basis of vitamin K is less than 0.05 mg/kg. In some embodiments, the dry matter basis of vitamin K is greater than 0.05 mg/kg. In some embodiments, the dry matter basis of vitamin K is 0.08 mg/kg. In some embodiments, the dry matter basis of vitamin K is less than 0.08 mg/kg. In some embodiments, the dry matter basis of vitamin K is greater than 0.08 mg/kg. In some embodiments, the dry matter basis of vitamin K is 0.1 mg/kg. In some embodiments, the dry matter basis of vitamin K is less than 0.1 mg/kg. In some embodiments, the dry matter basis of vitamin K is greater than 0.1 mg/kg. In some embodiments, the dry matter basis of vitamin K is 0.13 mg/kg. In some embodiments, the dry matter basis of vitamin K is less than 0.13 mg/kg. In some embodiments, the dry matter basis of vitamin K is greater than 0.13 mg/kg. In some embodiments, the dry matter basis of vitamin K is 0.15 mg/kg. In some embodiments, the dry matter basis of vitamin K is less than 0.15 mg/kg. In some embodiments, the dry matter basis of vitamin K is greater than 0.15 mg/kg. In some embodiments, the dry matter basis of vitamin K is about 0.05 mg/kg to about 0.15 mg/kg. In some embodiments, the dry matter basis of vitamin K is about 0.08 mg/kg to about 0.13 mg/kg. In some embodiments, the dry matter basis of vitamin A is 3000 IU/kg. In some embodiments, the dry matter basis of vitamin A is less than 3000 IU/kg. In some embodiments, the dry matter basis of vitamin A is greater than 3000 IU/kg. In some embodiments, the dry matter basis of vitamin A is 4000 IU/kg. In some embodiments, the dry matter basis of vitamin A is less than 4000 IU/kg. In some embodiments, the dry matter basis of vitamin A is greater than 4000 IU/kg. In some embodiments, the dry matter basis of vitamin A is 5000 IU/kg. In some embodiments, the dry matter basis of vitamin A is less than 5000 IU/kg. In some embodiments, the dry matter basis of vitamin A is greater than 5000 IU/kg. In some embodiments, the dry matter basis of vitamin A is 6000 IU/kg. In some embodiments, the dry matter basis of vitamin A is less than 6000 IU/kg. In some embodiments, the dry matter basis of vitamin A is greater than 6000 IU/kg. In some embodiments, the dry matter basis of vitamin A is 7000 IU/kg. In some embodiments, the dry matter basis of vitamin A is less than 7000 IU/kg. In some embodiments, the dry matter basis of vitamin A is greater than 7000 IU/kg. In some embodiments, the dry matter basis of vitamin A is about 3000 IU/kg to about 7000 IU/kg. In some embodiments, the dry matter basis of vitamin A is about 3000 IU/kg to about 4000 IU/kg. In some embodiments, the dry matter basis of vitamin A is about 4000 IU/kg to about 6000 IU/kg. In some embodiments, the dry matter basis of vitamin A is about 6000 IU/kg to about 7000 IU/kg. In some embodiments, the dry matter basis of vitamin D is 200 IU/kg. In some embodiments, the dry matter basis of vitamin D is less than 200 IU/kg. In some embodiments, the dry matter basis of vitamin D is greater than 200 IU/kg. In some embodiments, the dry matter basis of vitamin D is 300 IU/kg. In some embodiments, the dry matter basis of vitamin D is less than 300 IU/kg. In some embodiments, the dry matter basis of vitamin D is greater than 300 IU/kg. In some embodiments, the dry matter basis of vitamin D is 400 IU/kg. In some embodiments, the dry matter basis of vitamin D is less than 400 IU/kg. In some embodiments, the dry matter basis of vitamin D is greater than 400 IU/kg. In some embodiments, the dry matter basis of vitamin D is 500 IU/kg. In some embodiments, the dry matter basis of vitamin D is less than 500 IU/kg. In some embodiments, the dry matter basis of vitamin D is greater than 500 IU/kg. In some embodiments, the dry matter basis of vitamin D is 600 IU/kg. In some embodiments, the dry matter basis of vitamin D is less than 600 IU/kg. In some embodiments, the dry matter basis of vitamin D is greater than 600 IU/kg. In some embodiments, the dry matter basis of vitamin D is about 200 IU/kg to about 600 IU/kg. In some embodiments, the dry matter basis of vitamin D is about 200 IU/kg to about 300 IU/kg. In some embodiments, the dry matter basis of vitamin D is about 300 IU/kg to about 600 IU/kg. In some embodiments, the dry matter basis of vitamin D is about 400 IU/kg to about 600 IU/kg. In some embodiments, the dry matter basis of vitamin E is 30 IU/kg. In some embodiments, the dry matter basis of vitamin E is less than 30 IU/kg. In some embodiments, the dry matter basis of vitamin E is greater than 30 IU/kg. In some embodiments, the dry matter basis of vitamin E is 35 IU/kg. In some embodiments, the dry matter basis of vitamin E is less than 35 IU/kg. In some embodiments, the dry matter basis of vitamin E is greater than 35 IU/kg. In some embodiments, the dry matter basis of vitamin E is 40 IU/kg. In some embodiments, the dry matter basis of vitamin E is less than 40 IU/kg. In some embodiments, the dry matter basis of vitamin E is greater than 40 IU/kg. In some embodiments, the dry matter basis of vitamin E is 45 IU/kg. In some embodiments, the dry matter basis of vitamin E is less than 45 IU/kg. In some embodiments, the dry matter basis of vitamin E is greater than 45 IU/kg. In some embodiments, the dry matter basis of vitamin E is 50 IU/kg. In some embodiments, the dry matter basis of vitamin E is less than 50 IU/kg. In some embodiments, the dry matter basis of vitamin E is greater than 50 IU/kg. In some embodiments, the dry matter basis of vitamin E is 55 IU/kg. In some embodiments, the dry matter basis of vitamin E is less than 55 IU/kg. In some embodiments, the dry matter basis of vitamin E is greater than 55 IU/kg. In some embodiments, the dry matter basis of vitamin E is 60 IU/kg. In some embodiments, the dry matter basis of vitamin E is less than 60 IU/kg. In some embodiments, the dry matter basis of vitamin E is greater than 60 IU/kg. In some embodiments, the dry matter basis of vitamin E is about 30 IU/kg to about 60 IU/kg. In some embodiments, the dry matter basis of vitamin E is about 35 IU/kg to about 55 IU/kg. In some embodiments, the dry matter basis of vitamin E is about 45 IU/kg to about 55 IU/kg. In some embodiments, the dry matter basis of vitamin E is about 35 IU/kg to about 45 IU/kg. In some embodiments, the dry matter basis of vitamin E is about 40 IU/kg to about 50 IU/kg. In some embodiments, the dry matter basis of thiamine is 2 mg/kg. In some embodiments, the dry matter basis of thiamine is less than 2 mg/kg. In some embodiments, the dry matter basis of thiamine is greater than 2 mg/kg. In some embodiments, the dry matter basis of thiamine is 2.5 mg/kg. In some embodiments, the dry matter basis of thiamine is less than 2.5 mg/kg. In some embodiments, the dry matter basis of thiamine is greater than 2.5 mg/kg. In some embodiments, the dry matter basis of thiamine is 3 mg/kg. In some embodiments, the dry matter basis of thiamine is less than 3 mg/kg. In some embodiments, the dry matter basis of thiamine is greater than 3 mg/kg. In some embodiments, the dry matter basis of thiamine is 3.5 mg/kg. In some embodiments, the dry matter basis of thiamine is less than 3.5 mg/kg. In some embodiments, the dry matter basis of thiamine is greater than 3.5 mg/kg. In some embodiments, the dry matter basis of thiamine is 4 mg/kg. In some embodiments, the dry matter basis of thiamine is less than 4 mg/kg. In some embodiments, the dry matter basis of thiamine is greater than 4 mg/kg. In some embodiments, the dry matter basis of thiamine is 4.5 mg/kg. In some embodiments, the dry matter basis of thiamine is less than 4.5 mg/kg. In some embodiments, the dry matter basis of thiamine is greater than 4.5 mg/kg. In some embodiments, the dry matter basis of thiamine is 5 mg/kg. In some embodiments, the dry matter basis of thiamine is less than 5 mg/kg. In some embodiments, the dry matter basis of thiamine is greater than 5 mg/kg. In some embodiments, the dry matter basis of thiamine is 5.5 mg/kg. In some embodiments, the dry matter basis of thiamine is less than 5.5 mg/kg. In some embodiments, the dry matter basis of thiamine is greater than 5.5 mg/kg. In some embodiments, the dry matter basis of thiamine is 6 mg/kg. In some embodiments, the dry matter basis of thiamine is less than 6 mg/kg. In some embodiments, the dry matter basis of thiamine is greater than 6 mg/kg. In some embodiments, the dry matter basis of thiamine is about 2 mg/kg to about 6 mg/kg. In some embodiments, the dry matter basis of thiamine is about 2 mg/kg to about 3 mg/kg. In some embodiments, the dry matter basis of thiamine is about 2 mg/kg to about 2.5 mg/kg. In some embodiments, the dry matter basis of thiamine is about 3 mg/kg to about 5 mg/kg. In some embodiments, the dry matter basis of thiamine is about 5 mg/kg to about 6 mg/kg. In some embodiments, the dry matter basis of thiamine is about 5.5 mg/kg to about 6 mg/kg. In some embodiments, the dry matter basis of riboflavin is 3.5 mg/kg. In some embodiments, the dry matter basis of riboflavin is less than 3.5 mg/kg. In some embodiments, the dry matter basis of riboflavin is greater than 3.5 mg/kg. In some embodiments, the dry matter basis of riboflavin is 4 mg/kg. In some embodiments, the dry matter basis of riboflavin is less than 4 mg/kg. In some embodiments, the dry matter basis of riboflavin is greater than 4 mg/kg. In some embodiments, the dry matter basis of riboflavin is 4.5 mg/kg. In some embodiments, the dry matter basis of riboflavin is less than 4.5 mg/kg. In some embodiments, the dry matter basis of riboflavin is greater than 4.5 mg/kg. In some embodiments, the dry matter basis of riboflavin is 5 mg/kg. In some embodiments, the dry matter basis of riboflavin is less than 5 mg/kg. In some embodiments, the dry matter basis of riboflavin is greater than 5 mg/kg. In some embodiments, the dry matter basis of riboflavin is 5.5 mg/kg. In some embodiments, the dry matter basis of riboflavin is less than 5.5 mg/kg. In some embodiments, the dry matter basis of riboflavin is greater than 5.5 mg/kg. In some embodiments, the dry matter basis of riboflavin is about 3.5 mg/kg to about 5.5 mg/kg. In some embodiments, the dry matter basis of riboflavin is about 4 mg/kg to about 5 mg/kg. In some embodiments, the dry matter basis of riboflavin is about 3.5 mg/kg to about 4.5 mg/kg. In some embodiments, the dry matter basis of riboflavin is about 5 mg/kg to about 5.5 mg/kg. In some embodiments, the dry matter basis of pantothenic acid is 5 mg/kg. In some embodiments, the dry matter basis of pantothenic acid is less than 5 mg/kg. In some embodiments, the dry matter basis of pantothenic acid is greater than 5 mg/kg. In some embodiments, the dry matter basis of pantothenic acid is 6 mg/kg. In some embodiments, the dry matter basis of pantothenic acid is less than 6 mg/kg. In some embodiments, the dry matter basis of pantothenic acid is greater than 6 mg/kg. In some embodiments, the dry matter basis of pantothenic acid is 7 mg/kg. In some embodiments, the dry matter basis of pantothenic acid is less than 7 mg/kg. In some embodiments, the dry matter basis of pantothenic acid is greater than 7 mg/kg. In some embodiments, the dry matter basis of pantothenic acid is 8 mg/kg. In some embodiments, the dry matter basis of pantothenic acid is less than 8 mg/kg. In some embodiments, the dry matter basis of pantothenic acid is greater than 8 mg/kg. In some embodiments, the dry matter basis of pantothenic acid is 9 mg/kg. In some embodiments, the dry matter basis of pantothenic acid is less than 9 mg/kg. In some embodiments, the dry matter basis of pantothenic acid is greater than 9 mg/kg. In some embodiments, the dry matter basis of pantothenic acid is 10 mg/kg. In some embodiments, the dry matter basis of pantothenic acid is less than 10 mg/kg. In some embodiments, the dry matter basis of pantothenic acid is greater than 10 mg/kg. In some embodiments, the dry matter basis of pantothenic acid is 11 mg/kg. In some embodiments, the dry matter basis of pantothenic acid is less than 11 mg/kg. In some embodiments, the dry matter basis of pantothenic acid is greater than 11 mg/kg. In some embodiments, the dry matter basis of pantothenic acid is 12 mg/kg. In some embodiments, the dry matter basis of pantothenic acid is less than 12 mg/kg. In some embodiments, the dry matter basis of pantothenic acid is greater than 12 mg/kg. In some embodiments, the dry matter basis of pantothenic acid is 13 mg/kg. In some embodiments, the dry matter basis of pantothenic acid is less than 13 mg/kg. In some embodiments, the dry matter basis of pantothenic acid is greater than 13 mg/kg. In some embodiments, the dry matter basis of pantothenic acid is about 5 mg/kg to about 13 mg/kg. In some embodiments, the dry matter basis of pantothenic acid is about 5 mg/kg to about 6 mg/kg. In some embodiments, the dry matter basis of pantothenic acid is about 12 mg/kg to about 13 mg/kg. In some embodiments, the dry matter basis of niacin is 10 mg/kg. In some embodiments, the dry matter basis of niacin is less than 10 mg/kg. In some embodiments, the dry matter basis of niacin is greater than 10 mg/kg. In some embodiments, the dry matter basis of niacin is 20 mg/kg. In some embodiments, the dry matter basis of niacin is less than 20 mg/kg. In some embodiments, the dry matter basis of niacin is greater than 20 mg/kg. In some embodiments, the dry matter basis of niacin is 30 mg/kg. In some embodiments, the dry matter basis of niacin is less than 30 mg/kg. In some embodiments, the dry matter basis of niacin is greater than 30 mg/kg. In some embodiments, the dry matter basis of niacin is 40 mg/kg. In some embodiments, the dry matter basis of niacin is less than 40 mg/kg. In some embodiments, the dry matter basis of niacin is greater than 40 mg/kg. In some embodiments, the dry matter basis of niacin is 50 mg/kg. In some embodiments, the dry matter basis of niacin is less than 50 mg/kg. In some embodiments, the dry matter basis of niacin is greater than 50 mg/kg. In some embodiments, the dry matter basis of niacin is 60 mg/kg. In some embodiments, the dry matter basis of niacin is less than 60 mg/kg. In some embodiments, the dry matter basis of niacin is greater than 60 mg/kg. In some embodiments, the dry matter basis of niacin is 70 mg/kg. In some embodiments, the dry matter basis of niacin is less than 70 mg/kg. In some embodiments, the dry matter basis of niacin is greater than 70 mg/kg. In some embodiments, the dry matter basis of niacin is about 10 mg/kg to about 70 mg/kg. In some embodiments, the dry matter basis of niacin is about 10 mg/kg to about 20 mg/kg. In some embodiments, the dry matter basis of niacin is about 50 mg/kg to about 70 mg/kg. In some embodiments, the dry matter basis of pyridoxine is 1 mg/kg. In some embodiments, the dry matter basis of pyridoxine is less than 1 mg/kg. In some embodiments, the dry matter basis of pyridoxine is greater than 1 mg/kg. In some embodiments, the dry matter basis of pyridoxine is 1.5 mg/kg. In some embodiments, the dry matter basis of pyridoxine is less than 1.5 mg/kg. In some embodiments, the dry matter basis of pyridoxine is greater than 1.5 mg/kg. In some embodiments, the dry matter basis of pyridoxine is 2 mg/kg. In some embodiments, the dry matter basis of pyridoxine is less than 2 mg/kg. In some embodiments, the dry matter basis of pyridoxine is greater than 2 mg/kg. In some embodiments, the dry matter basis of pyridoxine is 2.5 mg/kg. In some embodiments, the dry matter basis of pyridoxine is less than 2.5 mg/kg. In some embodiments, the dry matter basis of pyridoxine is greater than 2.5 mg/kg. In some embodiments, the dry matter basis of pyridoxine is 3 mg/kg. In some embodiments, the dry matter basis of pyridoxine is less than 3 mg/kg. In some embodiments, the dry matter basis of pyridoxine is greater than 3 mg/kg. In some embodiments, the dry matter basis of pyridoxine is 3.5 mg/kg. In some embodiments, the dry matter basis of pyridoxine is less than 3.5 mg/kg. In some embodiments, the dry matter basis of pyridoxine is greater than 3.5 mg/kg. In some embodiments, the dry matter basis of pyridoxine is 4 mg/kg. In some embodiments, the dry matter basis of pyridoxine is less than 4 mg/kg. In some embodiments, the dry matter basis of pyridoxine is greater than 4 mg/kg. In some embodiments, the dry matter basis of pyridoxine is 4.5 mg/kg. In some embodiments, the dry matter basis of pyridoxine is less than 4.5 mg/kg. In some embodiments, the dry matter basis of pyridoxine is greater than 4.5 mg/kg. In some embodiments, the dry matter basis of pyridoxine is about 1 mg/kg to about 4.5 mg/kg. In some embodiments, the dry matter basis of pyridoxine is about 1 mg/kg to about 2 mg/kg. In some embodiments, the dry matter basis of pyridoxine is about 3.5 mg/kg to about 4.5 mg/kg. In some embodiments, the dry matter basis of folic acid is 0.2 mg/kg. In some embodiments, the dry matter basis of folic acid is less than 0.2 mg/kg. In some embodiments, the dry matter basis of folic acid is greater than 0.2 mg/kg. In some embodiments, the dry matter basis of folic acid is 0.3 mg/kg. In some embodiments, the dry matter basis of folic acid is less than 0.3 mg/kg. In some embodiments, the dry matter basis of folic acid is greater than 0.3 mg/kg. In some embodiments, the dry matter basis of folic acid is 0.4 mg/kg. In some embodiments, the dry matter basis of folic acid is less than 0.4 mg/kg. In some embodiments, the dry matter basis of folic acid is greater than 0.4 mg/kg. In some embodiments, the dry matter basis of folic acid is 0.5 mg/kg. In some embodiments, the dry matter basis of folic acid is less than 0.5 mg/kg. In some embodiments, the dry matter basis of folic acid is greater than 0.5 mg/kg. In some embodiments, the dry matter basis of folic acid is 0.6 mg/kg. In some embodiments, the dry matter basis of folic acid is less than 0.6 mg/kg. In some embodiments, the dry matter basis of folic acid is greater than 0.6 mg/kg. In some embodiments, the dry matter basis of folic acid is 0.7 mg/kg. In some embodiments, the dry matter basis of folic acid is less than 0.7 mg/kg. In some embodiments, the dry matter basis of folic acid is greater than 0.7 mg/kg. In some embodiments, the dry matter basis of folic acid is 0.8 mg/kg. In some embodiments, the dry matter basis of folic acid is less than 0.8 mg/kg. In some embodiments, the dry matter basis of folic acid is greater than 0.8 mg/kg. In some embodiments, the dry matter basis of folic acid is 0.9 mg/kg. In some embodiments, the dry matter basis of folic acid is less than 0.9 mg/kg. In some embodiments, the dry matter basis of folic acid is greater than 0.9 mg/kg. In some embodiments, the dry matter basis of folic acid is about 0.2 mg/kg to about 0.9 mg/kg. In some embodiments, the dry matter basis of folic acid is about 0.2 mg/kg to about 0.3 mg/kg. In some embodiments, the dry matter basis of folic acid is about 0.7 mg/kg to about 0.9 mg/kg. In some embodiments, the dry matter basis of vitamin $B_{12}$ is 0.015 mg/kg. In some embodiments, the dry matter basis of vitamin $B_{12}$ is less than 0.015 mg/kg. In some embodiments, the dry matter basis of vitamin $B_{12}$ is greater than 0.015 mg/kg. In some embodiments, the dry matter basis of vitamin $B_{12}$ is 0.02 mg/kg. In some embodiments, the dry matter basis of vitamin $B_{12}$ is less than 0.02 mg/kg. In some embodiments, the dry matter basis of vitamin $B_{12}$ is greater than 0.02 mg/kg. In some embodiments, the dry matter basis of vitamin $B_{12}$ is 0.025 mg/kg. In some embodiments, the dry matter basis of vitamin $B_{12}$ is less than 0.025 mg/kg. In some embodiments, the dry matter basis of vitamin $B_{12}$ is greater than 0.025 mg/kg. In some embodiments, the dry matter basis of vitamin $B_{12}$ is about 0.015 mg/kg to about 0.025 mg/kg. In some embodiments, the dry matter basis of vitamin $B_{12}$ is about 0.02 mg/kg to about 0.025 mg/kg. In some embodiments, the dry matter basis of choline is 1000 mg/kg. In some embodiments, the dry matter basis of choline is less than 1000 mg/kg. In some embodiments, the dry matter basis of choline is greater than 1000 mg/kg. In some embodiments, the dry matter basis of choline is 1250 mg/kg. In some embodiments, the dry matter basis of choline is less than 1250 mg/kg. In some embodiments, the dry matter basis of choline is greater than 1250 mg/kg. In some embodiments, the dry matter basis of choline is 1500 mg/kg. In some embodiments, the dry matter basis of choline is less than 1500 mg/kg. In some embodiments, the dry matter basis of choline is greater than 1500 mg/kg. In some embodiments, the dry matter basis of choline is 1750 mg/kg. In some embodiments, the dry matter basis of choline is less than 1750 mg/kg. In some embodiments, the dry matter basis of choline is greater than 1750 mg/kg. In some embodiments, the dry matter basis of choline is 2000 mg/kg. In some embodiments, the dry matter basis of choline is less than 2000 mg/kg. In some embodiments, the dry matter basis of choline is greater than 2000 mg/kg. In some embodiments, the dry matter basis of choline is 2250 mg/kg. In some embodiments, the dry matter basis of choline is less than 2250 mg/kg. In some embodiments, the dry matter basis of choline is greater than 2250 mg/kg. In some embodiments, the dry matter basis of choline is 2500 mg/kg. In some embodiments, the dry matter basis of choline is less than 2500 mg/kg. In some embodiments, the dry matter basis of choline is greater than 2500 mg/kg. In some embodiments, the dry matter basis of choline is 2750 mg/kg. In some embodiments, the dry matter basis of choline is less than 2750 mg/kg. In some embodiments, the dry matter basis of choline is greater than 2750 mg/kg. In some embodiments, the dry matter basis of choline is about 1000 mg/kg to about 2750 mg/kg. In some embodiments, the dry matter basis of choline is about 1250 mg/kg to about 2500 mg/kg. In some embodiments, the dry matter basis of choline is about 1250 mg/kg to about 1500 mg/kg. In some embodiments, the dry matter basis of choline is about 2250 mg/kg to about 2500 mg/kg. In some embodiments, the minimum percentage of taurine is 0.06%. In some embodiments, the minimum percentage of taurine is less than 0.06%. In some embodiments, the minimum percentage of taurine is greater than 0.06%. In some embodiments, the minimum percentage of taurine is 0.08%. In some embodiments, the minimum percentage of taurine is less than 0.08%. In some embodiments, the minimum percentage of taurine is greater than 0.08%. In some embodiments, the minimum percentage of taurine is 0.1%. In some embodiments, the minimum percentage of taurine is less than 0.1%. In some embodiments, the minimum percentage of taurine is greater than 0.1%. In some embodiments, the minimum percentage of taurine is 0.2%. In some embodiments, the minimum percentage of taurine is less than 0.2%. In some embodiments, the minimum percentage of taurine is greater than 0.2%. In some embodiments, the minimum percentage of taurine is 0.3%. In some embodiments, the minimum percentage of taurine is less than 0.3%. In some embodiments, the minimum percentage of taurine is greater than 0.3%. In some embodiments, the minimum percentage of taurine is 0.4%. In some embodiments, the minimum percentage of taurine is less than 0.4%. In some embodiments, the minimum percentage of taurine is greater than 0.4%. In some embodiments, the percentage of taurine is about 0.06% to about 0.4%. In some embodiments, the percentage of taurine is about 0.08% to about 0.3%. In some embodiments, the percentage of taurine is about 0.1% to about 0.3%. In some embodiments, the percentage of taurine is about 0.1% to about 0.2%. In some embodiments, the percentage of taurine is about 0.08% to about 0.2%. In some embodiments, the percentage of taurine is about 0.1% to about 0.3%. Some diets can also contain increases or decreases in the minimum percent in the diet as well as the addition of other compounds. For example, vitamin K is beneficial in the feline diet if that diet contains more than 25% fish based on dry matter.

Disclosed herein are custom or semi-custom food products comprising one or more additives or enhancements as compared with a standard food. A "standard" food as used herein, refers to food for a given animal consistent with guidelines approved by a standard-setting body. For example, for canines, the food may follow the guidelines of the Association of American Feed Control Officials (AAFCO), which provides the minimum dry weight percentages of macronutrients for an adult canine as 18% protein and 5.5% fat and for a juvenile canine as 22.5% protein and 8.5% fat. For felines, the food may follow the guidelines of the AAFCO, which provides the minimum dry weight percentages of macronutrients for an adult feline as 26% protein and 9% fat and for a juvenile feline as 30% protein and 9% fat.

In some embodiments, a supplement is recommended. In some embodiments, the recommended supplement is an antioxidant and immune supplement. In some embodiments, the active ingredients of the antioxidant and immune supplement comprise β-carotene, bovine colostrum, lutein, *Enterococcus faecium*, or any combination thereof. In some embodiments, the amount of β-carotene in the antioxidant and immune supplement as fed is about 10,000 to about 50,000 mg/kg. In some embodiments, the amount of β-carotene in the antioxidant and immune supplement as fed is about 20,000 to about 40,000 mg/kg. In some embodiments, the amount of β-carotene in the antioxidant and immune supplement as fed is about 30,000 mg/kg. In some embodiments, the amount of lutein in the antioxidant and immune supplement as fed is about 500 to about 5,000 mg/kg. In some embodiments, the amount of lutein in the antioxidant and immune supplement as fed is about 1,000 to about 4,000 mg/kg. In some embodiments, the amount of lutein in the antioxidant and immune supplement as fed is about 2,000 to about 3,000 mg/kg. In some embodiments, the amount of lutein in the antioxidant and immune supplement as fed is about 2,500 mg/kg. In some embodiments, *Enterococcus faecium* is a probiotic. In some embodiments, the amount of probiotic in the antioxidant and immune supplement as fed is about $0.5 \times 10^8$ to about $5.0 \times 10^8$ CFU/g. In some embodiments, the amount of probiotic in the antioxidant and immune supplement as fed is about $1.0 \times 10^8$ to about $4.0 \times 10^8$ CFU/g. In some embodiments, the amount of probiotic in the antioxidant and immune supplement as fed is about $2.0 \times 10^8$ to about $3.0 \times 10^8$ CFU/g. In some embodiments, the amount of probiotic in the antioxidant and immune supplement as fed is about $2.5 \times 10^8$. In some embodiments, the amount of bovine colostrum in the antioxidant and immune supplement as fed is about 120,000 to about 50,000 mg/kg. In some embodiments, the amount of bovine colostrum in the antioxidant and immune supplement as fed is about 100,000 to about 70,000 mg/kg. In some embodiments, the amount of bovine colostrum in the antioxidant and immune supplement as fed is about 95,000 to about 80,000 mg/kg. In some embodiments, the amount of bovine colostrum in the antioxidant and immune supplement as fed is about 90,000 to about 85,000 mg/kg. In some embodiments, the amount of bovine colostrum in the antioxidant and immune supplement as fed is about 87,000 mg/kg.

In some embodiments, the recommended supplement is an anxiety supplement. In some embodiments, the active ingredients for the anxiety supplement comprise α-casozepine, L-theanine, *Lactiplantibacillus plantarum* PS-128, or any combination thereof. In some embodiments, the amount of α-casozepine in the anxiety supplement as fed is about 250 to about 150 mg/g. In some embodiments, the amount of α-casozepine in the anxiety supplement as fed is about 225 to about 175 mg/g. In some embodiments, the amount of α-casozepine in the anxiety supplement as fed is about 215 to about 190 mg/g. In some embodiments, the amount of α-casozepine in the anxiety supplement as fed is about 210 to about 200 mg/g. In some embodiments, the amount of α-casozepine in the anxiety supplement as fed is about 210 to about 205 mg/g. In some embodiments, the amount of α-casozepine in the anxiety supplement as fed is about 209 mg/g. In some embodiments, the amount of L-theanine in the anxiety supplement as fed is about 150 to about 50 mg/g. In some embodiments, the amount of L-theanine in the anxiety supplement as fed is about 125 to about 75 mg/g. In some embodiments, the amount of L-theanine in the anxiety supplement as fed is about 110 to about 90 mg/g. In some embodiments, the amount of L-theanine in the anxiety supplement as fed is about 105 to about 95 mg/g. In some embodiments, the amount of L-theanine in the anxiety supplement as fed is about 101 to about 99 mg/g. In some embodiments, the amount of L-theanine in the anxiety supplement as fed is about 100 mg/g. In some embodiments, *Lactiplantibacillus plantarum* PS-128 is the probiotic. In some embodiments, the amount of probiotic in the anxiety supplement as fed is about $2.0 \times 10^{10}$ to about $1.0 \times 10^{10}$ CFU/g. In some embodiments, the amount of probiotic in the anxiety supplement as fed is about $1.75 \times 10^{10}$ to about $1.25 \times 10^{10}$ CFU/g. In some embodiments, the amount of probiotic in the anxiety supplement as fed is about $1.50 \times 10^{10}$ to about $1.30 \times 10^{10}$ CFU/g. In some embodiments, the amount of probiotic in the anxiety supplement as fed is about $1.40 \times 10^{10}$ to about $1.30 \times 10^{10}$ CFU/g. In some embodiments, the amount of probiotic in the anxiety supplement as fed is about $1.38 \times 10^{10}$ to about $1.34 \times 10^{10}$ CFU/g. In some embodiments, the amount of probiotic in the anxiety supplement as fed is about $1.36 \times 10^{10}$ CFU/g.

In some embodiments, the recommended supplement is a B complex supplement. In some embodiments, the active ingredients for the B complex supplement comprises B vitamins. In some embodiments, the B vitamins comprise thiamin, riboflavin, pantothenic acid, niacin, pyridoxine, folic acid, vitamin B12, or any combination thereof. In some embodiments, the amount of thiamin in the B complex supplement as fed is about 100 to about 500 mg/kg. In some embodiments, the amount of thiamin in the B complex supplement as fed is about 200 to about 400 mg/kg. In some embodiments, the amount of thiamin in the B complex supplement as fed is about 250 to about 350 mg/kg. In some embodiments, the amount of thiamin in the B complex supplement as fed is about 300 to about 350 mg/kg. In some embodiments, the amount of thiamin in the B complex supplement as fed is about 300 to about 325 mg/kg. In some embodiments, the amount of thiamin in the B complex supplement as fed is about 334 mg/kg. In some embodiments, the amount of riboflavin in the B complex supplement as fed is about 100 to about 1,000 mg/kg. In some embodiments, the amount of riboflavin in the B complex supplement as fed is about 250 to about 750 mg/kg. In some embodiments, the amount of riboflavin in the B complex supplement as fed is about 400 to about 600 mg/kg. In some embodiments, the amount of riboflavin in the B complex supplement as fed is about 500 to about 600 mg/kg. In some embodiments, the amount of riboflavin in the B complex supplement as fed is about 525 to about 575 mg/kg. In some embodiments, the amount of riboflavin in the B complex supplement as fed is about 550 to about 575 mg/kg. In some embodiments, the amount of riboflavin in the B complex supplement as fed is about 570 mg/kg. In some embodiments, the amount of pantothenic acid in the B complex supplement as fed is about 2,000 to about 500 mg/kg. In some embodiments, the amount of pantothenic acid in the B complex supplement as fed is about 1,500 to about 750 mg/kg. In some embodiments, the amount of pantothenic acid in the B complex supplement as fed is about 1,250 to about 800 mg/kg. In some embodiments, the amount of pantothenic acid in the B complex supplement as fed is about 1,100 to about 900 mg/kg. In some embodiments, the amount of pantothenic acid in the B complex supplement as fed is about 1,063 mg/kg. In some embodiments, the amount of niacin in the B complex supplement as fed is about 5,000 to about 500 mg/kg. In some embodiments, the amount of niacin in the B complex supplement as fed is about 4,000 to about 750 mg/kg. In some embodiments, the amount of niacin in the B complex supplement as fed is about 3,000 to about 1,000 mg/kg. In some embodiments, the amount of niacin in the B complex supplement as fed is about 2,500 to about 1,500 mg/kg. In some embodiments, the amount of niacin in the B complex supplement as fed is about 2,250 to about 1,750 mg/kg. In some embodiments, the amount of niacin in the B complex supplement as fed is about 2,100 to about 1,900 mg/kg. In some embodiments, the amount of niacin in the B complex supplement as fed is about 1,955 mg/kg. In some embodiments, the amount of pyridoxine in the B complex supplement as fed is about 250 to about 50 mg/kg. In some embodiments, the amount of pyridoxine in the B complex supplement as fed is about 225 to about 75 mg/kg. In some embodiments, the amount of pyridoxine in the B complex supplement as fed is about 200 to about 100 mg/kg. In some embodiments, the amount of pyridoxine in the B complex supplement as fed is about 175 to about 150 mg/kg. In some embodiments, the amount of pyridoxine in the B complex supplement as fed is about 165 mg/kg. In some embodiments, the amount of folic acid in the B complex supplement as fed is about 10 to about 100 mg/kg. In some embodiments, the amount of folic acid in the B complex supplement as fed is about 20 to about 50 mg/kg. In some embodiments, the amount of folic acid in the B complex supplement as fed is about 25 to about 35 mg/kg. In some embodiments, the amount of folic acid in the B complex supplement as fed is about 28 to about 33 mg/kg. In some embodiments, the amount of folic acid in the B complex supplement as fed is about 32 mg/kg. In some embodiments, the amount of vitamin B12 in the B complex supplement as fed is about 1 to about 10 mg/kg. In some embodiments, the amount of vitamin B12 in the B complex supplement as fed is about 1.5 to about 7.5 mg/kg. In some embodiments, the amount of vitamin B12 in the B complex supplement as fed is about 2 to about 5 mg/kg. In some embodiments, the amount of vitamin B12 in the B complex supplement as fed is about 2.5 to about 3.5 mg/kg. In some embodiments, the amount of vitamin B12 in the B complex supplement as fed is about 2.75 to about 3.25 mg/kg. In some embodiments, the amount of vitamin B12 in the B complex supplement as fed is about 2.9 to about 3.1 mg/kg. In some embodiments, the amount of vitamin B12 in the B complex supplement as fed is about 2.95 mg/kg.

In some embodiments, the recommended supplement is a cardiac supplement. In some embodiments, the active ingredients in the cardiac supplement comprises L-carnitine, DL-methionine, L-cystine, Co-Q10, taurine, or any combination thereof. In some embodiments, the amount of L-carnitine in the cardiac supplement as fed is about 200,000 to about 50,000 mg/kg. In some embodiments, the amount of L-carnitine in the cardiac supplement as fed is about 175,000 to about 75,000 mg/kg. In some embodiments, the amount of L-carnitine in the cardiac supplement as fed is about 150,000 to about 100,000 mg/kg. In some embodiments, the amount of L-carnitine in the cardiac supplement as fed is about 140,000 to about 125,000 mg/kg. In some embodiments, the amount of L-carnitine in the cardiac supplement as fed is about 138,000 to about 128,000 mg/kg. In some embodiments, the amount of L-carnitine in the cardiac supplement as fed is about 136,000 to about 134,000 mg/kg. In some embodiments, the amount of L-carnitine in the cardiac supplement as fed is about 135,000 mg/kg. In some embodiments, the amount of DL-methionine in the cardiac supplement as fed is about 200,000 to about 50,000 mg/kg. In some embodiments, the amount of DL-methionine in the cardiac supplement as fed is about 175,000 to about 75,000 mg/kg. In some embodiments, the amount of DL-methionine in the cardiac supplement as fed is about 150,000 to about 100,000 mg/kg. In some embodiments, the amount of DL-methionine in the cardiac supplement as fed is about 130,000 to about 115,000 mg/kg. In some embodiments, the amount of DL-methionine in the cardiac supplement as fed is about 125,000 to about 120,000 mg/kg. In some embodiments, the amount of DL-methionine in the cardiac supplement as fed is about 122,000. In some embodiments, the amount of L-cystine in the cardiac supplement as fed is about 200,000 to about 50,000 mg/kg. In some embodiments, the amount of L-cystine in the cardiac supplement as fed is about 175,000 to about 75,000 mg/kg. In some embodiments, the amount of L-cystine in the cardiac supplement as fed is about 150,000 to about 100,000 mg/kg. In some embodiments, the amount of L-cystine in the cardiac supplement as fed is about 125,000 to about 115,000 mg/kg. In some embodiments, the amount of L-cystine in the cardiac supplement as fed is about 120,000 to about 116,000 mg/kg. In some embodiments, the amount of DL-methionine in the cardiac supplement as fed is about 118,500 mg/kg. In some embodiments, the amount of taurine in the cardiac supplement as fed is about 5,000 to about 50,000 mg/kg. In some embodiments, the amount of taurine in the cardiac supplement as fed is about 7,500 to about 40,000 mg/kg. In some embodiments, the amount of taurine in the cardiac supplement as fed is about 10,000 to about 30,000 mg/kg. In some embodiments, the amount of taurine in the cardiac supplement as fed is about 15,000 to about 25,000 mg/kg. In some embodiments, the amount of taurine in the cardiac supplement as fed is about 18,000 to about 23,000 mg/kg. In some embodiments, the amount of taurine in the cardiac supplement as fed is about 22,000 mg/kg. In some embodiments, the amount of Co-Q10 in the cardiac supplement as fed is about 100,000 to about 20,000 mg/kg. In some embodiments, the amount of Co-Q10 in the cardiac supplement as fed is about 90,000 to about 40,000 mg/kg. In some embodiments, the amount of Co-Q10 in the cardiac supplement as fed is about 80,000 to about 60,000 mg/kg. In some embodiments, the amount of Co-Q10 in the cardiac supplement as fed is about 70,000 to about 65,000 mg/kg. In some embodiments, the amount of Co-Q10 in the cardiac supplement as fed is about 69,600 mg/kg.

In some embodiments, the recommended supplement is a cognitive supplement. In some embodiments, the active ingredients in the cognitive supplement comprises eicosapentaenoic acid (EPA) and docosahexaenoic acid (DHA), acetyl-L-carnitine, α-lipoic acid, vitamin C, vitamin E, or any combination thereof. In some embodiments, the amount of EPA+DHA in the cognitive supplement as fed is about 100,000 to about 20,000 mg/kg. In some embodiments, the amount of EPA+DHA in the cognitive supplement as fed is about 90,000 to about 40,000 mg/kg. In some embodiments, the amount of EPA+DHA in the cognitive supplement as fed is about 80,000 to about 60,000 mg/kg. In some embodiments, the amount of EPA+DHA in the cognitive supplement as fed is about 78,000 to about 70,000 mg/kg. In some embodiments, the amount of EPA+DHA in the cognitive supplement as fed is about 77,000 to about 73,000 mg/kg. In some embodiments, the amount of EPA+DHA in the cognitive supplement as fed is about 75,000 mg/kg. In some embodiments, the amount of acetyl-L-carnitine in the cognitive supplement as fed is about 250,000 to about 25,000 mg/kg. In some embodiments, the amount of acetyl-L-carnitine in the cognitive supplement as fed is about 225,000 to about 50,000 mg/kg. In some embodiments, the amount of acetyl-L-carnitine in the cognitive supplement as fed is about 200,000 to about 75,000 mg/kg. In some embodiments, the amount of acetyl-L-carnitine in the cognitive supplement as fed is about 175,000 to about 100,000 mg/kg. In some embodiments, the amount of acetyl-L-carnitine in the cognitive supplement as fed is about 150,000 to about 110,000 mg/kg. In some embodiments, the amount of acetyl-L-carnitine in the cognitive supplement as fed is about 130,000 to about 120,000 mg/kg. In some embodiments, the amount of acetyl-L-carnitine in the cognitive supplement as fed is about 125,000 mg/kg. In some embodiments, the amount of α-lipoic acid in the cognitive supplement as fed is about 150,000 to about 10,000 mg/kg. In some embodiments, the amount of α-lipoic acid in the cognitive supplement as fed is about 125,000 to about 15,000 mg/kg. In some embodiments, the amount of α-lipoic acid in the cognitive supplement as fed is about 100,000 to about 25,000 mg/kg. In some embodiments, the amount of α-lipoic acid in the cognitive supplement as fed is about 75,000 to about 30,000 mg/kg. In some embodiments, the amount of α-lipoic acid in the cognitive supplement as fed is about 60,000 to about 40,000 mg/kg. In some embodiments, the amount of α-lipoic acid in the cognitive supplement as fed is about 50,000 mg/kg. In some embodiments, the amount of vitamin C in the cognitive supplement as fed is about 5,000 to about 50,000 mg/kg. In some embodiments, the amount of vitamin C in the cognitive supplement as fed is about 10,000 to about 40,000 mg/kg. In some embodiments, the amount of vitamin C in the cognitive supplement as fed is about 12,000 to about 30,000 mg/kg. In some embodiments, the amount of vitamin C in the cognitive supplement as fed is about 15,000 to about 25,000 mg/kg. In some embodiments, the amount of vitamin C in the cognitive supplement as fed is about 16,000 to about 20,000 mg/kg. In some embodiments, the amount of vitamin C in the cognitive supplement as fed is about 18,333 mg/kg. In some embodiments, the amount of vitamin E in the cognitive supplement as fed is about 10,000 to about 500 IU/kg. In some embodiments, the amount of vitamin E in the cognitive supplement as fed is about 5,000 to about 1,000 IU/kg. In some embodiments, the amount of vitamin E in the cognitive supplement as fed is about 3,500 to about 2,000 IU/kg. In some embodiments, the amount of vitamin E in the cognitive supplement as fed is about 3,000 to about 2,250 IU/kg. In some embodiments, the amount of vitamin E in the cognitive supplement as fed is about 2,900 to about 2,500 IU/kg. In some embodiments, the amount of vitamin E in the cognitive supplement as fed is about 2,750 IU/kg.

In some embodiments, the recommended supplement is a GI digestive supplement. In some embodiments, the active ingredients of the GI digestive supplement comprises pomegranate peel extract, *Bacillus coagulans*, *Enterococcus faecium*, L-glutamine, or any combination thereof. In some embodiments, the amount of pomegranate peel extract in the GI digestive supplement as fed is about 200,000 to about 25,000 mg/kg. In some embodiments, the amount of pomegranate peel extract in the GI digestive supplement as fed is about 175,000 to about 75,000 mg/kg. In some embodiments, the amount of pomegranate peel extract in the GI digestive supplement as fed is about 150,000 to about 125,000 mg/kg. In some embodiments, the amount of pomegranate peel extract in the GI digestive supplement as fed is about 140,000 to about 130,000 mg/kg. In some embodiments, the amount of pomegranate peel extract in the GI digestive supplement as fed is about 136,000 mg/kg. In some embodiments, *Bacillus coagulans* is a probiotic. In some embodiments, *Enterococcus faecium* is a probiotic. In some embodiments, the probiotic contains both *Bacillus coagulans* and *Enterococcus faecium*. In some embodiments, the ratio of *Bacillus coagulans* to *Enterococcus faecium* is about 0.20:1. In some embodiments, the ratio of *Bacillus coagulans* to *Enterococcus faecium* is about 0.25:1. In some embodiments, the ratio of *Bacillus coagulans* to *Enterococcus faecium* is about 0.30:1. In some embodiments, the ratio of *Bacillus coagulans* to *Enterococcus faecium* is about 0.35:1. In some embodiments, the ratio of *Bacillus coagulans* to *Enterococcus faecium* is about 0.39:1. In some embodiments, the amount of total probiotic in the GI digestive supplement as fed is about $2.0 \times 10^9$ to about $0.50 \times 10^9$ CFU/g. In some embodiments, the amount of total probiotic in the GI digestive supplement as fed is about $1.5 \times 10^9$ to about $0.75 \times 10^9$ CFU/g. In some embodiments, the amount of total probiotic in the GI digestive supplement as fed is about $1.25 \times 10^9$ to about $1.0 \times 10^9$ CFU/g. In some embodiments, the amount of total probiotic in the GI digestive supplement as fed is about $1.20 \times 10^9$ to about $1.05 \times 10^9$ CFU/g. In some embodiments, the amount of total probiotic in the GI digestive supplement as fed is about $1.15 \times 10^9$ to about $1.10 \times 10^9$ CFU/g. In some embodiments, the amount of total probiotic in the GI digestive supplement as fed is about $1.11 \times 10^9$ CFU/g. In some embodiments, the amount of L-glutamine in the GI digestive supplement as fed is about 500,000 to about 50,000 mg/kg. In some embodiments, the amount of L-glutamine in the GI digestive supplement as fed is about 400,000 to about 100,000 mg/kg. In some embodiments, the amount of L-glutamine in the GI digestive supplement as fed is about 300,000 to about 150,000 mg/kg. In some embodiments, the amount of L-glutamine in the GI digestive supplement as fed is about 250,000 to about 175,000 mg/kg. In some embodiments, the amount of L-glutamine in the GI digestive supplement as fed is about 220,000 to about 180,000 mg/kg. In some embodiments, the amount of L-glutamine in the GI digestive supplement as fed is about 210,000 to about 190,000 mg/kg. In some embodiments, the amount of L-glutamine in the GI digestive supplement as fed is about 200,000 mg/kg.

In some embodiments, the recommended supplement is a joint supplement. In some embodiments, the active ingredients of the joint supplement comprise eggshell membrane, curcumin, or any combination thereof. In some embodiments, the amount of eggshell membrane in the joint supplement as fed is about 200 to about 10 mg/g. In some embodiments, the amount of eggshell membrane in the joint supplement as fed is about 175 to about 25 mg/g. In some embodiments, the amount of eggshell membrane in the joint supplement as fed is about 150 to about 50 mg/g. In some embodiments, the amount of eggshell membrane in the joint supplement as fed is about 125 to about 75 mg/g. In some embodiments, the amount of eggshell membrane in the joint supplement as fed is about 100 to about 80 mg/g. In some embodiments, the amount of eggshell membrane in the joint supplement as fed is about 95 to about 85 mg/g. In some embodiments, the amount of eggshell membrane in the joint supplement as fed is about 90.5 mg/g. In some embodiments, the amount of curcumin in the joint supplement as fed is about 500 to about 10 mg/g. In some embodiments, the amount of curcumin in the joint supplement as fed is about 400 to about 25 mg/g. In some embodiments, the amount of curcumin in the joint supplement as fed is about 300 to about 50 mg/g. In some embodiments, the amount of curcumin in the joint supplement as fed is about 250 to about 75 mg/g. In some embodiments, the amount of curcumin in the joint supplement as fed is about 200 to about 100 mg/g. In some embodiments, the amount of curcumin in the joint supplement as fed is about 175 to about 125 mg/g. In some embodiments, the amount of curcumin in the joint supplement as fed is about 170 to about 140 mg/g. In some embodiments, the amount of curcumin in the joint supplement as fed is about 165 to about 150 mg/g. In some embodiments, the amount of curcumin in the joint supplement as fed is about 160 to about 155 mg/g. In some embodiments, the amount of curcumin in the joint supplement as fed is about 158 mg/g.

In some embodiments, the recommended supplement is a liver supplement. In some embodiments, the active ingredients in the liver supplement comprise curcumin, S-adenosyl-L-methionine, silybin-phosphatidylcholine complex, vitamin E, or any combination thereof. In some embodiments, the amount of curcumin in the liver supplement as fed is about 25,000 to about 1,000 mg/kg. In some embodiments, the amount of curcumin in the liver supplement as fed is about 20,000 to about 2,500 mg/kg. In some embodiments, the amount of curcumin in the liver supplement as fed is about 15,000 to about 5,000 mg/kg. In some embodiments, the amount of curcumin in the liver supplement as fed is about 10,000 to about 7,500 mg/kg. In some embodiments, the amount of curcumin in the liver supplement as fed is about 8,000 mg/kg. In some embodiments, the curcumin is incorporated into the supplement using turmeric root extract. In some embodiments, the amount of S-adenosyl-L-methionine in the liver supplement as fed is about 500,000 to about 25,000 mg/kg. In some embodiments, the amount of S-adenosyl-L-methionine in the liver supplement as fed is about 400,000 to about 50,000 mg/kg. In some embodiments, the amount of S-adenosyl-L-methionine in the liver supplement as fed is about 300,000 to about 75,000 mg/kg. In some embodiments, the amount of S-adenosyl-L-methionine in the liver supplement as fed is about 200,000 to about 80,000 mg/kg. In some embodiments, the amount of S-adenosyl-L-methionine in the liver supplement as fed is about 150,000 to about 90,000 mg/kg. In some embodiments, the amount of S-adenosyl-L-methionine in the liver supplement as fed is about 120,000 to about 100,000 mg/kg. In some embodiments, the amount of S-adenosyl-L-methionine in the liver supplement as fed is about 115,000 to about 105,000 mg/kg. In some embodiments, the amount of S-adenosyl-L-methionine in the liver supplement as fed is about 110,000 mg/kg. In some embodiments, the amount of silybin-phosphatidylcholine complex in the liver supplement as fed is about 100 to about 10 mg/g. In some embodiments, the amount of silybin-phosphatidylcholine complex in the liver supplement as fed is about 90 to about 20 mg/g. In some embodiments, the amount of silybin-phosphatidylcholine complex in the liver supplement as fed is about 70 to about 25 mg/g. In some embodiments, the amount of silybin-phosphatidylcholine complex in the liver supplement as fed is about 60 to about 30 mg/g. In some embodiments, the amount of silybin-phosphatidylcholine complex in the liver supplement as fed is about 50 to about 35 mg/g. In some embodiments, the amount of silybin-phosphatidylcholine complex in the liver supplement as fed is about 45 to about 38 mg/g. In some embodiments, the amount of silybin-phosphatidylcholine complex in the liver supplement as fed is about 40 mg/g. In some embodiments, the silybin-phosphatidylcholine complex will be derived from milk thistle extract. In some embodiments, the milk thistle extract will contain greater than or equal to 80% silymarin. In some embodiments, the amount of vitamin E in the liver supplement as fed is about 10,000 to about 500 IU/kg. In some embodiments, the amount of vitamin E in the liver supplement as fed is about 7,500 to about 1,000 IU/kg. In some embodiments, the amount of vitamin E in the liver supplement as fed is about 5,000 to about 2,000 IU/kg. In some embodiments, the amount of vitamin E in the liver supplement as fed is about 4,000 to about 3,000 IU/kg. In some embodiments, the amount of vitamin E in the liver supplement as fed is about 3,500 to about 3,100 IU/kg. In some embodiments, the amount of vitamin E in the liver supplement as fed is about 3,300 to about 3,200 IU/kg. In some embodiments, the amount of vitamin E in the liver supplement as fed is about 3,280 IU/kg.

In some embodiments, the recommended supplement is a skin and coat supplement. In some embodiments, the active ingredients in the skin and coat supplement comprise eicosapentaenoic acid (EPA) and docosahexaenoic acid (DHA), *Lactobacillus rhamnosus* GG, α-linolenic acid, vitamin E, zinc, biotin, or any combination thereof. In some embodiments, the amount of EPA+DHA in the skin and coat supplement as fed is about 10 to about 100 mg/g. In some embodiments, the amount of EPA+DHA in the skin and coat supplement as fed is about 20 to about 80 mg/g. In some embodiments, the amount of EPA+DHA in the skin and coat supplement as fed is about 30 to about 70 mg/g. In some embodiments, the amount of EPA+DHA in the skin and coat supplement as fed is about 35 to about 60 mg/g. In some embodiments, the amount of EPA+DHA in the skin and coat supplement as fed is about 40 to about 50 mg/g. In some embodiments, the amount of EPA+DHA in the skin and coat supplement as fed is about 41 to about 45 mg/g. In some embodiments, the amount of EPA+DHA in the skin and coat supplement as fed is about 44 mg/g. In some embodiments, *Lactobacillus rhamnosus* GG is a probiotic. In some embodiments, the amount of probiotic in the skin and coat supplement as fed is about 0.10×10$^{10}$ to about 2.00×10$^{10}$ CFU/g. In some embodiments, the amount of probiotic in the skin and coat supplement as fed is about 0.25×10$^{10}$ to about 1.75×10$^{10}$ CFU/g. In some embodiments, the amount of probiotic in the skin and coat supplement as fed is about 0.50×10$^{10}$ to about 1.50×10$^{10}$ CFU/g. In some embodiments, the amount of probiotic in the skin and coat supplement as fed is about 0.75×10$^{10}$ to about 1.25×10$^{10}$ CFU/g. In some embodiments, the amount of probiotic in the skin and coat supplement as fed is about 0.9×10$^{10}$ to about 1.10×10$^{10}$ CFU/g. In some embodiments, the amount of probiotic in the skin and coat supplement as fed is about 0.95×10¹⁰ to about 1.05×10¹⁰ CFU/g. In some embodiments, the amount of probiotic in the skin and coat supplement as fed is about 1.00×10¹⁰ CFU/g. In some embodiments, the amount of α-linolenic acid in the skin and coat supplement as fed is about 10 to about 100 mg/g. In some embodiments, the amount of α-linolenic acid in the skin and coat supplement as fed is about 20 to about 80 mg/g. In some embodiments, the amount of α-linolenic acid in the skin and coat supplement as fed is about 30 to about 70 mg/g. In some embodiments, the amount of α-linolenic acid in the skin and coat supplement as fed is about 35 to about 60 mg/g. In some embodiments, the amount of α-linolenic acid in the skin and coat supplement as fed is about 40 to about 50 mg/g. In some embodiments, the amount of α-linolenic acid in the skin and coat supplement as fed is about 41 to about 45 mg/g. In some embodiments, the amount of α-linolenic acid in the skin and coat supplement as fed is about 43 mg/g. In some embodiments, the amount of vitamin E in the skin and coat supplement as fed is about 100,000 to about 10,000 IU/kg. In some embodiments, the amount of vitamin E in the skin and coat supplement as fed is about 80,000 to about 20,000 IU/kg. In some embodiments, the amount of vitamin E in the skin and coat supplement as fed is about 60,000 to about 40,000 IU/kg. In some embodiments, the amount of vitamin E in the skin and coat supplement as fed is about 58,000 to about 53,000 IU/kg. In some embodiments, the amount of vitamin E in the skin and coat supplement as fed is about 55,000 IU/kg. In some embodiments, the amount of zinc in the skin and coat supplement as fed is about 50,000 to about 1,000 mg/kg. In some embodiments, the amount of zinc in the skin and coat supplement as fed is about 40,000 to about 2,000 mg/kg. In some embodiments, the amount of zinc in the skin and coat supplement as fed is about 30,000 to about 3,000 mg/kg. In some embodiments, the amount of zinc in the skin and coat supplement as fed is about 20,000 to about 4,000 mg/kg. In some embodiments, the amount of zinc in the skin and coat supplement as fed is about 15,000 to about 5,000 mg/kg. In some embodiments, the amount of zinc in the skin and coat supplement as fed is about 12,500 to about 7,500 mg/kg. In some embodiments, the amount of zinc in the skin and coat supplement as fed is about 12,000 to about 10,000 mg/kg. In some embodiments, the amount of zinc in the skin and coat supplement as fed is about 11,000 mg/kg. In some embodiments, the amount of biotin in the skin and coat supplement as fed is about 1 to about 50 mg/kg. In some embodiments, the amount of biotin in the skin and coat supplement as fed is about 3 to about 40 mg/kg. In some embodiments, the amount of biotin in the skin and coat supplement as fed is about 5 to about 30 mg/kg. In some embodiments, the amount of biotin in the skin and coat supplement as fed is about 7 to about 20 mg/kg. In some embodiments, the amount of biotin in the skin and coat supplement as fed is about 9 to about 18 mg/kg. In some embodiments, the amount of biotin in the skin and coat supplement as fed is about 10 to about 16 mg/kg. In some embodiments, the amount of biotin in the skin and coat supplement as fed is about 14 mg/kg.

In some embodiments, the recommended supplement is a weight gain and palatability supplement. Table 7 comprises a non-limiting example of potential components of the weight gain and palatability supplement. In some embodiments, the amounts of one or more components may be higher. In some embodiments, the amounts of one or more components may be lower. In some embodiments, the amounts of one or more components may be about the amounts listed.

TABLE 7

| | Units of Measure | Amount as fed |
|---|---|---|
| Moisture | % | 4.15 |
| Dry Matter | % | 95.85 |
| Crude Protein | % | 41.41 |
| Crude Fiber | % | 0.08 |
| Crude Fat | % | 16.75 |
| Ash | % | 7.22 |
| Calcium | % | 1.35 |
| Phosphorus | % | 1.04 |
| Magnesium | % | 0.07 |
| Potassium | % | 0.59 |
| Sodium | % | 0.77 |
| Zinc | mg/kg | 184.18 |
| Iron | mg/kg | 227.72 |
| Copper | mg/kg | 16.85 |
| Manganese | mg/kg | 31.22 |
| Chloride | % | 1.09 |
| Selenium | mg/kg | 0.32 |
| Added Selenium | mg/kg | 0.32 |
| Iodine | mg/kg | 1.68 |
| Vitamin A | kIU/kg | 22.34 |
| Riboflavin | mg/kg | 9.97 |
| Vitamin D | kIU/kg | 1.41 |
| Vitamin E | kIU/kg | 0.10 |
| Thiamin | mg/kg | 9.92 |
| Niacin | mg/kg | 42.72 |
| Pantothenic | mg/kg | 23.12 |
| Pyridoxine | mg/kg | 3.58 |
| Folic Acid | mg/kg | 0.70 |
| Vitamin B12 | mg/kg | 0.06 |
| Choline | mg/kg | 1564.32 |
| Linoleic acid | % | 2.99 |
| alpha-Linolenic | % | 0.16 |
| Arachidonic | % | 0.61 |
| EPA + DHA | % | 0.06 |
| (Linoleic + Arachidonic):(aLA + EPA + DHA) | N/A | 16.51 |
| Arginine | % | 2.64 |
| Histidine | % | 0.99 |
| Isoleucine | % | 1.78 |
| Leucine | % | 3.14 |
| Lysine | % | 3.10 |
| Methionine | % | 0.74 |
| Methionine-cystine | % | 1.12 |
| Phenylalanine | % | 1.61 |
| Phenylalanine-tyrosine | % | 2.98 |
| Threonine | % | 1.20 |
| Tryptophan | % | 0.54 |
| Valine | % | 2.07 |
| Taurine* | % | 0.00 |
| Carnitine* | mg/kg | 727.50 |
| Vitamin K* | mg/kg | 0.00 |
| Vitamin C* | mg/kg | 0.00 |
| Vitamin E:PUFA | IU/g | 2.64 |
| Carbohydrates | % | 30.39 |
| Ca:P | — | 1.30 |
| ME | kcal/g | 3.94 |

In some embodiments, a base food is recommended for a subject. In some embodiments, the base food is recommended based on the one or more conditions or risk of one or more conditions for a subject. In some embodiments, the base food is the main nutritional product recommended. In some embodiments, the base food is recommended along with other nutritional products. In some embodiments, the other nutritional products comprise treats, supplements, or any combination thereof. In some embodiments, the base food is formulated to target a condition. In some embodiments, the base food is formulated to target multiple conditions. In some embodiments, the base food is formulated to aid an existing condition. In some embodiments, the base food is formulated to aid multiple existing conditions. In some embodiments, the base food is formulated to aid in the prevention of a condition. In some embodiments, the base food is formulated to aid in the prevention of multiple conditions. In some embodiments, the base food has higher amounts of a component present in standard food. In some embodiments, the base food has higher amounts of multiple components present in standard food. In some embodiments, the base food has lower amounts of a component present in standard food. In some embodiments, the base food has lower amounts of multiple components present in standard food. In some embodiments, the base food has lower amounts of one or more components present in standard food and higher amounts of one or more components present in standard food. In some embodiments, the base food has an additional component not found in standard food. In some embodiments, the base food has multiple additional components not found in standard food. In some embodiments, the base food has lower amounts of one or more components present in standard food and one or more additional components not found in standard food. In some embodiments, the base food has higher amounts of one or more components present in standard food and one or more additional components not found in standard food. In some embodiments, the base food has lower amounts of one or more components present in standard food, higher amounts of one or more components present in standard food, and one or more additional components not found in standard food. In some embodiments, the base food is a kibble. In some embodiments, the base food is a wet food. In some embodiments, the wet food is a canned food. In some embodiments, the wet food is a fresh food. In some embodiments, the base food is stored at room temperature. In some embodiments, the base food is stored below room temperature. In some embodiments, the base food is refrigerated. In some embodiments, the base food is frozen. Non-limiting examples of components reduced, decreased, removed, or added or any combination thereof include protein including types of protein, fat including types of fat, carbohydrates including types of carbohydrates, minerals, vitamins, amino acids, electrolytes, micronutrients, and macronutrients.

In some embodiments, the WPS for the subject will guide the recommendation for nutritional product of a subject. In some embodiments, the nutrient profile of the food recommendation may contain increases or decrease to the standard recommended amounts of macronutrients and micronutrients. In some embodiments, the nutrient profile of the food recommendation may contain additional micronutrients not in the standard diet of the subject. In some embodiments, the food recommendation for the subject is selected from Table 8, which contains unique additives and amounts relative to existing food brands.

TABLE 8

| Product Name | Protein (%) | Crude Fat (%) | Unique Additives or Amounts |
|---|---|---|---|
| Cardiac Support | 30 | 15 | Taurine (0.20%) |
|  |  |  | L-Carnitine (200 mg/kg) |
|  |  |  | Sodium (max 0.25%) |
| Digestive Support, Low Fat | 25 | 5.5-9* | EPA + DHA (0.40-1.10%) |
|  |  |  | Vitamin E (400 IU/kg) |
|  |  |  | Total Dietary Fiber (17.5-25.0 g/Mcal) |
|  |  |  | Probiotic (>1 × 10^9 CFU/day) |
| Hydrolyzed Protein | 23 | 10.5 | Linoleic Acid (2.3%) |
|  |  |  | Vitamin E (700 IU/kg) |
| Novel Protein, Low Fat | 21.6 | 9 (max)* | Vitamin E (400 IU/kg) |
|  |  |  | Omega-3 Fatty Acid (0.35-1.80%) |
|  |  |  | EPA + DHA (0.40-1.10%) |
|  |  |  | Total Dietary Fiber (17.5-25.0 g/Mcal) |
| Recovery | 30 | 25 | EPA + DHA (1%) |
|  |  |  | Vitamin E (600 IU/kg) |
| Dental Care | 28 | 16 | N/A |
| Hepatic Support | 24 | N/A | EPA + DHA (0.10%) |
|  |  |  | Vitamin E (400 IU/kg) |
|  |  |  | Copper (1 mg/Mcal)* |
|  |  |  | Sodium (max 0.30%) |
| Urinary Support | 22 | N/A | Sodium (1.25%) |
|  |  |  | Magnesium (max 0.1%) |
| Kidney Support | 18 | 5.5-9* | Phosphorus (max 0.40%) |
|  |  |  | Sodium (max 0.30%) |
|  |  |  | EPA + DHA (0.40%) |
|  |  |  | Vitamin E (400 IU/kg) |
|  |  |  | Vitamin C (100 mg/kg) |
| Weight Loss and Joint Support | 30 | 12 | EPA + DHA (1%) |
|  |  |  | kcal/kg <3250 |

All values are based off dry matter except for items presented with an asterisk (*)

In some embodiments, the nutrition recommendations are based on the one or more conditions or risk of the one or more conditions for the subject. In some embodiments, the nutrition recommendations are based on the wellness probability score (WPS). In some embodiments, nutrition recommendation will mix and match food, supplement, and treat recommendations based on the one or more conditions of the subject. Non-limiting examples of the nutrition recommendation mixing and matching include selecting a recovery food product, a taurine supplement, and a hip and joint treat for a subject that has high activity, a taurine deficiency, and is at risk for hip dysplasia. The same combination of nutrition products could be recommended for a subject that has a lack of appetite, a cardiac problem, and joint damage. The reverse is also true whereby a subject with the same one or more conditions can be given a different recommendation of nutritional products.

Behavioral Modifications and Therapeutic Strategies

Disclosed herein are methods to creating a recommendation for an activity, a usage of a product, or a therapeutic or prophylactic intervention. In some embodiments, the activity may include increasing an existing activity, decreasing an existing activity, stopping an existing activity, or starting a new activity. In some embodiments, the activity is walking. In some embodiments, the activity is running. In some embodiments, the activity is swimming. In some embodiments, the usage of a product is the use of a leash. In some embodiments, the leash is a standard 6-foot leash. In some embodiments, the leash is retractable. In some embodiments, the leash is a hands-free leash. In some embodiments, the leash is a bungee leash. In some embodiments, the usage of a product is a toy. In some embodiments, the toy is a plush toy. In some embodiments, the toy is a chew toy. In some embodiments, the toy is a puzzle toy. In some embodiments, the therapeutic or prophylactic intervention is a series of stretches. In some embodiments, the therapeutic or prophylactic intervention is a dental cleaning. In some embodiments, the therapeutic or prophylactic intervention is a prescription. In some embodiments, the prescription is for flea prevention. In some embodiments, the prescription is for tick prevention. In some embodiments, the prescription is an anti-anxiety drug.

In some embodiments, the subject is a healthy, active canine. Non-limiting examples of recommendations for the healthy, active canine are products that would maintain the health of the canine. In some embodiments, the healthy, active canine expends additional energy requiring higher caloric intake. In some embodiments, the healthy, active canine requires a joint supplement to keep joints healthy. In some embodiments, the healthy, active canine needs prophylactic intervention, such as for example, a dental cleaning, a flea prevention, or a tick prevention. In some embodiments, the subject is a healthy, active dachshund. In some embodiments, the recommendations for the healthy, active dachshund comprises performing various exercises and stretches to aid in potential lameness as the healthy, active dachshund ages. In some embodiments, the subject is a healthy, active feline. Non-limiting examples of recommendations for the healthy, active feline are products that would maintain the health of the feline. In some embodiments, phenotypic data regarding caloric intake and calories burned require the healthy, active feline to reduce caloric intake. In some embodiments, the healthy, active feline has a diet high in fish and requires a vitamin k supplement. In some embodiments, the healthy, active feline needs prophylactic intervention, such as for example, a dental cleaning, a flea prevention, or a tick prevention. Non-limiting examples of the one or more conditions or risk of more or more conditions detected in the subject is taurine deficiency, obesity, lameness, high activity, hip dysplasia, and insect sting allergy.

In some embodiments, the recommendation may include matching nutrition with lifestyle components. In some embodiments, a lifestyle component may be a toy. In some embodiments, a lifestyle component may be a bed. In some embodiments, the recommendation may be made to an insurance company. In some embodiments, the insurance company can provide pet insurance. In some embodiments, the pet insurance may cost significantly less than other plans. In some embodiments, the recommendation may be to the user for a dog walker. In some embodiments, the recommendation may be to the user for a trainer. In some embodiments, the recommendation may be to the user for a groomer. In some embodiments, the recommendation may provide a tele-health visit. In some embodiments, the recommendation may be to a breeder. In some embodiments, the recommendation to the breeder may reduce risks with heritable conditions. In some embodiments, the recommendation to the breeder may reduce risks with temperamental conditions. In some embodiments, the recommendation may be to a shelter. In some embodiments, the recommendation to the shelter may provide information on a shelter animal's behavior. In some embodiments, the information on the shelter animal's behavior is passed onto interested adopters.

Aspects disclosed herein are methods to providing a notification. In some embodiments, the recommendation is provided to the subject. In the case of the non-human subject, in some embodiments, the recommendation is provided to a guardian, medical care provider (e.g., veterinarian), or both of the non-human subject. In some embodiments, the notification is delivered via an App. In some embodiments, the notification is delivered via email. In some embodiments, the notification is viewed via a secure website. In some embodiments, the notification comprises a recommendation. In some embodiments, the notification comprises multiple recommendations. In some embodiments, the notification comprises information on the genotype data of the subject. In some embodiments, the notification comprises information on the phenotype data of the subject. In some embodiments, the notification comprises information about the one or more conditions of the subject. In some embodiments, the notification comprises information on the risk of one or more conditions in the subject. In some embodiments, the notification comprises a WPS. In some embodiments, the notification comprises multiple WPSs. In some embodiments, the notification comprises a multitude of notifications. In some embodiments, the notification is a reminder. In some embodiments, the reminder is for a check-up of the subject. In some embodiments, the reminder is to place an order for a product for the subject. In some embodiments, the reminder is to update information on the subject.

Systems

Disclosed herein, in some embodiments, personalized wellness systems for subjects. In some embodiments, the personalized wellness systems are for animal subject, such as non-human subjects. In some embodiments, the systems are computer systems comprising one or more processors configured to receive a profile for the subject and/or data for the subject (e.g., environmental data, activity data, consumption data, behavioral data, etc.). In some embodiments, the one or more processors disclosed herein is configured to analyze profile and/or data of the subject with a machine learning model, which can produce a wellness probability score (WPS) for the subject. Such WPS may be indicative of whether the subject has, or has a high likelihood of developing, one or more conditions disclosed herein. In some embodiments, the computer system comprises a software module able to generate one or more recommendations related to the WPS, such as a recommendation of a nutritional product, a behavior modification, or a therapeutic intervention. The systems disclosed herein may comprise a personal electronic device of a user (e.g., a guardian of a non-human subject, medical health care provider of the non-human subject) that is communicatively coupled to the computer system. Such personal electronic device may comprise an application (App) configured to display on a graphical user interface (GUI) the WPS, the one or more recommendations, or a combination thereof. Non-limiting examples of the GUI of the App disclosed herein and elsewhere described are provided in FIG. 4 and FIGS. 5A-5D. In some embodiments, the systems comprise a non-computing device, such as a genotyping device (e.g., sequencer, qPCR machine, etc.) used to obtain genotype or biomarker data for the subject. In some embodiments, the systems comprise the kits provided herein, such as kits for collecting a sample from the subject, and/or processing the samples to obtain the genotype or biomarker data.

In some embodiments, the one or more recommendations for a nutritional product, comprises a custom or semi-custom nutritional system including, for example, one or more foods, supplements, or treats for the subject. As described herein, recommendations (as described below with respect to FIGS. 1-6, 12) may include one or more custom nutrition systems for an animal based, at least in part, on the WPS of the subject for the one or more conditions disclosed herein. In some embodiments, custom or semi-custom nutrition systems may be recommended to ameliorate or prevent the one or more conditions that an animal has, or is at a high risk of developing (as described below with respect to FIG. 1). Non-limiting examples of additives and enhancements to the food products disclosed herein are provided in Table 8.

Nutritional Products

Disclosed herein, in some embodiments, are systems comprising one or more nutritional products. In some embodiments, nutritional products may include one or more types of food, meals, treats, supplements, water or a combination thereof. In some embodiments, the nutritional product contain one or more ingredients as elsewhere herein. In some embodiments, the one or more ingredients is derived from a guideline for foods that are recommended to be consumed by an animal (e.g., in a meal, treat, and/or supplement). In some embodiments, the one or more ingredients is selected to ameliorate or prevent one or more conditions disclosed herein in the animal, such as a condition identified by the personalized wellness systems herein. In some embodiments, the one or more formula guidelines include crude protein requirements, crude fat requirements, crude fiber requirements, moisture requirements, taurine requirements, L-Carnitine requirements, and/or sodium requirements. In some embodiments, the one or more formula guidelines may include a country of manufacture (e.g., the United States of America), one or more required ingredients, whether one or more ingredients should be fresh or dehydrated, one or more ingredients that should not or cannot be included in the food, whether the food is efficacious in treating dental plaque and/or tartar previous, one or more recommended food sizes, a minimum and/or maximum Eicosapentaenoic Acid (EPA) and Docosahexaenoic Acid (DHA), a minimum and/or maximum level of fiber, whether a probiotic is required, a minimum and/or maximum level of copper, a linoleic acid level, whether the custom nutrition system includes hydrolyzed protein, and/or one or more recommended fatty acid contents.

In some embodiments, the nutritional products comprise one or more ingredients recommended for the subject by the personalized wellness system disclosed herein. In some embodiments, the one or more ingredients to be included may include chicken (dried or veterinary-prescribed (MD)), white rice or brown rice, cracked barley or pearled barley, chicken liver, chicken fat with mixed tocopherols, sweet potato powder, egg, digest, trout, salmon oil, magnesium proteinate, DL-methionine, threonine, one or more vitamins (e.g., vitamin E, vitamin D, vitamin C, vitamin B, vitamin A, or other vitamins), L-Lysine, salt, chelated minerals, taurine, choline chloride, natural antioxidants (e.g., Naturox®) in liquid or dry formulations, potassium chloride, inulin, dandelion greens, L-Carnitine, pork (dried or MD), pork fat, calcium carbonate, NSA Dog vitamins, blueberries (dried or fresh), pumpkin (dried or fresh), apples (dried or fresh), oat groats, sunflower oil, peas, flaxseed, kelp, lentils, zinc, hydrolyzed chicken, chicken fat, calcium carbonate, potassium chloride, flaxseed oil, psyllium husk, miscanthus grass, cod, brewer's rice, L-threonine, ascorbic acid, L-tryptophan, potassium citrate, and/or cranberries or cranberry extract.

In some embodiments, the nutritional products disclosed herein are custom or semi-custom for the subject, based on the WPS and/or recommendation for the subject. In some embodiments, the nutritional product may improve the health of an animal by alleviating one or more symptoms of one or more conditions. In some embodiments, the one or more diseases include one more cardiac diseases, class I cardiovascular diseases, Mitral valve disease, chronic valvular disease, dental conditions, gastrointestinal conditions (e.g., acute gastroenteritis), pancreatitis, lymphangiectasia, hyperlipidemia, hepatic conditions, liver disease, copper storage disease, acute or chronic kidney disease, urinary conditions (e.g., a urinary tract infection), struvite urolithiasis, calcium oxalate urolithiasis, or obesity. In some embodiments, the custom nutrition systems may improve the dental condition of an animal. In some embodiments, the custom nutrition systems may improve the cardiovascular condition of an animal. In some embodiments, the custom nutrition systems may improve the hepatic condition of an animal. In some embodiments, the custom nutrition systems may support weight loss of the animal. The one or more details may be utilized in generating or updating wellness information for an animal, as described further below with respect to FIGS. 1-3.

In some embodiments, a system comprises a personalized electronic device (e.g., computing device 120 of FIG. 1) communicatively coupled to the computer system. In some embodiments, the personal electronic device belongs to a user of the system. Users of the system disclosed herein may be the subject, a medical health care provider (e.g., nurse, nurse practitioner, physician, pharmacist, medical laboratory, etc.). In the case of a non-human animal subject, the user may be the guardian, a veterinarian, a groomer, or daycare or boarding facility personnel of the subject.

Computer Systems

Disclosed herein, in some embodiments, are computer systems configured to receive data for the subject and generate a wellness probability score (WPS) for the subject by analyzing the data. In some embodiments, the subject is an animal. In some embodiments, the animal is a non-human animal, such as a companion animal or farm animal. In some embodiments, the computer system comprises one or more processors configured to execute instructions for performing the methods disclosed herein. In some embodiments, the one or more processors is configured to analyze a profile for the subject, such as a genotype-phenotype profile, and/or additional data (e.g., activity data, consumption data, behavioral data, environmental data). The computer systems disclosed herein have one or more software modules for receiving activity data, consumption data, and/or user input and generating or updating a WPS and/or a recommendation for the wellness of a subject.

FIG. 1 depicts a non-limiting example of a computer system 100 for providing a WPS with one or more recommendations for a subject (e.g., an animal). In this depicted example, system 100 includes server 110, computing device 120, first device 130, and second device 140. In some embodiments, system 100 includes only one of first device 130 and second device 140. In some embodiments, the system 100 does not include the first device 130 or second device 140. In embodiments that do not include the first device 130 or second device 140, the computing profile 120 does not provide profile information to first device 130 or second device 140. In embodiments that do not include the first device 130 or second device 140, the computing profile 120 does not receive sensory information from first device 130 or second device 140. In some embodiments, the first device 130 or the second device 140 comprise a non-computer component. In some embodiments, the first device 130 or the second device 140 comprises a genotyping device (e.g., qPCR machine, next-generation sequencer). In some embodiments, the first device 130 or the second device 140 comprises a wearable activity tracking device, such as a GPS-enabled collar, tag, or chip.

In this depicted embodiment, server 110 further includes machine learning component 112 and database 114. In this depicted embodiment, server 110 is configured to communicate (e.g., send or receive information) with computing device 120. In this depicted embodiment, server 110 may send or receive profile information regarding an animal to or from, respectively, computing device 120. In some embodiments, server 110 may only receive profile information from computing device 120 rather than send the profile information. In some embodiments, server 110 may only send profile information to computing device 120 rather than receive profile information. In this depicted embodiment, server 110 is further configured to receive sensor information 154 from computing device 120. In some embodiments, server 110 may be configured to receive sensor information from one or more devices (e.g., sensor information 134 from first device 130 or sensor information 144 from second device 140).

In this depicted embodiment, computing device 120 further comprises UI component 122. In this depicted embodiment, computing device 120 is configured to communicate (e.g., send or receive information) with server 110. In this depicted embodiment, computing device 120 may send or receive profile information regarding an animal to or from, respectively, server 110. In some embodiments, computing device 120 may only send profile information to server 110 rather than receive profile information. In this depicted embodiment, computing device 120 is further configured to communicate with first device 130 and second device 140. In some embodiments, computing device 120 may only be in communication with one of first device 130 or second device 140. In some embodiments, computing device 120 may be in communication with additional devices other than first device 130 and second device 140. In some embodiments, computing device 120 may not be in communication with first device 130 or second device 140. In this depicted embodiment, computing device may send profile information regarding an animal to first device 130 and may further receive sensor information 134 from first device 130. In this depicted embodiment, computing device 120 is further configured to receive sensor information 144 from second device 140. In this depicted embodiment, computing device 120 is further configured to send sensor information 154 from computing device 120. In some embodiments, sensor information may include all or part of sensor information 134 and sensor information 144. In some embodiments, the computing device 120 may be associated with a user. In some embodiments, the user may be a guardian of the animal or a veterinarian that cared, is caring for, or will care for the animal.

In this depicted embodiment, first device 130 further comprises first sensor 132. First sensor 132 may sense sensor information 134 regarding one or more activities associated with an animal. In some embodiments, the animal may be non-human. In some embodiments, the animal may be a mammal, reptile, amphibian, or avian. In some embodiments, the animal may be a dog, cat, horse, chicken, pig, or rat. In some embodiments, the sensor information 134 may include activities data of the animal. In some embodiments, the activity data may include urination data of the animal, excretion data of the animal, abnormal behavior data of the animal, symptom data of the animal, exercise data of the animal; activity level data of the animal; activity type data of the animal; sleep data of the animal; calories burned by the animal; and/or data associated with the animal refusing to eat. In some embodiments, the animal urination data includes at least one instance of the animal urinating or a urination pattern of the animal. In some embodiments, the excretion data of the animal includes at least one instance of the animal excreting fecal matter or vomiting or an excretion or vomiting pattern of the animal. In some embodiments, the exercise data of the animal may include one or more types of exercise (e.g., walking, running, playing, swimming, galloping, climbing, flying), one or more times or durations at which the animal was exercise, and/or a location of the exercise. In some embodiments, the activity level data of the animal may include an activity score indicating the intensity of the activity. In some embodiments, the activity type data includes one or more types of activity (e.g., eating, drinking, urinating, exercising, sleeping). In some embodiments, the sleep data of the animal may include one or more occurrences during sleep (e.g., waking up, needing to urinate), an amount of time slept, a location of where the animal slept, and/or a quality of the sleep. In some embodiments, data associated with the animal refusing to eat may include an instance of the animal refusing to eat, a pattern of the animal refusing to eat, and/or a food that the animal refuses to eat. In some embodiments, the first device 130 may include a collar, a bracelet, an implant, a facial accessory, or a shoe. While some examples of the first device may be listed above, these are exemplary and other devices may be used. In some embodiments, the first device 130 is configured to be worn by the animal. In some embodiments, the first device 130 senses sensor data 134 while being worn by the animal. In this depicted embodiment, first device 130 is configured to provide sensor information 134 to computing device 120. In this depicted embodiment, first device 130 is configured to receive profile information of the animal from computing device 120. In some embodiments, first device 130 may use the received profile information from computing device 120 to partially determine activity data of the animal. For example, the computing device 120 may provide a weight of the animal, and the first device 130 may use the weight of the animal to determine the calories burned by the animal during exercise.

In this depicted embodiment, second device 140 further comprises second sensor 142. Second sensor 142 may sense sensor information 144 regarding a genotype of the animal. In some embodiments, the second device 140 may be a genotyping device. In some embodiments, genotype data may be transmitted from the genotype device directly or indirectly to one or more processors disclosed herein. In some embodiments, the genotyping device is a qPCR machine. In some embodiments, the genotyping device is a next-generation sequencer.

In these depicted embodiments, the UI component 122 of computing device 120 may include one or more user interfaces. The one or more user interfaces may be configured to receive user input. In some embodiments, the user input may include profile information, additional activity data, additional consumption data, and/or goal information for the animal. In some embodiments, the user input may include an amount of food eaten by the animal, one or more types of food eaten by the animal, nutritional information of food eaten by the animal, an amount of exercise of the animal, a recommended amount of food or type of food for the animal, a disease, condition, or disorder of the animal, an age of the animal, a sex of the animal, data indicating whether the animal is neutered or spayed, a weight of the animal, a goal weight of the animal, sleep data of the animal, location data of the animal, environmental data related to a location of the animal, one or more medications or treatments for the animal, adverse reaction data to one or more medications or treatments for the animal, one or more past or current conditions of the animal, one or more symptoms exhibited by the animal, behavioral data of the animal, an aspect of urination of the animal, a urination pattern of the animal, an aspect of fecal matter of the animal, an excrement pattern of the animal, additional genotypic data, or additional phenotypic data. In some embodiments, the one or more types of food eaten by the animal include meals, treats, or supplements. In some embodiments, the one or more types of food further include a type of meal (e.g., breakfast, lunch, or dinner), a brand of meal (e.g., from one or more recommended diets, as described further below), one or more types of treats (e.g., a dental treat), a brand of treat (e.g., one or more recommended treats, as described further below), one or more types of supplements (e.g., a vitamin), and/or a brand of supplement (e.g., one or more recommended supplements, as described further below). In some embodiments, the one or more conditions may include a disease, a skin condition, a coat condition, or an infection. In some embodiments, the disease includes one or more of cancer, heart disease, arthritis a gastrointestinal condition, parvovirus, or distemper. In some embodiments, the infection includes one or more of an internal parasite, an external parasite, an ear infection, or a urinary tract infection. In some embodiments, the one or more conditions include one or more of distemper, glanders, tetanus, or botulism. In some embodiments, the one or more conditions include chronic kidney disease, anemia, diabetes, hyperthyroidism, or urinary tract disease. In some embodiments, the one or more conditions include respiratory disease, mastitis, parvovirus, or swine fever. In some embodiments, the computing device 120 may augment sensor information 134 or sensor information 144 based on the user input. For example, computing device 120 may use user input indicating the weight of the animal to adjust sensor information 134 to reflect more accurately a number of calories burned. In some embodiments, computing device 120 may not augment sensor information 134 or sensor information 144. In some embodiments, the user input is included in sensor information 154 to be sent to the server 110.

Machine learning component 112 may be configured to generate one or more recommendations associated with an animal based on received sensor information 154. Machine learning component 112 may include one or more machine learning models. The one or more machine learning models may include a decision tree machine learning model, a random forest machine learning model or a gradient boosted machine learning model. In some embodiments, the machine learning model comprises an unsupervised machine learning model. In some embodiments, the unsupervised machine learning model comprises a clustering algorithm, such as a K-means clustering, centroid-based clustering algorithm, density-based clustering algorithm, distribution-based clustering algorithm, or a hierarchical clustering algorithm. In some embodiments, the machine learning model may assign one or more labels one or more needs as inclusive or exclusive, where an inclusive need indicates a positive need for the subject (e.g., the animal must perform a task, ingest a nutritional product), and an exclusive need indicates that a negative need (e.g., the animal must refrain from performing a task or refrain from ingesting a nutritional product). In some embodiments, inclusive or exclusive needs may be assigned based on genotypic data, environmental data, phenotypic data, consumption data, or activity data of an animal, or any combination thereof.

Machine learning component 112 may use the received sensor information 154 and a profile associated with the animal in order to generate a recommendation regarding the health of the animal. In some embodiments, database 114 may include a profile for the animal. In some embodiments, the database 114 may include a plurality of profiles for a plurality of animals, where the plurality of profiles includes the profile for the animal.

In generating the recommendation, machine learning component 112 may use received sensor information 154 and the profile associated with the animal in identifying whether the animal has one or more conditions or is at risk of developing the one or more conditions. As described above, the one or more conditions may include a disease, a skin condition, a coat condition, or an infection. In some embodiments, at least one machine learning model of the one or more machine learning models of machine learning component 112 may receive the sensor information 154 and the profile associated with the animal as input and may output one or more scores indicating whether the animal has or is at risk of developing the one or more conditions.

In some embodiments, the machine learning model may assign a score to a particular condition for an animal indicating a likelihood of the animal having the condition of developing the condition. In some embodiments, the machine learning model will update a score for the particular condition if the score for the particular condition already exists or has been assigned. In some embodiments, the score comprises a wellness probability score (WPS). In some embodiments, the WPS may be 0, 1, or 2. In some embodiments, a WPS of 0 indicates that the animal has the condition or is highly likely to develop the condition with a positive predictive value above 50%, a WPS of 1 indicates that the animal has the condition or is highly likely to develop the condition with a positive predictive value of 50%; and a WPS of 2 indicates that the animal has the condition or is highly likely to develop the condition with a positive predictive value below 50%.

For example, the at least one machine learning model may receive a profile for a dog as input and may also receive sensor information 154, where the profile indicates that the dog previously weighed 120 pounds and sensor information 154 indicates that the dog now weighs 130 pounds (e.g., user input), walks for 15 minutes a day (e.g., activity data included in sensor information 134), and eats 4 pounds worth of meals a day (e.g., consumption data included in sensor information 144). In that particular example, based on the profile and the sensor information 154, the at least one machine learning model may identify the dog as having obesity or being at risk of developing obesity by assigning a WPS of 2 to the condition of obesity.

In this depicted embodiment, the machine learning component 112 further generates a recommendation 160 based on the profile and the sensor information 154. In some embodiments, the recommendation 160 may include the WPS for one or more conditions. In some embodiments, the recommendation 160 includes only one or more WPSs for one or more conditions and one or more respective indicators for the one or more conditions. The recommendation 160 may include one or more indicators regarding the health of the animal and or recommended actions regarding the health of the animal. In some embodiments, the one or more indicators may include WPS scores, insights, symbols, and/or colors. For example, a recommendation may include a WPS score of 2 regarding the risk of developing a condition (e.g., obesity) for the animal and an insight indicating that the animal should exercise more and eat less of a particular food. The recommendation may further include a symbol such as a broken heart to indicate that the animal is likely to develop the condition, and a background of the recommendation could be red to indicate that the animal is likely to develop the condition. While some insights, symbols, and colors have been described above, these are exemplary and other insights, symbols, and colors may be used.

In this depicted embodiment, the server 110 provides the recommendation 160 to the computing device 120. In some embodiments, the computing device 120 may display the recommendation 160 on the user interface component 122.

In some embodiments, at least a second machine learning model of machine learning component 112 may update the profile of the animal based on sensor information 154. For example, if the profile indicates that the animal is 90 pounds and not at risk of a condition such as hip dysplasia, and the sensor information 154 indicates that the animal is in fact 110 pounds, the profile may be updated to indicate that the animal is 140 pounds and likely to develop hip dysplasia. The updated profile may then be used to determine recommendations.

In some embodiments, server 110 and computing device 120 may be configured to generate a profile for an animal (as described with respect to FIG. 12). In those embodiments, server 110 and computing device 120 may communicate the profile information as depicted in this example. Based on the profile information, server 110 generates a profile for the animal as described herein and may provide the profile to computing device 120. In those embodiments, UI component 122 may display one or more aspects of the profile. In those embodiments, as described above, the computing system 120 may not communicate with the first device 130 and/or second device 140. In those embodiments, the computing system 120 may not receive sensor information from the first sensor 132 and/or the second sensor 142. In those embodiments, the computing system 120 may not receive sensor information 134 and/or 144. In those embodiments, computing device 120 may not provide sensor information 154 to server 110.

Figure 2:
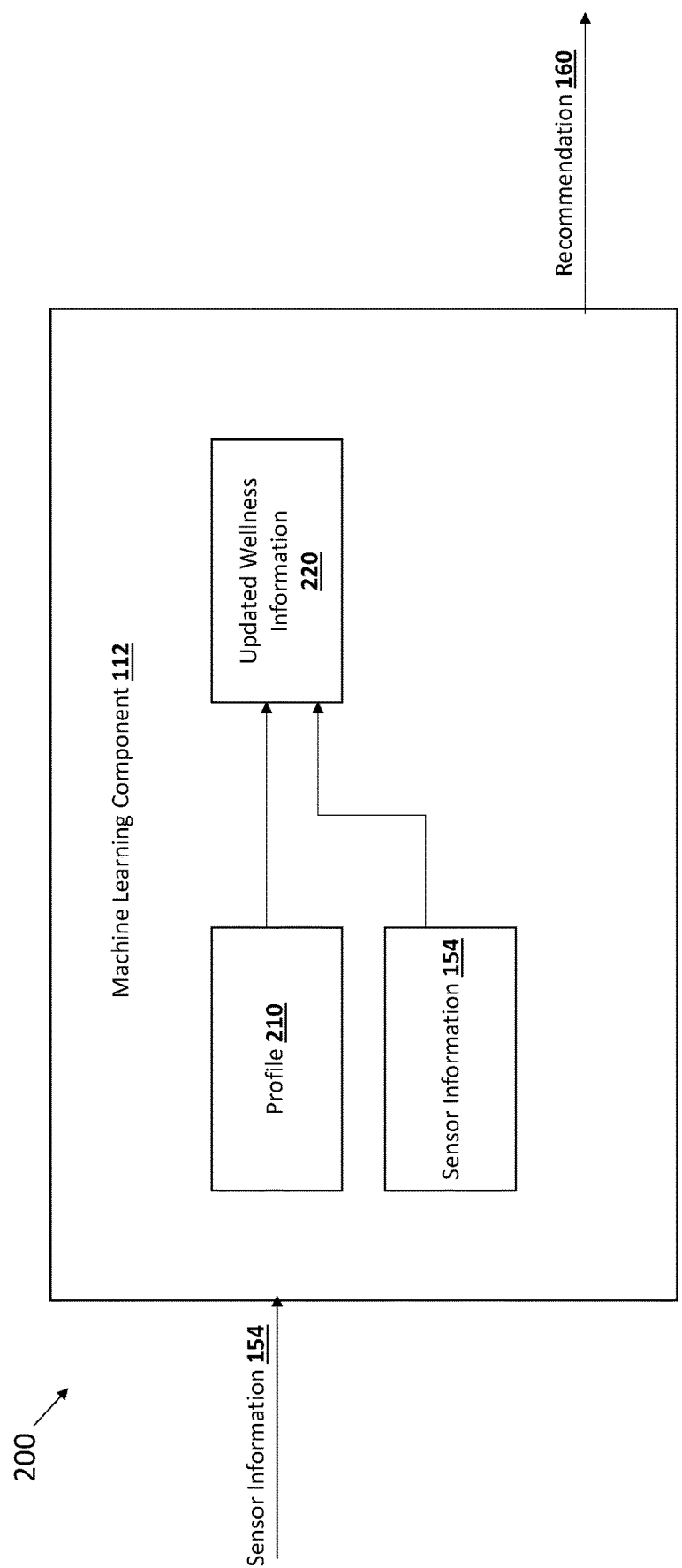
FIG. 2 depicts a non-limiting example of a process for generating a recommendation based on received wellness information of an animal.

FIG. 2 depicts a non-limiting example of a process 200 for generating a recommendation. In some embodiments, the process for generating a recommendation may include a processing device (e.g., server 110 of FIG. 1) receiving a profile for an animal as well as activity data, consumption data, and/or user input for the animal (e.g., from sensor information 154 of FIG. 1). In some embodiments, the animal is non-human. In some embodiments, the animal may be a mammal, reptile, amphibian, or avian. In some embodiments, the animal may be a dog, cat, horse, chicken, pig, or rat.

The process beings with machine learning component 112 receiving sensor information 154, which may contain activity data, consumption data, and/or user input as described above. In some embodiments, a profile 210 is received. In this depicted embodiment, machine learning component 112 has retrieved profile 210 from a database (e.g., database 114 of FIG. 1).

Machine learning component 112, using one or more machine learning models, analyzes profile 210 and sensor information 154 to identify if the animal has one or more conditions or is at risk of developing one or more conditions (e.g., the one or more conditions as described with respect to FIG. 1). In some embodiments, the profile may include one or more attributes relating to the health of the animal. In some embodiments, the one or more attributes may include genetic variants, specific phenotypic traits, and likelihoods of developing one or more conditions described herein. Sensor information 154 may be used in combination with the one or more attributes to identify if the animal has the one or more conditions or is at risk of developing the one or more conditions as well as provide a recommendation regarding the one or more conditions. For example, the profile 210 may include one or more genetic variants of the animal related to specific phenotypic traits that indicate the animal is has or is at risk of developing the one or more conditions, and the sensor information 154 may be used to determine one or more effects on the health information related one or more conditions in relation to the animal (e.g., if the animal has the one or more conditions or is at an increased or decreased risk for developing the one or more conditions). Based on the updated health information that was updated based on the profile 210 and the sensor information 154, the one or more machine learning models can then determine and provide recommendation 160. Recommendation 160 may provide one or more indicators that may include WPS scores, insights, symbols, and/or colors, as described above.

For example, if (1) the profile 210 includes a genetic variant that indicates the animal is at risk for heart disease, and (2) the sensor information 154 indicates that the animal has not exercised during a given time period and also eaten a meals of a food type that increases the risk of heart disease, (3) the one or more machine learning models may update the health information 220 of the animal to indicate that the animal has heart disease or has an increased risk of developing heart disease. As a result, the recommendation 160 may indicate that the animal should exercise for at least 30 minutes during the remainder of the day, should only eat a small meal for the remainder of the day, and that the food type currently eaten by the animal should be changed to a food type that does not increase the risk of heart disease as soon as possible.

Thus, by using the sensor information 154 which tracks the activity and consumption of animal, along with the profile containing the genetic and phenotypic data of the animal, machine learning component 112 can update the health information 220 of the animal and provide a recommendation 160 to improve the health of the animal.

Training a Machine Learning Model

Figure 3:
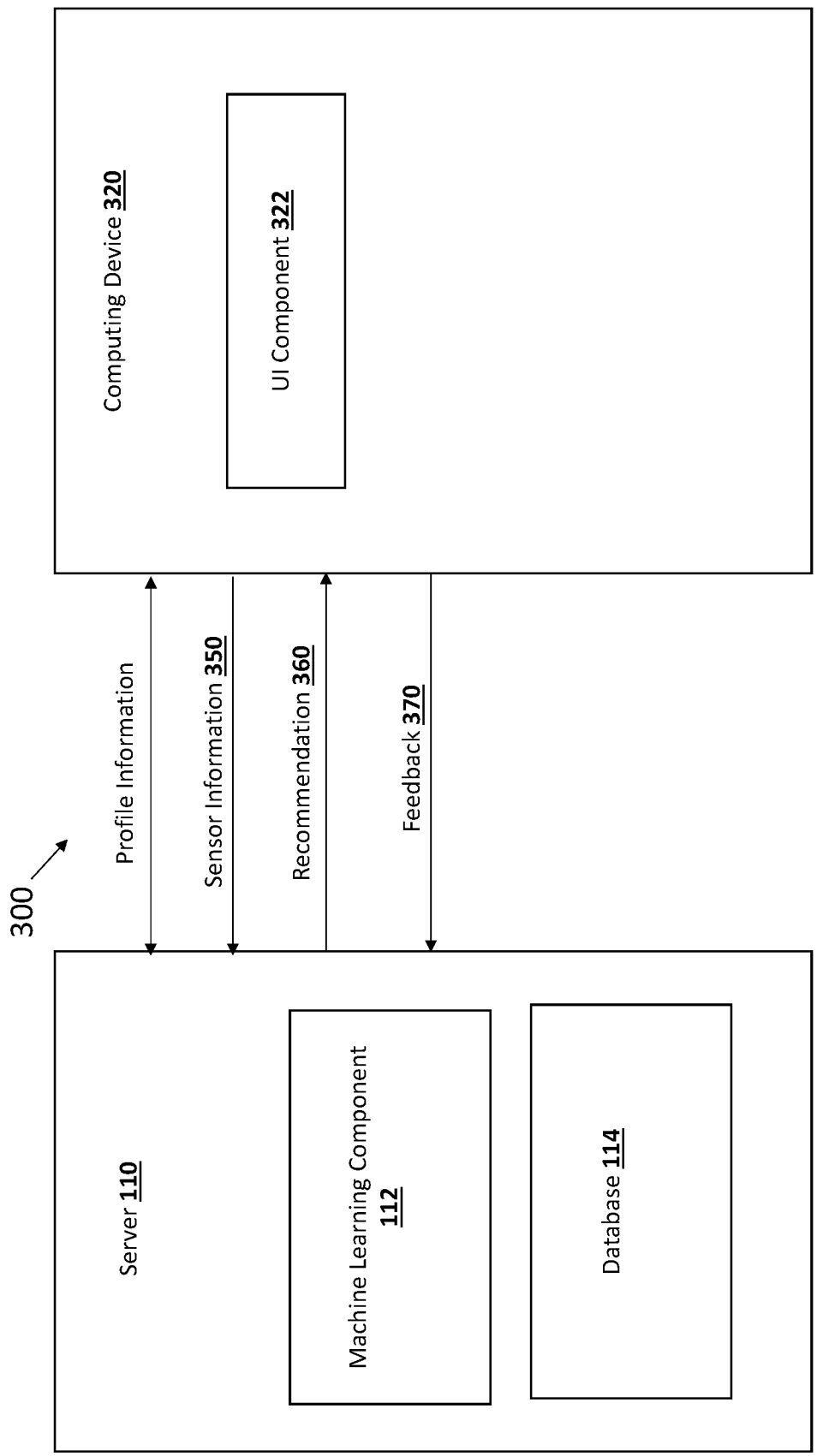
FIG. 3 depicts a non-limiting example of a system for training a machine learning model to identify an animal as having one or more conditions or at a risk of developing the one or more conditions.

Also provided are systems for training a machine learning model disclosed herein. FIG. 3 depicts a non-limiting example of a computer system 300 for training one or more machine learning models to provide a recommendation. In this depicted example, system 300 includes server 110 and computing device 320.

In this depicted example, server 110 further includes machine learning component 112 and database 114. In this depicted embodiment, server 110 is configured to communicate (e.g., send or receive information) with computing device 320. In this depicted embodiment, server 110 may receive training profile information regarding an animal from computing device 320. In some embodiments, the training profile information includes a plurality of training profiles. In this depicted embodiment, server 110 is configured to receive training sensor information 350.

In this depicted example, server 110 further includes machine learning component 112 and database 114. In some embodiments, machine learning component 112 includes one or more machine learning models configured to receive the plurality of training profiles and training sensor information 350 to generate one or more recommendations. In some embodiments, the plurality of training profiles include one or more attributes relating to the health of the animal (as described above with respect to FIG. 2) and the training sensor information includes training activity data, training consumption data, and training user input (as described above with respect to FIGS. 1-2). Based on the plurality of training profiles and the training sensor information, machine learning component 112 may generate one or more recommendations 360 for each training profile.

In this depicted example, server 110 is further configured to provide the one or more recommendations 360 to computing device 320. In this depicted example, computing device 320 includes UI component 322. In some embodiments, UI component 322 may include one or more user interfaces configured to receive user input.

Computing device 320 may further be configured to provide feedback 370 regarding the one or more recommendations 360. In some embodiments, the feedback 370 regarding the one or more recommendations may include revised recommendations including one or more indicators (as described above with respect to FIGS. 1-2). In some embodiments, computing device 320 may receive the feedback 370 as input to the user interface of UI component 322.

Server 110 may further be configured to receive the feedback 370. In some embodiments, the one or more machine learning models of the machine learning component 112 may adjust one or more parameters in response to the feedback 370, thereby training the one or more machine learning models of machine learning component 112.

User Interfaces for Providing User Input and/or Viewing Activity Data and Consumption Data In identifying an animal as having one or more conditions or as being at risk of developing the one or more conditions (e.g., the one or more conditions as described above with respect to FIGS. 1-3), one or more graphical user interfaces may be used (e.g., through UI component 122 of FIG. 1 or UI component 132 of FIG. 3). Graphical user interfaces may be displayed on a processing device (e.g., computing device 120 of FIG. 1 or computing device 320 of FIG. 3). In some embodiments, graphical user interfaces may be used to display one or more aspects of activity data or consumption data. In some embodiments, graphical user interfaces may be used to input user input to the processing device. In some embodiments, the user input may be used to augment or edit the activity data or consumption data. In some embodiments, the graphical user interface may display one or more recommendations and may display one or more aspects associated with identifying an animal as having one or more conditions or as being at risk of developing the one or more conditions (e.g., a WPS).

Figure 4:
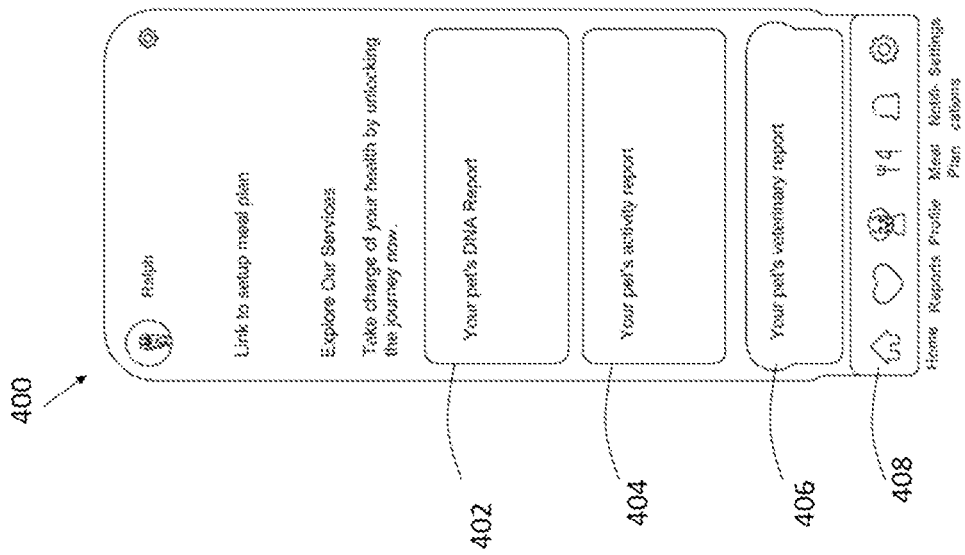
FIG. 4 depicts a non-limiting example graphical user interface (GUI) for an application dashboard, in accordance with some of the embodiments of the present disclosure.

FIG. 4 depicts an example user interface 400 including a plurality of interactive elements for viewing one or more recommendations, one or more profiles, activity data, and consumption data, as well as for inputting user input. In some embodiments, the interactive elements may be accessed through touch input, voice or sound input, electronic input, manual input (e.g., using a mouse to click on an interactive element), or another form of input. While certain inputs are listed above, these inputs are exemplary and other inputs may be used. In some embodiments, additional elements may be included that are not interactive.

In this depicted embodiment, user interface 400 includes interactive elements 402, 404, 406, and 408. Interactive elements 402, 404, and 406 all may receive user input. In some embodiments, in response to the user input, interactive elements 402, 404, and/or 406 may display a different portion of the user interface (as described below with respect to FIGS. 5A-5D).

In this depicted embodiments, interactive element 408 includes a menu with multiple different tabs (e.g., "Home", "Reports", "Profile", "Meal Plan", "Notifications", or "Settings"). In some embodiments, user input may be received associated with one or more of the tabs. In some embodiments, each tab of the one of more tabs may display a different portion of the user interface after user input associated with the tab is received. In some embodiments, one or more tabs of interactive element 408 may display the same portion of the user interface that is displayed when user input is received at one of interactive elements 402, 404, or 406.

In this depicted embodiment, interactive element 402 is associated with a profile of an animal. After receiving user input at interactive element 402, one or more elements of the profile of the animal may be displayed (as described further with respect to FIGS. 5A-5B).

In this depicted embodiment, interactive element 404 is associated with activity data and consumption data of the animal. After receiving user input at interactive element 404, one or more elements associated with the activity data and/or consumption data of the animal may be displayed (as described further with respect to FIGS. 5C-5D).

In this depicted embodiment, interactive element 406 is associated with health information of the animal. After receiving user input at the interactive element 406, one or more elements associated with the health information of the animal may be displayed (as described further with respect to FIG. 5D).

While a certain layout of the user interface 400 is displayed, this is exemplary and other layouts may be used. Additionally, while interactive elements 402, 404, 406, and 408 are included in user interface 400, these elements are also exemplary and other elements may be used. For example, additional or fewer elements may be included. As another example, the interactive elements may display different information than elements associated with the profile of the animal, the activity data of the animal, the consumption data of the animal, or the health information of the animal.

Figure 5B:
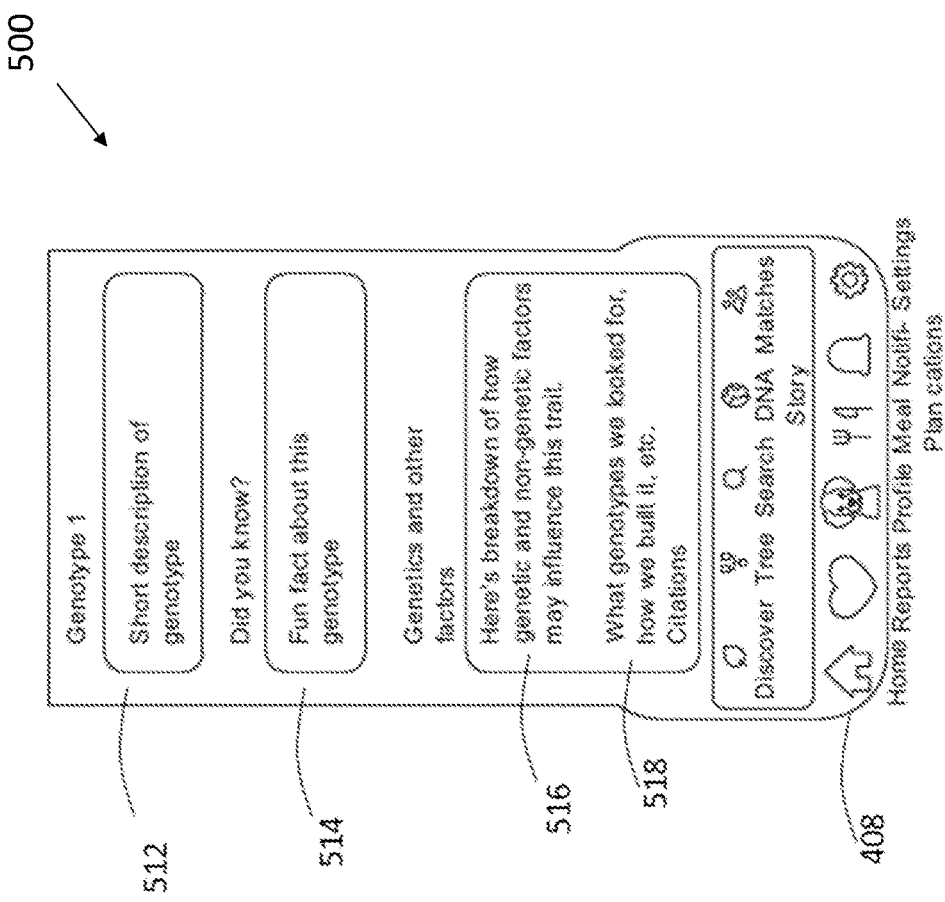
FIGS. 5A-5D depict non-limiting example GUIs where a profile, wellness information, or user input pertaining to wellness information of one or more animals can be managed.
Figure 5A:
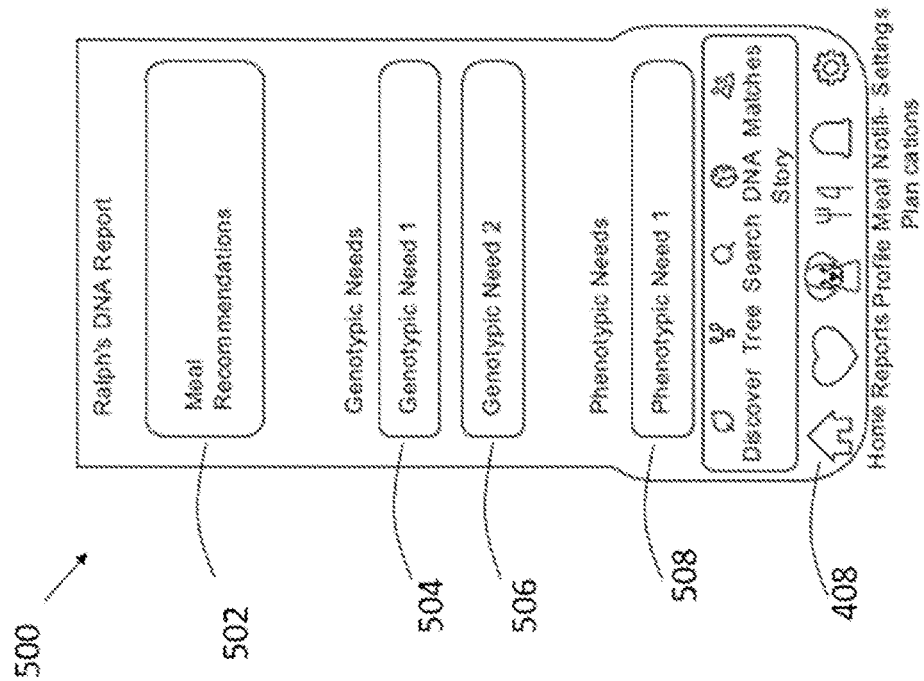

FIG. 5A depicts a non-limiting example of user interface 500 displaying elements 408, 502, 504, 506, and 508. In this depicted embodiment, example user interface 500 includes information regarding the profile of an animal (e.g., a dog named "Ralph"). In this depicted embodiment, user input may be received at any one of interactive elements 408, 502, 504, 506, sand 508. In this depicted embodiment, interactive element 502 is associated with information regarding one or more recommendations (e.g., a recommendation 160 as described with respect to FIGS. 1-2). In some embodiments, upon receiving user input to interactive element 502, the user interface 500 may display one or more indicators of the one or more recommendations (e.g., the indicators as described with respect to FIGS. 1-2). For example, upon receiving user input to interactive element 502, user interface 500 may display one or more custom nutrition systems. In this depicted embodiment, interactive element 504 is associated with information regarding the profile of the animal (e.g., one or more genotypes of the animal.) Further, in some embodiments, interactive element 504 may be associated with one or more recommendations regarding one or more conditions of the animal (e.g., one or more actions that should be performed with regard to a genotypic need of the animal). In some embodiments, upon receiving user input to interactive element 504, the user interface 500 may display one or more indicators of the one or more recommendations. For example, upon receiving user input to interactive element 504, user interface 500 may display one or more facts about the profile of the animal or how an animal may have or may be at risk of developing one or more conditions (as described further with respect to FIG. 5B). Further, in some embodiments, interactive element 506 may be associated with one or more recommendations regarding one or more conditions of the animal (e.g., one or more actions that should be performed with regard to a genotypic need of the animal). In some embodiments, upon receiving user input to interactive element 506, the user interface 500 may display one or more indicators of the one or more recommendations. For example, upon receiving user input to interactive element 506, user interface 500 may display one or more facts about the profile of the animal or how an animal may have or may be at risk of developing one or more conditions. Further, in some embodiments, interactive element 508 may be associated with one or more recommendations regarding one or more conditions of the animal (e.g., one or more actions that should be performed with regard to a phenotypic need of the animal). In some embodiments, upon receiving user input to interactive element 508, the user interface 500 may display one or more indicators of the one or more recommendations. For example, upon receiving user input to interactive element 508, user interface 500 may display one or more facts about the profile of the animal or how an animal may have or may be at risk of developing one or more conditions. While certain interactive elements are described above, these interactive elements are exemplary and other interactive elements may be used. Additionally, while certain elements are described above as interactive, these are exemplary, and other elements that are not interactive may be used.

FIG. 5B depicts a non-limiting example of a user interface 500 displaying elements 408, 512, 514, 516, and 518. In this depicted example, elements 512, 514, 516, and 518 are not interactive. In other embodiments, elements 512, 514, 516, and 518 may be interactive and/or example user interface may display other interactive elements. In this depicted example, elements 512, 514, 516, and 518 are displayed upon the interactive element 504 of FIG. 5A receiving user input. In this depicted embodiment, elements 512, 514, 516, and 518 display information regarding a genotype of an animal associated with interactive element 504 of FIG. 5A. In some embodiments, elements 512, 514, 516, or 518 may display one or more actions to be performed regarding one or more conditions associated with the genotype of the animal associated with interactive element 504 of FIG. 5A. While certain interactive elements are described above, these interactive elements are exemplary and other interactive elements may be used. Additionally, while certain elements are described above as interactive, these are exemplary, and other elements that are not interactive may be used.

While FIG. 5B depicts a non-limiting example of a user interface 500 after user input is received at interactive element 504, this is exemplary, and user interface 500 may display other elements and information associated with the animal in response to receiving user input at an interactive element, such as with regards to a phenotype of the animal associated with interactive element 508 of FIG. 5A.

Figure 5D:
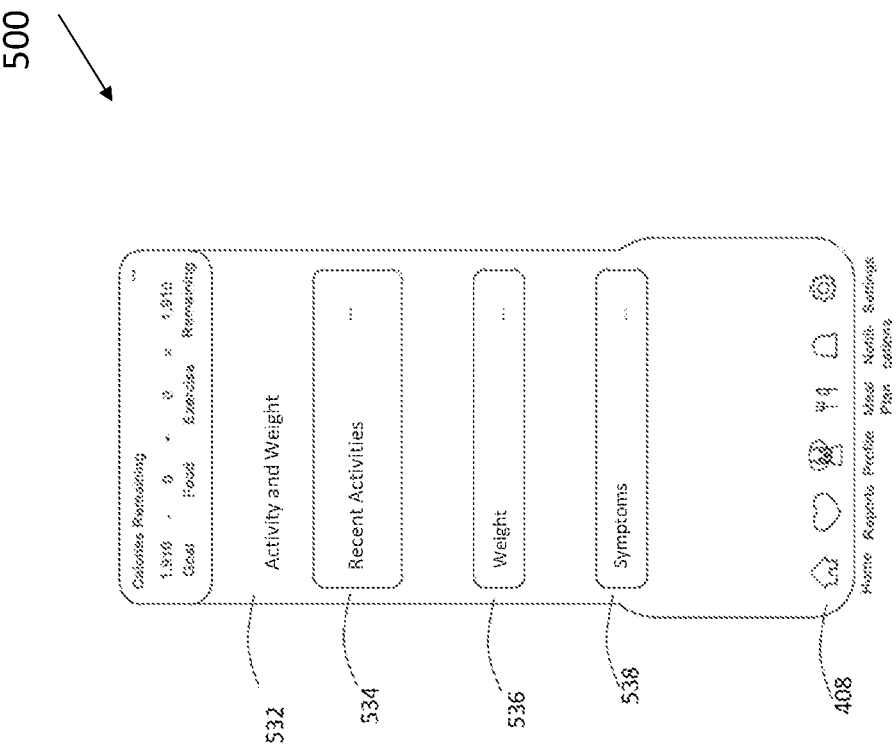
Figure 5C:
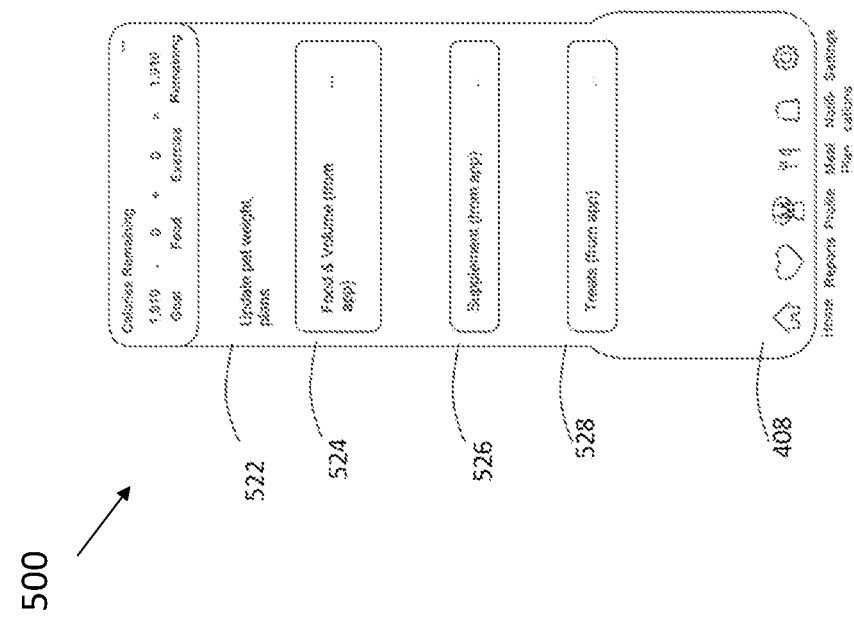

FIG. 5C depicts a non-limiting example of a user interface 500 after user input has been received by interactive element 408 (e.g., to the "Meal Plan" tab of interactive element 408). In this depicted embodiment, user interface 500 displays interactive elements 522, 524, 526, and 528. In this depicted embodiment, interactive element 524 is associated with the type and amount of food (e.g., meals), and may receive user input indicating a type and amount of food consumed by the animal. In this depicted embodiment, interactive element 526 is associated with the type and amount of supplements and may receive user input indicating one or more types and amounts of supplements consumed by the animal. In this depicted embodiment, interactive element 528 is associated with the type and amount of treats and may receive user input indicating one or more types and amounts of treats consumed by the animal. In some embodiments, user input to interactive elements 524, 526, and 528 may be used to augment consumption data associated with the animal. For example, a device (e.g., the second device 140 of FIG. 1) may receive consumption data such as the volume of an amount of food eaten by the animal, and user input to interactive element 524 may be used to indicate the type of food, which allows for the determination of the amount of calories consumed by the animal. In this depicted embodiment, interactive element 522 is associated with activity data and health data of the animal. While certain interactive elements are described above, these interactive elements are exemplary and other interactive elements may be used. Additionally, while certain elements are described above as interactive, these are exemplary, and other elements that are not interactive may be used.

FIG. 5D depicts a non-limiting example of a user interface 500 displaying elements 408, 532, 534, 536, and 538. In this depicted embodiment, user interface 500 displays elements 532, 534, 536, and 538 in response to user input received at interactive element 522 of FIG. 5C. In this depicted embodiment, elements 534, 536, and 538 are interactive. In this depicted embodiment, user input may be received at interactive element 534 regarding the activity data of the animal. In some embodiments, the activity data of the animal may be received from a first device (e.g., first device 130 of FIG. 1). In some embodiments, the user input to interactive element 534 may be used to augment the activity data of the animal. For example, user input to the interactive element 534 may include one or more types of exercises performed by the animal, which allows for a more accurate determination of the amount of calories burned by the animal during the exercise. In this depicted embodiment, user input may be received at interactive element 536 regarding the weight of the animal. In some embodiments, other attributes of the animal may be associated with interactive element 536. In some embodiments, the user input to interactive element 536 may be used to augment the activity data of the animal. For example, user input to the interactive element 536 may include an adjusted weight the animal, which allows for a more accurate determination of the amount of calories burned by the animal during exercise. In this depicted embodiment, user input may be received at interactive element 538 regarding the symptoms exhibited by the animal. In some embodiments, the user input to interactive element 536 may be used to augment the activity data or the profile of the animal. For example, user input to the interactive element 538 may include a new symptom exhibited by the animal, which allows for the profile to be adjusted based on the animal having or being at risk of developing one or more conditions based on the symptom. While certain interactive elements are described above, these interactive elements are exemplary and other interactive elements may be used. Additionally, while certain elements are described above as interactive, these are exemplary, and other elements that are not interactive may be used.

Figure 6A:
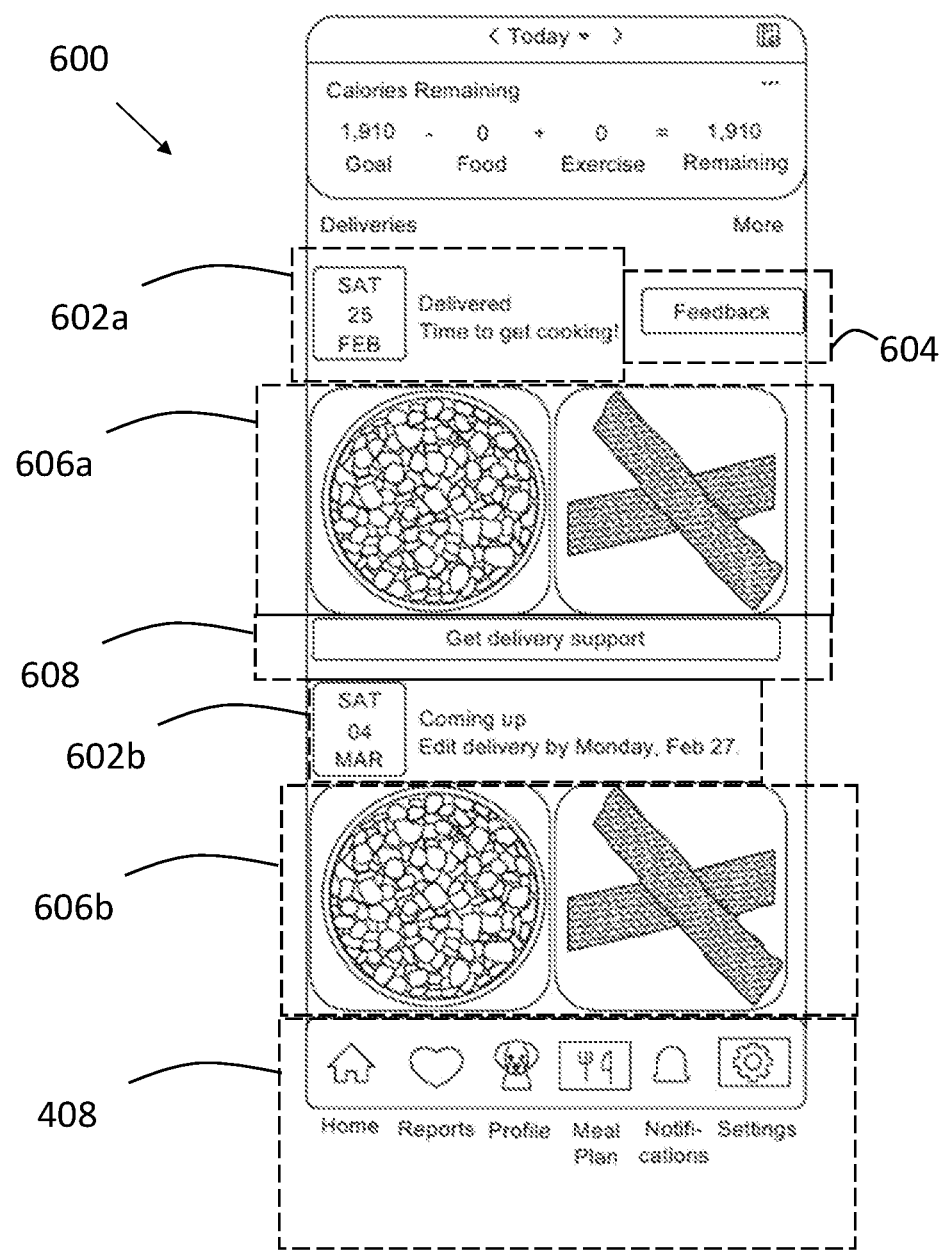
FIGS. 6A-6B depict non-limiting example GUIs for viewing one or more aspects of a profile, activity data, or consumption data.

FIG. 6A depicts a non-limiting example of user interface 600 for displaying wellness information regarding an animal. In some embodiments, user interface 600 may be displayed upon receiving user input to interactive element 408 (e.g., such as to the "Meal Plan" icon). In this depicted embodiment, user interface 600 displays elements 602a, 602b, 604, 606a, 606b, 608, and 408. In some embodiments, any number of elements 602a, 602b, 604, 606a, 606b, 608 may be interactive. In this depicted embodiment, elements 604 and 608 are interactive.

Figure 6B:
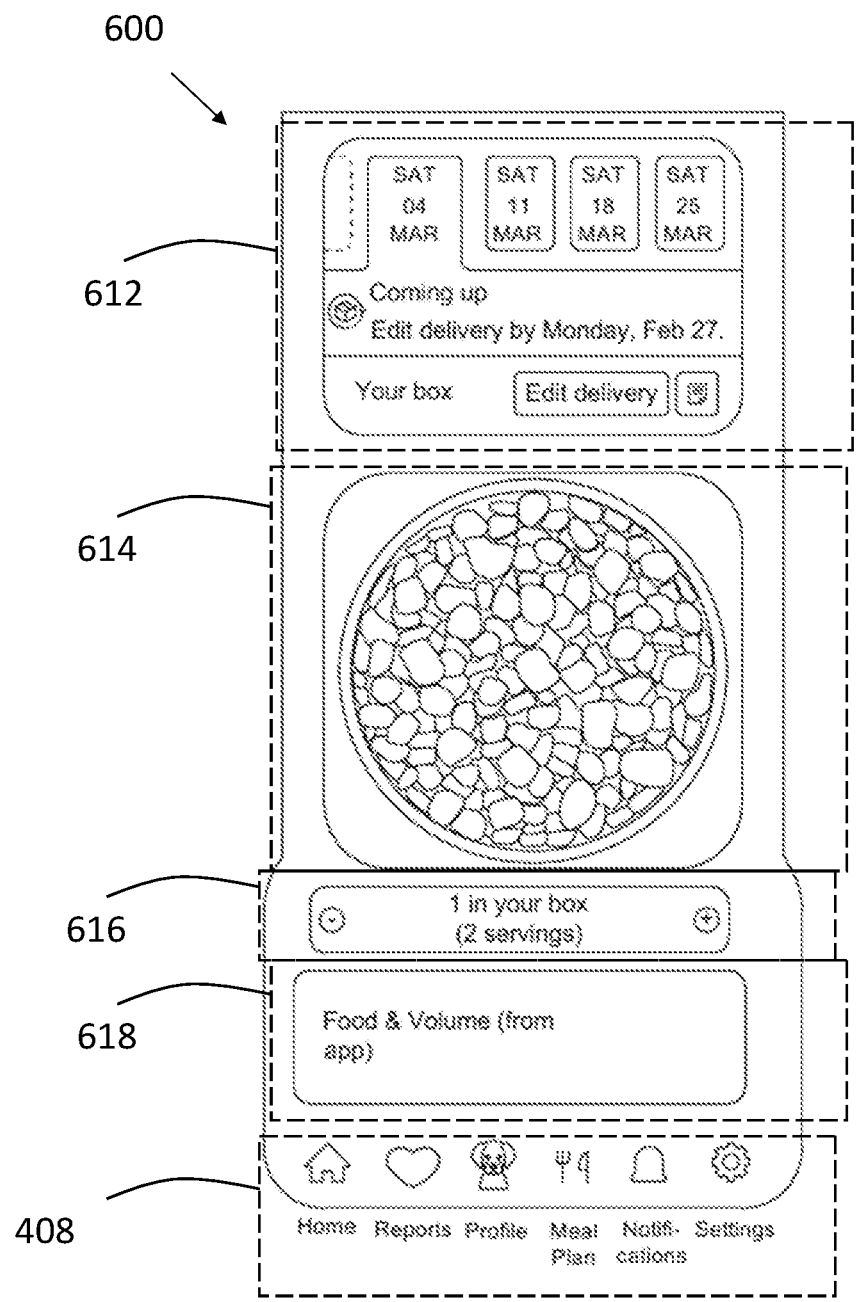

In this depicted embodiment, each of elements 602a, 602b, 604, 606a, 606b, 608, and 408 indicates one or more aspects of wellness information for an animal. For example, elements 602a and 602b indicate dates on which a shipment of food for the animal should arrive. Additionally, elements 606a and 606b indicate the type of food that will be a part of the shipment. Further, in this depicted embodiment, element 606b is interactive, and may receive user input that may cause the computing device to display one or more other elements not depicted in this example (as shown in FIG. 6B). Element 604 indicates that a user of a computing device displaying the user interface (e.g., computing device 130 of FIG. 1) may provide feedback. In some embodiments, element 604 may be interactive, and may receive user input. In some embodiments, element 604 may cause the user interface 600 to display one or more new elements upon receiving user input. Similarly, element 608 indicates that a user of the computing device displaying the user interface may provide user input in order to receive delivery support.

FIG. 6B depicts a non-limiting example of user interface 600 for displaying wellness information regarding an animal. In some embodiments, user interface 600 may be displayed upon receiving user input to interactive element 408 (e.g., such as to the "Meal Plan" icon). In this depicted embodiment, user interface 600 displays elements 612, 614, 616, 618, and 408. In some embodiments, any number of elements 612, 614, 616, 618, and 408 may be interactive (e.g., configured to receive user input). In this depicted embodiment, elements 612, 616, 618, and 408 are interactive.

In this depicted example, each of elements 612, 614, 616, and 618 indicates one or more aspects of wellness information for an animal. For example, element 612 indicates deliveries of food on one or more dates. In this depicted embodiment, element 612 may further receive user input to display and/or edit information regarding a certain date or delivery. In this depicted embodiment, element 614 displays a picture of food associated with the one or more deliveries. In this depicted embodiment, element 616 indicates an amount of food that has been delivered to a guardian of the animal. In this depicted embodiment, element 616 may receive user input that indicates the user would like to increase or decrease the amount of food delivered. In this depicted embodiment, element 618 indicates a type and/or amount of food for the animal. In some embodiments, element 618 may receive user input, which may lead to user interface 600 to display one or more elements not depicted in this embodiment.

Figures 7A, 7B, 7C:
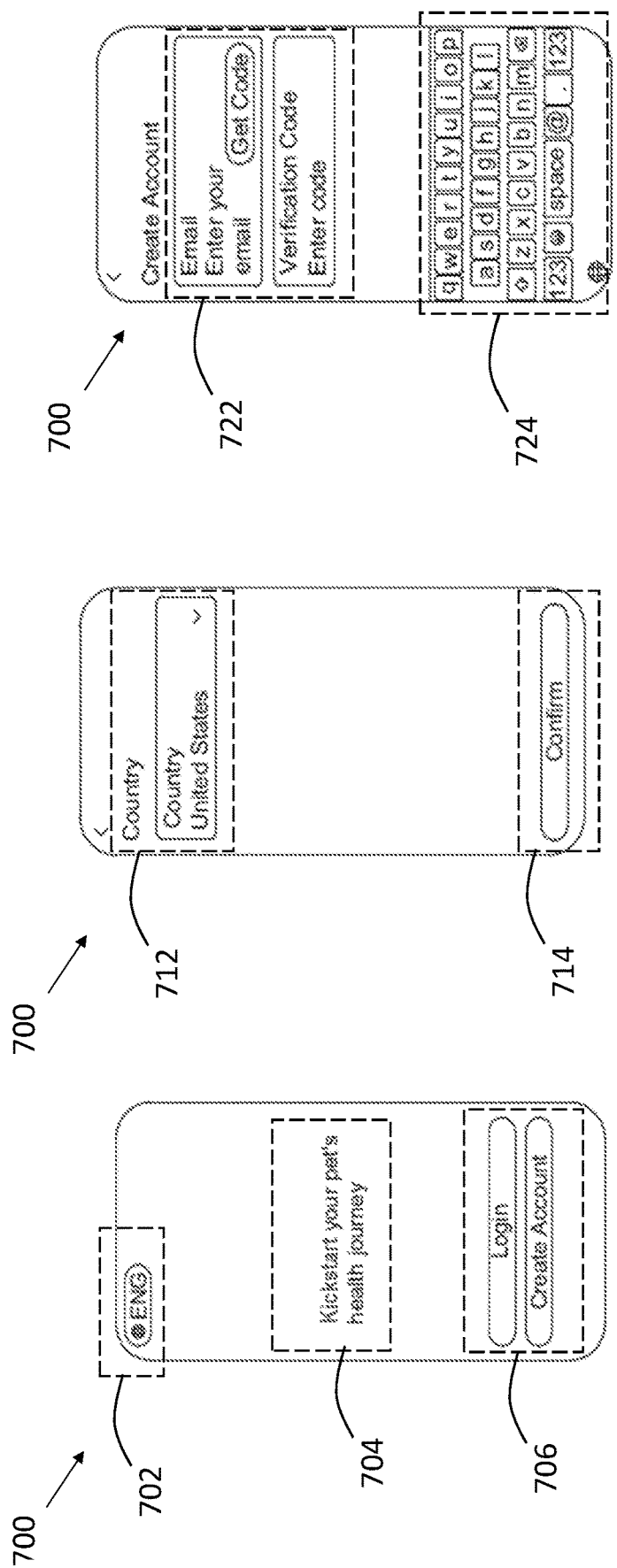
FIGS. 7A-7G depict non-limiting example GUIs for creating and/or accessing an account of an animal.

FIG. 7A depicts a non-limiting example of user interface 700 for setting up one or more accounts related to the wellness of an animal. In this depicted embodiment, user interface 700 displays elements 702, 704, and 706. In some embodiments, any number of elements 702, 704, and 706 may be interactive. In this depicted embodiments, elements 702 and 706 are interactive. In this depicted embodiment, element 702 indicates a language of the text displayed on interface 700. In this depicted embodiment, element 704 indicates an insight for guiding a user associated with user interface 700. In this depicted embodiment, element 706 may receive user input indicating that a user already has an account and would like to log into an application associated with the wellness of an animal (e.g., at the "login" element) or that the user would like to create an account (e.g., at the "create account" element). Upon receiving input to element 706, the user interface 700 may display one or more new elements not depicted in this example that are related to logging into the application or setting up an account.

FIG. 7B depicts a non-limiting example of user interface 700 for setting up one or more accounts related to the wellness of an animal. In this depicted embodiment, user interface 700 displays elements 712 and 714. In some embodiments, any number of elements 712 and 714 may be interactive. In this depicted embodiments, elements 712 and 714 are interactive. In this depicted embodiment, element 712 indicates the country where a user of a processing device displaying user interface 700 (e.g., computing device 120 of FIG. 1) is located, and may receive user input to change the country. In these depicted embodiments, element 714 may receive user input to confirm the country.

FIG. 7C depicts a non-limiting example of user interface 700 for setting up one or more accounts related to the wellness of an animal. In this depicted embodiment, user interface 700 displays elements 722 and 724. In some embodiments, any number of elements 722 and 724 may be interactive. In this depicted embodiments, elements 722 and 724 are interactive. In this depicted embodiment, element 722 may receive user input such as text input associated with an associated user's email as well as a code received by the user. In some embodiments, a processing device displaying the user interface 700 (e.g., server 110 or computing device 120 of FIG. 1) may provide a code after element 722 receives the user input.

Figure 7F:
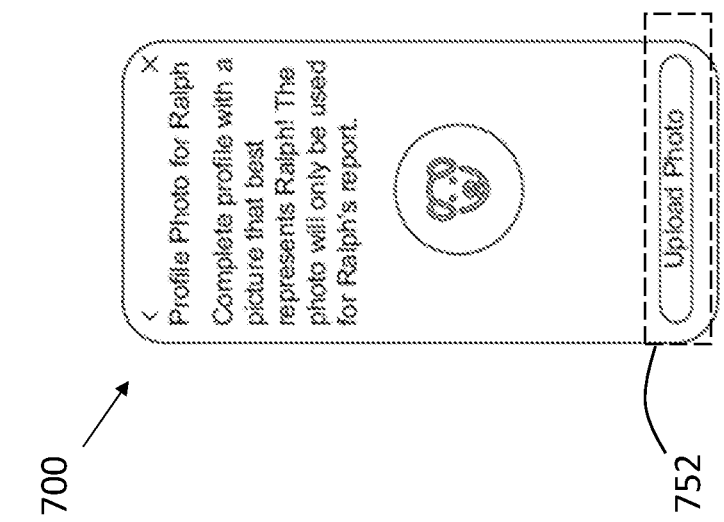
Figure 7E:
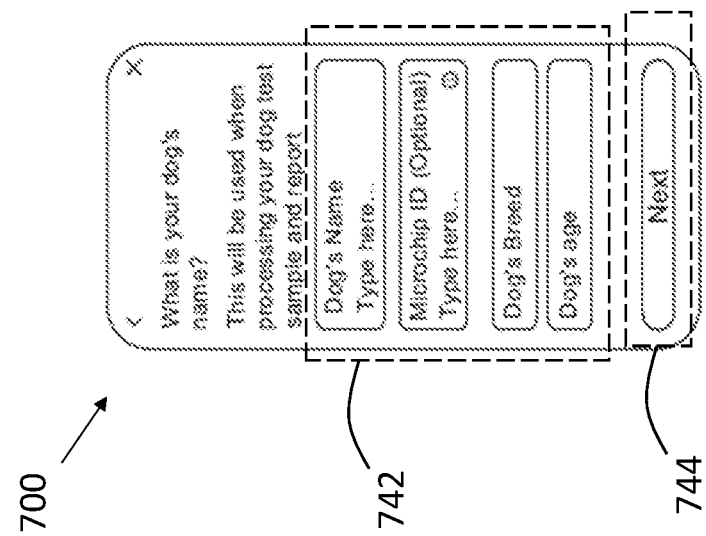
Figure 7D:
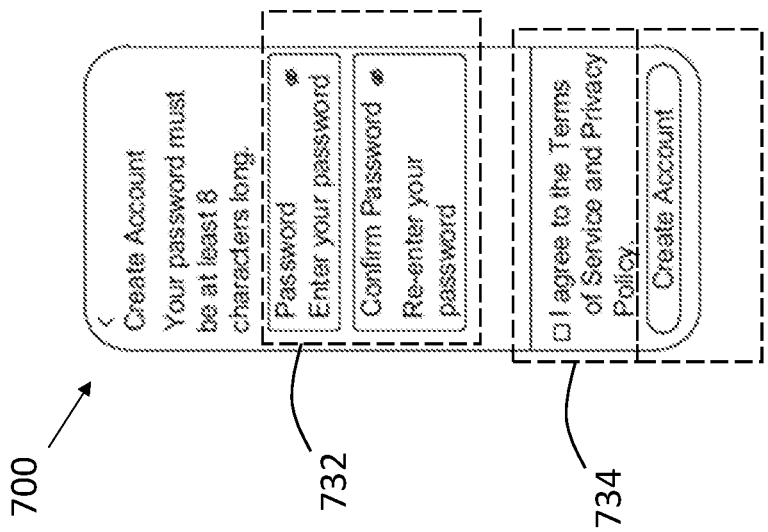

FIG. 7D depicts a non-limiting example of user interface 700 for setting up one or more accounts related to the wellness of an animal. In this depicted embodiment, user interface 700 displays elements 732 and 734. In some embodiments, any number of elements 732 and 734 may be interactive. In this depicted embodiments, elements 732 and 734 are interactive. In this depicted embodiment, element 732 may receive user input such as text input associated with an associated user's password as well as a code received by the user. In this depicted embodiment, element 734 may receive input regarding if a user agrees to the terms of service and privacy policy associated with creating an account.

FIG. 7E depicts a non-limiting example of user interface 700 for setting up one or more accounts related to the wellness of an animal. In this depicted embodiment, user interface 700 displays elements 742 and 744. In some embodiments, any number of elements 742 and 744 may be interactive. In this depicted embodiments, elements 742 and 744 are interactive. In this depicted embodiment, element 742 may receive user input associated with the animal such as the animal's name, ID, breed, and age. While certain user inputs are depicted, these are exemplary and others may be used (e.g., the weight of the animal). Element 744 may receive user input, and new elements not depicted may be displayed in user interface 700 upon element 744 receiving user input.

FIG. 7F depicts a non-limiting example of user interface 700 for setting up one or more accounts related to the wellness of an animal. In this depicted embodiment, user interface 700 displays element 752. In this depicted embodiment, element 752 is interactive. In this depicted embodiment, user input may be provided to element 752, which may cause another element not depicted to be displayed. The another element may then receive user input, such as an image of an animal.

Figure 7G:
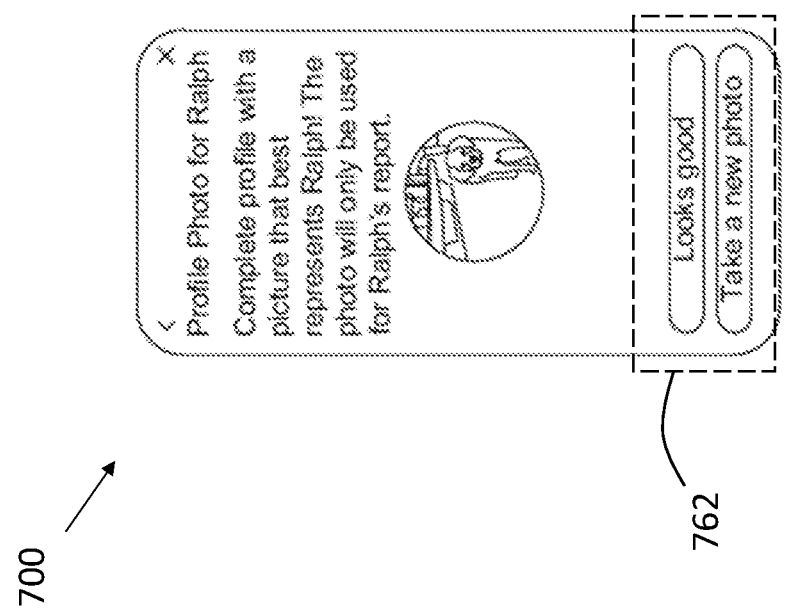

FIG. 7G depicts a non-limiting example of user interface 700 for setting up one or more accounts related to the wellness of an animal. In this depicted embodiment, user interface 700 displays element 762. In this depicted embodiment, element 762 is interactive. Element 762 may be displayed after an image is provided as user input to an element of user interface 700. Element 762 may receive user input confirming if the image should be used, or if another image should be provided. If user input indicating another image should be provided is provided, another element not depicted may be displayed that may receive the another image as user input.

Figure 8C:
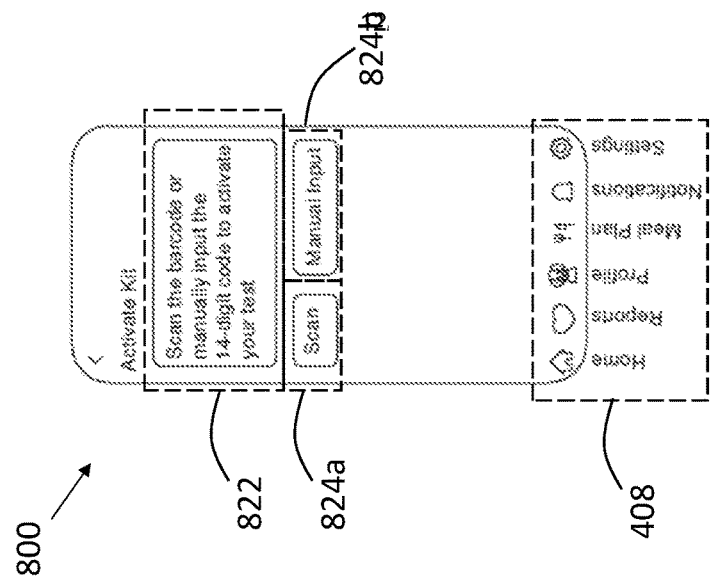
FIGS. 8A-8C depict non-limiting example GUIs for processes relating to collecting one or more samples for an animal.
Figure 8B:
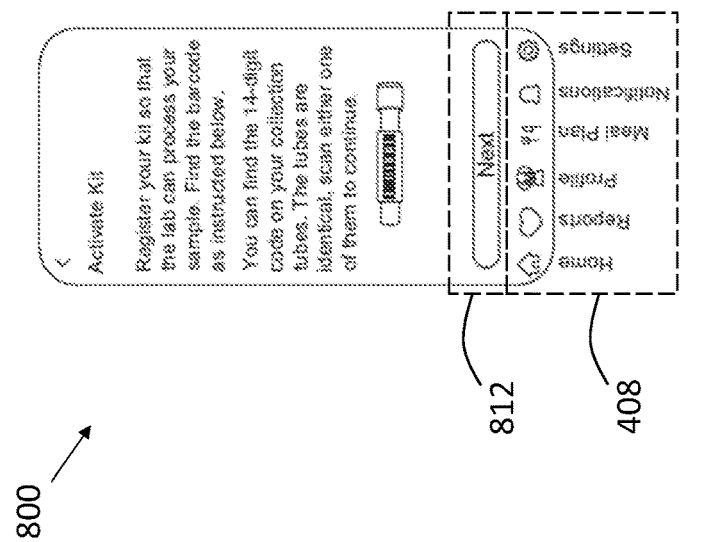
Figure 8A:
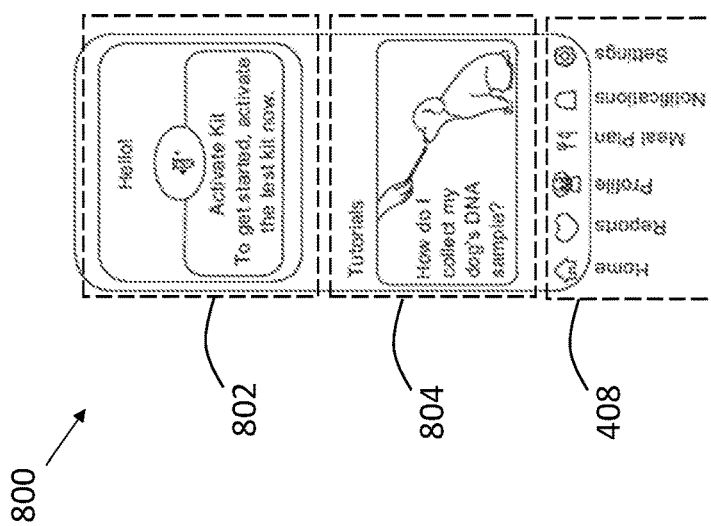

FIG. 8A depicts a non-limiting example of user interface 800 for assisting with collecting a DNA sample of an animal. In this depicted embodiment, user interface 800 displays elements 802, 804, and 408. In this depicted embodiment, elements 802, 804, and 408 are interactive. In this depicted embodiment, element 802 may receive user input relating to activating a kit to collect one or more samples from an animal, as described above. Element 804 may receive user input regarding tutorials for collecting the one or more samples, and one or more new elements may be displayed (e.g., an element displaying a video) upon element 804 receiving user input.

FIG. 8B depicts a non-limiting example of user interface 800 for assisting with collecting a DNA sample of an animal. In this depicted embodiment, user interface 800 displays elements 812 and 408. In this depicted embodiment, elements 812 and 408 are interactive. In this depicted embodiment, user interface 700 displays instructions for collecting one or more DNA samples from an animal. In this depicted embodiment, element 812 may receive user input, and one or more different views of user interface 800 may be displayed after element 812 receives the user input.

FIG. 8C depicts a non-limiting example of user interface 800 for assisting with collecting a DNA sample of an animal. In this depicted embodiment, user interface 800 displays elements 822, 824*a*, 824*b*, and 408. In this depicted embodiment, elements 824*a*, 824*b*, and 408 are interactive. In this depicted embodiment, element 822 displays instructions for scanning a barcode related to collecting the one or more samples. In this depicted embodiment, element 824*a* may receive user input, and after element 824*a* receives the user input, a computing device displaying user interface 800 (e.g., computing device 120 of FIG. 1) may perform one or more functions (e.g., allow use of a camera for scanning). In this depicted embodiment, element 824*b* may receive user input such as text input.

Figure 9:
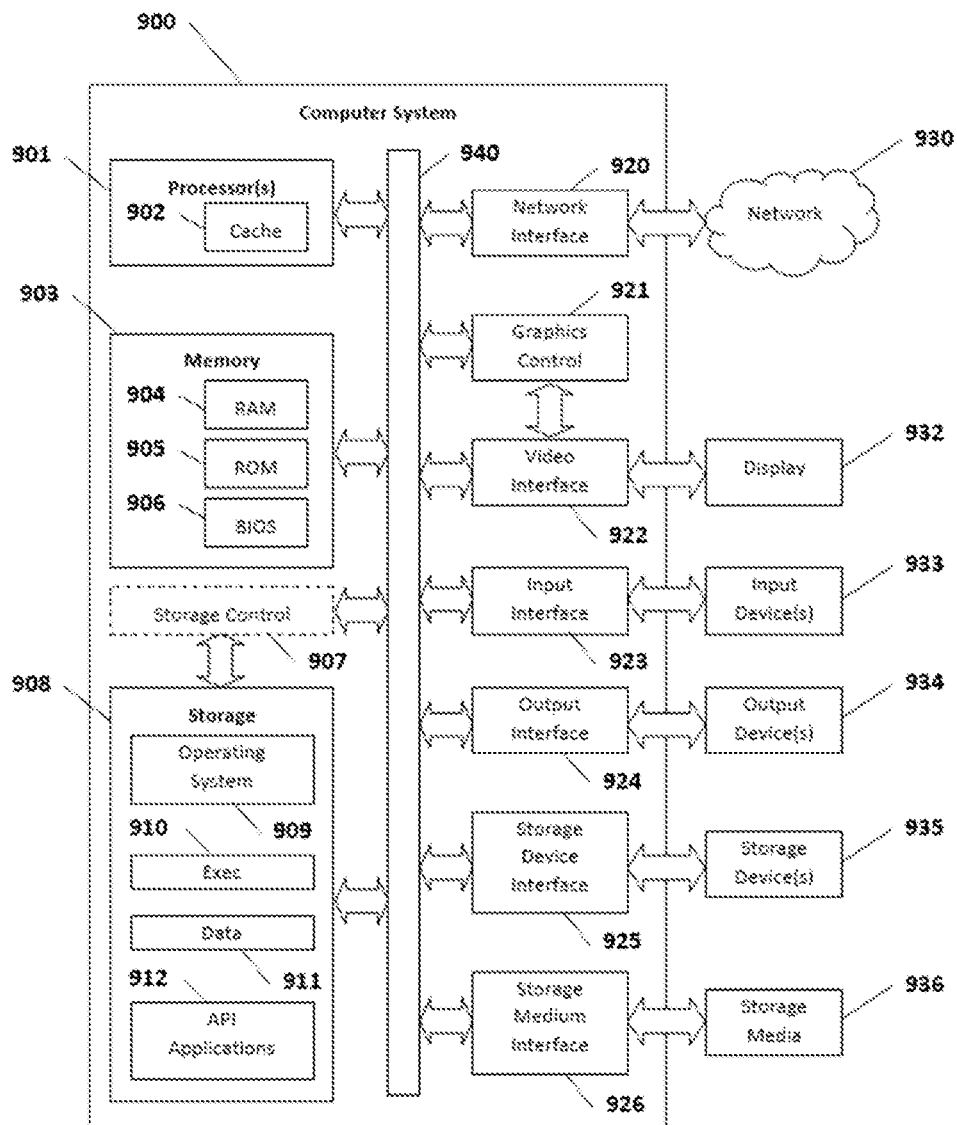
FIG. 9 shows a non-limiting example of a computing device; in this case, a device with one or more processors, memory, storage, and a network interface.

Referring to FIG. 9, a block diagram is shown depicting an exemplary machine that includes a computer system 900 (e.g., a processing or computing system) within which a set of instructions can execute for causing a device to perform or execute any one or more of the aspects and/or methodologies for static code scheduling of the present disclosure. The components in FIG. 9 are examples only and do not limit the scope of use or functionality of any hardware, software, embedded logic component, or a combination of two or more such components implementing particular embodiments.

Computer system 900 may include one or more processors 901, a memory 903, and a storage 908 that communicate with each other, and with other components, via a bus 940. The bus 940 may also link a display 932, one or more input devices 933 (which may, for example, include a keypad, a keyboard, a mouse, a stylus, etc.), one or more output devices 934, one or more storage devices 935, and various tangible storage media 936. All of these elements may interface directly or via one or more interfaces or adaptors to the bus 940. For instance, the various tangible storage media 936 can interface with the bus 940 via storage medium interface 926. Computer system 900 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 900 includes one or more processor(s) 901 (e.g., central processing units (CPUs), general purpose graphics processing units (GPGPUs), or quantum processing units (QPUs)) that carry out functions. Processor(s) 901 optionally contains a cache memory unit 902 for temporary local storage of instructions, data, or computer addresses. Processor(s) 901 are configured to assist in execution of computer readable instructions. Computer system 900 may provide functionality for the components depicted in FIG. 9 as a result of the processor(s) 901 executing non-transitory, processor-executable instructions embodied in one or more tangible computer-readable storage media, such as memory 903, storage 908, storage devices 935, and/or storage medium 936. The computer-readable media may store software that implements particular embodiments, and processor(s) 901 may execute the software. Memory 903 may read the software from one or more other computer-readable media (such as mass storage device(s) 935, 936) or from one or more other sources through a suitable interface, such as network interface 920. The software may cause processor(s) 901 to carry out one or more processes or one or more steps of one or more processes described or illustrated herein. Carrying out such processes or steps may include defining data structures stored in memory 903 and modifying the data structures as directed by the software.

The memory 903 may include various components (e.g., machine readable media) including, but not limited to, a random-access memory component (e.g., RAM 904) (e.g., static RAM (SRAM), dynamic RAM (DRAM), ferroelectric random access memory (FRAM), phase-change random access memory (PRAM), etc.), a read-only memory component (e.g., ROM 905), and any combinations thereof. ROM 905 may act to communicate data and instructions unidirectionally to processor(s) 901, and RAM 904 may act to communicate data and instructions bidirectionally with processor(s) 901. ROM 905 and RAM 904 may include any suitable tangible computer-readable media described below. In one example, a basic input/output system 906 (BIOS), including basic routines that help to transfer information between elements within computer system 900, such as during start-up, may be stored in the memory 903.

Fixed storage 908 is connected bidirectionally to processor(s) 901, optionally through storage control unit 907. Fixed storage 908 provides additional data storage capacity and may also include any suitable tangible computer-readable media described herein. Storage 908 may be used to store operating system 909, executable(s) 910, data 911, applications 912 (application programs), and the like. Storage 908 can also include an optical disk drive, a solid-state memory device (e.g., flash-based systems), or a combination of any of the above. Information in storage 908 may, in appropriate cases, be incorporated as virtual memory in memory 903.

In one example, storage device(s) 935 may be removably interfaced with computer system 900 (e.g., via an external port connector (not shown)) via a storage device interface 925. Particularly, storage device(s) 935 and an associated machine-readable medium may provide non-volatile and/or volatile storage of machine-readable instructions, data structures, program modules, and/or other data for the computer system 900. In one example, software may reside, completely or partially, within a machine-readable medium on storage device(s) 935. In another example, software may reside, completely or partially, within processor(s) 901.

Bus 940 connects a wide variety of subsystems. Herein, reference to a bus may encompass one or more digital signal lines serving a common function, where appropriate. Bus 940 may be any of several types of bus structures including, but not limited to, a memory bus, a memory controller, a peripheral bus, a local bus, and any combinations thereof, using any of a variety of bus architectures. As an example, and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 900 may also include an input device 933. In one example, a user of computer system 900 may enter commands and/or other information into computer system 900 via input device(s) 933. Examples of an input device(s) 933 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 933 may be interfaced to bus 940 via any of a variety of input interfaces 923 (e.g., input interface 923) including, but not limited to, serial, parallel, game port, USB, FIREWIRE, THUNDERBOLT, or any combination of the above.

In particular embodiments, when computer system 900 is connected to network 930, computer system 900 may communicate with other devices, specifically mobile devices and enterprise systems, distributed computing systems, cloud storage systems, cloud computing systems, and the like, connected to network 930. Communications to and from computer system 900 may be sent through network interface 920. For example, network interface 920 may receive incoming communications (such as requests or responses from other devices) in the form of one or more packets (such as Internet Protocol (IP) packets) from network 930, and computer system 900 may store the incoming communications in memory 903 for processing. Computer system 900 may similarly store outgoing communications (such as requests or responses to other devices) in the form of one or more packets in memory 903 and communicated to network 930 from network interface 920. Processor(s) 901 may access these communication packets stored in memory 903 for processing.

Examples of the network interface 920 include, but are not limited to, a network interface card, a modem, and any combination thereof. Examples of a network 930 or network segment 930 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 930, may employ a wired and/or a wireless mode of communication. In general, any network topology may be used.

Information and data can be displayed through a display 932. Examples of a display 932 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 932 can interface to the processor(s) 901, memory 903, and fixed storage 908, as well as other devices, such as input device(s) 933, via the bus 940. The display 932 is linked to the bus 940 via a video interface 922, and transport of data between the display 932 and the bus 940 can be controlled via the graphics control 921. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 932, computer system 900 may include one or more other peripheral output devices 934 including, but not limited to, an audio speaker, a printer, a storage device, and any combinations thereof. Such peripheral output devices may be connected to the bus 940 via an output interface 924. Examples of an output interface 924 include, but are not limited to, a serial port, a parallel connection, a USB port, a FIREWIRE port, a THUNDERBOLT port, and any combinations thereof.

In addition, or as an alternative, computer system 900 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art. In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Sony® PS5®, Microsoft® Xbox 360®, Microsoft® Xbox One, Microsoft® Xbox Series X, Microsoft® Xbox Series S, Nintendo® Wii®, Nintendo® Wii U®, Nintendo® Switch™, and Ouya®.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, XML, and document-oriented database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash® ActionScript, JavaScript, or Silverlight®. In some embodiments, a web application is written to some extent in a server-side coding language such as Active Server Pages (ASP), ColdFusion®, Perl, Java™ JavaServer Pages (JSP), Hypertext Preprocessor (PUP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 10:
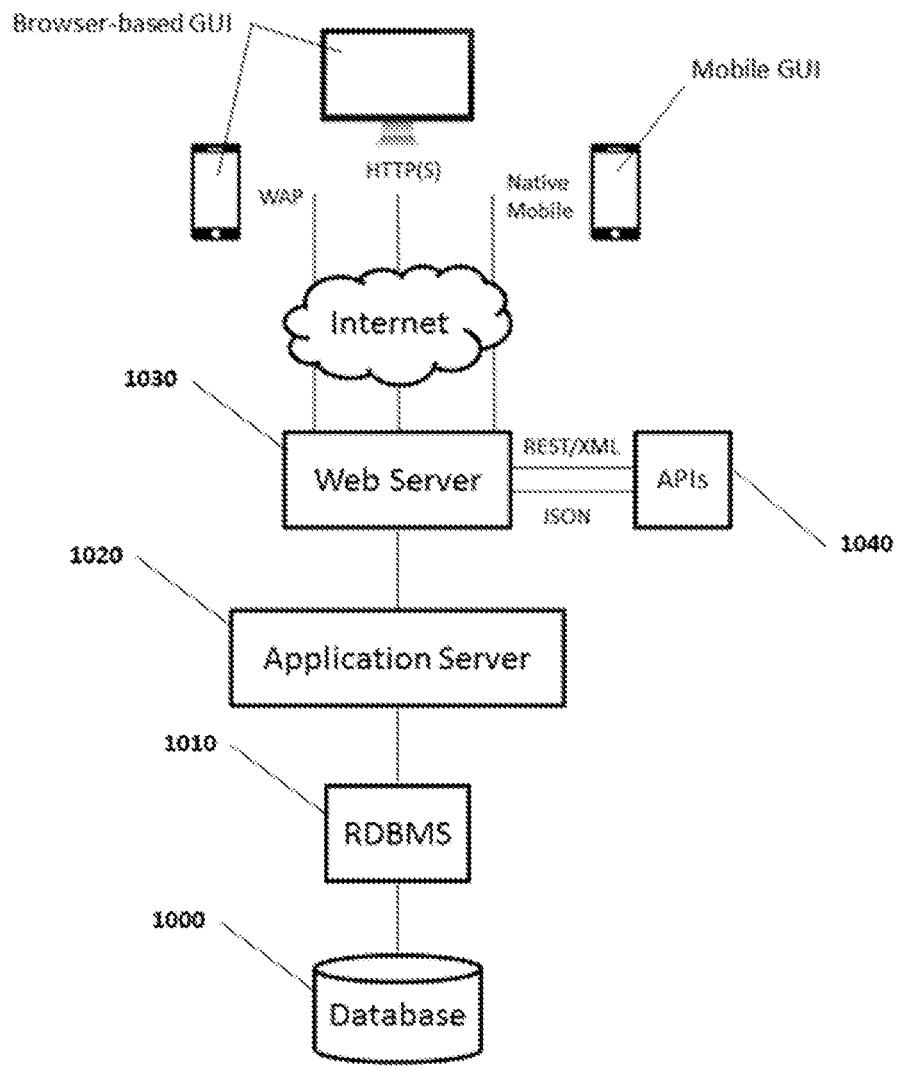
FIG. 10 shows a non-limiting example of a web/mobile application provision system; in this case, a system providing browser-based and/or native mobile user interfaces.

Referring to FIG. 10, in a particular embodiment, an application provision system comprises one or more databases 1000 accessed by a relational database management system (RDBMS) 1010. Suitable RDBMSs include Firebird, MySQL, PostgreSQL, SQLite, Oracle Database, Microsoft SQL Server, IBM DB2, IBM Informix, SAP Sybase, Teradata, and the like. In this embodiment, the application provision system further comprises one or more application severs 1020 (such as Java servers, NET servers, PUP servers, and the like) and one or more web servers 1030 (such as Apache, IIS, GWS and the like). The web server(s) optionally expose one or more web services via app application programming interfaces (APIs) 1040. Via a network, such as the Internet, the system provides browser-based and/or mobile native user interfaces.

Figure 11:
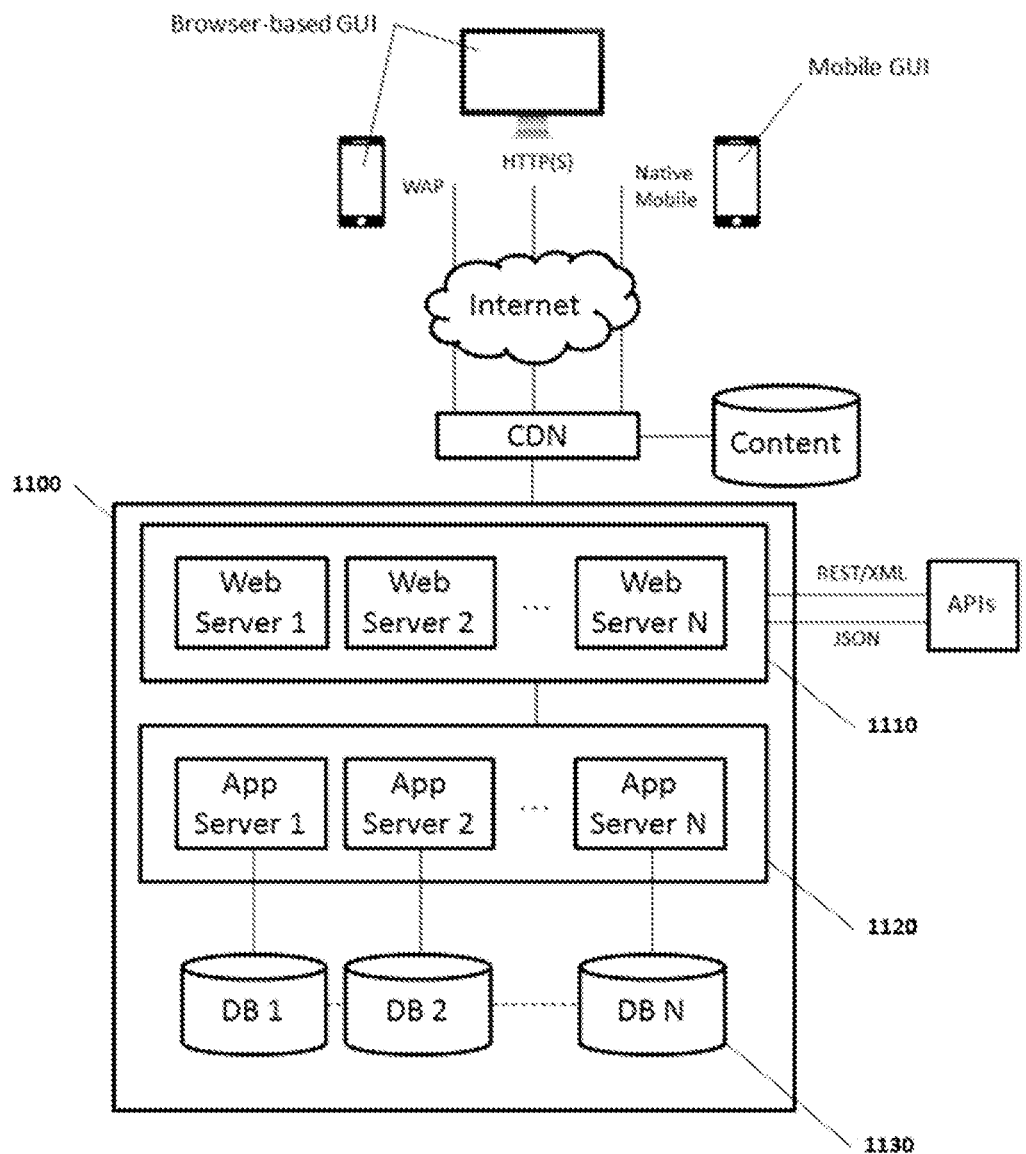
FIG. 11 shows a non-limiting example of a cloud-based web/mobile application provision system; in this case, a system comprising an elastically load balanced, auto-scaling web server and application server resources as well as synchronously replicated databases.

Referring to FIG. 11, in a particular embodiment, an application provision system alternatively has a distributed, cloud-based architecture 1100 and comprises elastically load balanced, auto-scaling web server resources 1110 and application server resources 1120 as well synchronously replicated databases 1130.

Mobile Application

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, JavaScript, Pascal, Object Pascal, Python™, Ruby, Rails, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB NET, or combinations thereof.

Web browsers (also called Internet browsers) are software applications, designed for use with network-connected computing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile computing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, a distributed computing resource, a cloud computing resource, or combinations thereof. In further various embodiments, a software module comprises a plurality of files, a plurality of sections of code, a plurality of programming objects, a plurality of programming structures, a plurality of distributed computing resources, a plurality of cloud computing resources, or combinations thereof. In various embodiments, the one or more software modules comprise, by way of non-limiting examples, a web application, a mobile application, a standalone application, and a distributed or cloud computing application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of genotype and phenotype information. In various embodiments, suitable databases include, by way of non-limiting examples, relational databases, non-relational databases, object-oriented databases, object databases, entity-relationship model databases, associative databases, XML databases, document-oriented databases, and graph databases. Further non-limiting examples include SQL, PostgreSQL, MySQL, Oracle, DB2, Sybase, and MongoDB. In some embodiments, a database is Internet-based. In further embodiments, a database is web-based. In still further embodiments, a database is cloud computing-based. In a particular embodiment, a database is a distributed database. In other embodiments, a database is based on one or more local computer storage devices.

Data Transmission

The subject matter described herein, including methods for producing a genotype-phenotype profile and a wellness probability score are configured to be performed in one or more facilities at one or more locations. Facility locations are not limited by country and include any country or territory. In some instances, one or more steps are performed in a different country than another step of the method. In some instances, one or more steps for obtaining a sample are performed in a different country than one or more steps for detecting the presence or absence of a genotype in a biological sample. In some embodiments, one or more method steps involving a computer system are performed in a different country than another step of the methods provided herein. In some embodiments, data processing and analyses are performed in a different country or location than one or more steps of the methods described herein. In some embodiments, one or more articles, products, or data are transferred from one or more of the facilities to one or more different facilities for analysis or further analysis. An article includes, but is not limited to, one or more components obtained from a subject, e.g., processed cellular material. Processed cellular material includes, but is not limited to, cDNA reverse transcribed from RNA, amplified RNA, amplified cDNA, sequenced DNA, isolated and/or purified RNA, isolated and/or purified DNA, and isolated and/or purified polypeptide. Data includes, but is not limited to, information regarding the stratification of a subject, and any data produced by the methods disclosed herein. In some embodiments of the methods and systems described herein, the analysis is performed and a subsequent data transmission step will convey or transmit the results of the analysis. In some embodiments, any step of any method described herein is performed by a software program or module on a computer. In additional or further embodiments, data from any step of any method described herein is transferred to and from facilities located within the same or different countries, including analysis performed in one facility in a particular location and the data shipped to another location or directly to an individual in the same or a different country. In additional or further embodiments, data from any step of any method described herein is transferred to and/or received from a facility located within the same or different countries, including analysis of a data input, such as genetic or processed cellular material, performed in one facility in a particular location and corresponding data transmitted to another location, or directly to an individual, such as data related to the genotype-phenotype profile to identify a non-human subject as having one or more conditions or a risk of developing one or more conditions the wellness probability score (WPS), and the recommendations for products, behaviors, and therapeutic or prophylactic intervention, or the like, in the same or different location or country.

Business Methods Utilizing a Computer

The methods described herein may utilize one or more computers. The computer may be used for managing customer and biological sample information such as sample or customer tracking, database management, analyzing molecular profiling data, analyzing cytological data, storing data, billing, marketing, reporting results, storing results, or a combination thereof. The computer may include a monitor or other user interface for displaying data, results, billing information, marketing information (e.g., demographics), customer information, or sample information. The computer may also include means for data or information input. The computer may include a processing unit and fixed or removable media or a combination thereof. The computer may be accessed by a user in physical proximity to the computer, for example via a keyboard and/or mouse, or by a user that does not necessarily have access to the physical computer through a communication medium such as a modem, an internet connection, a telephone connection, or a wired or wireless communication signal carrier wave. In some cases, the computer may be connected to a server or other communication device for relaying information from a user to the computer or from the computer to a user. In some cases, the user may store data or information obtained from the computer through a communication medium on media, such as removable media. It is envisioned that data relating to the methods can be transmitted over such networks or connections for reception and/or review by a party. The receiving party can be but is not limited to an individual, a health care provider (e.g., veterinarian) or a health care manager. In one embodiment, a computer-readable medium includes a medium suitable for transmission of a result of an analysis of a biological sample, such as a genotype. The medium can include a result regarding a genotype of a subject, wherein such a result is derived using the methods described herein.

The entity obtaining a report with the genotype-phenotype profile may enter biological sample information into a database for the purpose of one or more of the following: inventory tracking, assay result tracking, order tracking, customer management, customer service, billing, and sales. Sample information may include, but is not limited to: customer name, unique customer identification, customer associated veterinarian, indicated assay or assays, assay results, adequacy status, indicated adequacy tests, medical history of the non-human subject, preliminary diagnosis, suspected diagnosis, sample history, third party testing center or any information suitable for storage in a database. Sample history may include but is not limited to: age of the sample, type of sample, method of acquisition, method of storage, or method of transport.

The database may be accessible by a customer, medical professional, or other third party. Database access may take the form of electronic communication such as a computer or telephone. The database may be accessed through an intermediary such as a customer service representative, business representative, consultant, independent testing center, or medical professional. The availability or degree of database access or sample information, such as assay results, may change upon payment of a fee for products and services rendered or to be rendered.

Sample Processors

Disclosed herein are systems for automated processing of a sample from a subject. In some embodiments, the samples from a subject are collected as a part of a kit. In some embodiments, the samples from a subject are collected by a guardian or a veterinarian. In some embodiments, the automated system scans the barcode associated with the sample to track the sample through processing. In some embodiments, the sample is processed alongside other samples. In some embodiments, the samples are processed alongside one another in a 96-well plate. In some embodiments, the system comprises a blood spot card, which can retain a sample obtained from a subject (e.g., a blood sample), and transported to a laboratory facility for processing and biomarker detection. In some embodiment, the systems comprise a device for detecting the one or biomarkers disclosed herein, such as a genotype device.

Kits

Disclosed herein are kits for use in determining the genotype and/or phenotype of a subject. In some embodiments, the kits are for use in sample collection. In some embodiments, the kit is for collection of a buccal sample from the subject. In some embodiments, the kit for collecting a buccal sample comprises a sterile swab, a sterile container for said swab, and instruction of use. In some embodiments, the kit for collecting a buccal sample further comprises packaging for shipping the buccal sample. In some embodiments, the swab is a cotton swab. In some embodiments, the swab is a flocked nylon swab. In some embodiments, the swab is a polyurethane foam swab. In some embodiments, the swab is a rayon swab. In some embodiments, the swab is an OmniSwab. In some embodiments, the swab is a bristled swab. In some embodiments, the swab has a break point. In some embodiments, the entire swab is placed in said sterile container. In some embodiments, the swab tip is broken off in said sterile container. In some embodiments, the sterile container contains a barcode. In some embodiments, the sterile container contains a liquid. In some embodiments, the liquid is a buffer. In some embodiments, the liquid is a preservative. In some embodiments, the liquid is a nucleic acid protectant. In some embodiments, the kit is for collection of a blood spot from the subject. In some embodiments, the kit for collecting a blood spot comprises a dried blood card, a sterile needle, and instruction of use. In some embodiments, the kit for collecting a blood spot further comprises packaging for shipping the dried blood card. In some embodiments, the kit for collecting a blood spot further comprises an alcohol prep wipe. In some embodiments, the dried blood card contains a barcode. In some embodiments, the dried blood card contains multiple areas for which to add blood. In some embodiments, the needle is a lancet. In some embodiments, the kit is for collecting a hair and follicle sample from a subject. In some embodiments, the kit for collecting a hair and follicle sample comprises a hair collection card and instructions of use. In some embodiments, the kit for collecting a hair and follicle sample further comprises packaging for shipping the hair collection card. In some embodiments, the hair collection card contains a barcode. In some embodiments, a guardian will use the kit on a subject. In some embodiments, a veterinarian will use the kit on a subject.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the term "breed" with reference to a canine or feline subject should be interpreted consistent with the guidelines defined by the American Kennel Club® (AKC), Continental Kennel Club (CKC), The Cat Fanciers' Association (CFA), or American Veterinary Medical Association® (AVMA).

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject" encompass animals. Non-limiting examples of animals include any mammalian class, reptiles, amphibians, and marsupials.

The term "gene," as used herein, refers to a segment of nucleic acid that encodes an individual protein or RNA (also referred to as a "coding sequence" or "coding region"), optionally together with associated regulatory region such as promoter, operator, terminator and the like, which may be located upstream or downstream of the coding sequence. A "genetic locus" referred to herein, is a particular location within a gene or intergenic region (non-coding).

The term, "genetic data" and "genotype" are used interchangeably as disclosed herein, and refers to the chemical composition of polynucleotide sequences within the genome of a subject. In some embodiments, the genotype comprises single nucleotide polymorphisms (SNPs), indels (insertion or deletion, of a nucleobase within a polynucleotide sequence), and/or copy number variants (CNVs). The term, "single nucleotide polymorphisms" or SNP, as disclosed herein, refers to a variation in a single nucleotide within a polynucleotide sequence. The variation of a SNP may have multiple different forms. A single form of an SNP is referred to as an "allele." By way of example, and without providing limitation, a reference polynucleotide sequence reading 5' to 3' is TTACG. A SNP at allele position 3 (of 5'-TTACG-3') comprise a substitution of the reference allele, "A" to a non-reference allele, "C." If the "C" allele of the SNP is associated with an increased probability of developing a phenotypic trait, the allele is considered a "risk" allele. However, the same SNP may also comprise a substitution of the "A" allele to a "T" allele. If the T allele of the SNP is associated with a decreased probability of developing a phenotypic trait, the allele is considered a "protective" allele. In some embodiments, the SNP is represented by an "rs" number, which refers to the accession of reference cluster of one or more submitted SNPs in a database, and which is characterized by a sequence that comprises the total number of nucleobases from 5' to 3', including the variation that was submitted. In some embodiments, a SNP may be further defined by the position of the SNP (nucleobase) within a provided sequence, the position of which is always located at the 5' length of the sequence plus 1. In some embodiments, a SNP is defined as the genomic position in a reference genome and the allele change (e.g., chromosome 3 at position 89,040,160 from A allele to G allele). The term, "indel," as disclosed herein, refers to an insertion, or a deletion, of a nucleobase within a polynucleotide sequence. In some embodiments, the indel is represented by an "rs" number, which refers to the accession of reference cluster of one more submitted indels in a database, and which is characterized by a sequence that comprises the total number of nucleobases from 5' to 3', including the variation that was submitted. In some embodiments, an indel may be further defined by the position of the insertion/deletion within a provided sequence, the position of which is always located at the 5' length of the sequence plus 1. In some embodiments, an indel is defined as the genomic position in a reference genome and the allele change. In some embodiments, the indel is defined as the genomic position identified with [brackets] in a sequence disclosed herein. The term "copy number variant" or "copy number variation" or "CNV" disclosed herein, refers a phenomenon in which sections of a polynucleotide sequence are repeated or deleted, the number of repeats in the genome varying between individuals in a given population. In some embodiments, the section of the polynucleotide sequence is "short," comprising about two nucleotides (bi-nucleotide CNV) or three nucleotides (tri-nucleotide CNV). In some embodiments, the section of the polynucleotide sequence is "long," comprising a number of nucleotides between four nucleotides and an entire length of a gene.

A "polymorphism" as used herein refers to an aberration in (e.g., a mutation), or of (e.g., insertion/deletion), a nucleic acid sequence, as compared to the nucleic acid sequence in a reference population. In some embodiments, the polymorphism is common in the reference population. In some embodiments, the polymorphism is rare in the reference population. In some embodiments, the polymorphism is a single nucleotide polymorphism.

The terms "phenotypic data," and "phenotype" are used interchangeably herein to refer to an observable characteristic and/or an environmental characteristic of a subject. In some cases, a specific phenotype adversely affects the health or wellness of the subject.

The term "biomarker" comprises a measurable substance in a subject whose presence, level, or activity, is indicative of a phenomenon (e.g., phenotypic expression or activity; disease, condition, subclinical phenotype of a disease or condition, infection; or environmental stimuli). In some embodiments, a biomarker comprises a gene, gene expression product (e.g., RNA or protein), a sugar, lipid, hormone, vitamin, metabolite, electrolyte, or a cell or cell-type (e.g., red blood cell).

The term "genotype-phenotype profile" comprises a combination of characteristics present in both a genetic data and a phenotypic data for a subject. Non-limiting examples of a potential genotype-phenotype profile comprises data from polymorphisms (e.g., SNPS or indels) while the phenotypic data comprises data from physical attributes (e.g., breed, age, sex, weight).

The section headings used herein are for organizational purposes only and are not to be construed as limiting the subject matter described.

EXAMPLES

The following examples are included for illustrative purposes only and are not intended to limit the scope of the inventive concept.

Example 1: Labrador Retriever Wellness System

The guardian of a 7-year-old male, neutered Labrador retriever signs up for a personalized wellness system. Once the guardian signs up for the personalized wellness system, the guardian answers a questionnaire about their dog including details about their dog's weight, activity level, and stool on the application (App) for the personalized wellness system. In addition to the questionnaire, the guardian receives a collection kit and instructions to swab their dog's cheeks.

In the questionnaire on the App, the guardian indicates that their dog is largely sedentary and infrequently takes walks, currently eats a beef-based dog food, weighs 104 pounds and is obese, and becomes itchy in humid weather but otherwise has no obvious allergies or dietary issues.

After the guardian swabs their dog's cheeks, a genotype assay is performed on the swab of the dog. The DNA profiling assay indicates that their dog's DNA contains SNP rs22114085 and MED13(Chr 9) polymorphism as in Wood et al. (Immunogenetics (2009) 61:765-772) and Wang et al. (BMC Genomics (2021) 22:636), respectively. The SNP rs22114085 is associated with atopic dermatitis in dogs. The MED13(Chr 9) polymorphism is associated with a risk of hip dysplasia.

The phenotype information (e.g., weight, activity level, and stool) and the results from the genotype test are combined to create a phenotype-genotype profile for the dog. The phenotype-genotype profile is input into a clustering algorithm that clusters the dog for each observation, including clusters for a high, moderate, or low likelihood of having or developing atopic dermatitis and clusters for a high, moderate, or low likelihood of having or developing hip dysplasia.

The clustering algorithm outputs three clusters: a high likelihood of having or developing atopic dermatitis, a high likelihood of having or developing hip dysplasia, and a high likelihood of having or developing obesity.

The algorithmic analysis cluster labels carrier status of SNP rs22114085 (heterozygous for risk allele) as an exclusive need. This exclusive need calls for the elimination of certain high-risk protein sources known to increase the risk of a dermatitis reaction. An algorithmic analysis cluster labels carrier status of a SNP at the MED13 locus as an inclusive need. This inclusive need calls for the use of a joint supplement, preferably, beginning at an early age. The dog's weight and activity level calls for a weight-management strategy.

Another algorithm retrieves from a data base a list of proteins not excluded by the risk of dermatitis with the minimum caloric needs of a 104-pound neutered male dog to lose weight. The algorithm also includes a glucosamine supplement for joint health. A recommendation is generated by the algorithm to switch the dog's current diet with a diet comprising one or more of the proteins provided on the list in an amount that will help the dog lose weight at a safe rate. In this example the proteins are fish, duck or lamb and the amount is 114 grams of kibble twice daily. Another recommendation is generated to add to the dog's current diet the glucosamine supplement daily to increase joint health and prevent the hip dysplasia.

The personalized wellness system automatically uploads the recommendations to the App, where it is visible to the guardian via their smart phone. To access the genotypic and phenotypic information, the guardian will launch the personalized wellness system App. The bottom menu on the home page will include a 'Reports' icon. When the 'Reports' icon is selected, the guardian will be able to review their dog's DNA report. When the 'Your Pet's DNA Report' is selected, the guardian will be directed to an interface that provides information on the genotypic and phenotypic needs. The guardian can select the different genotypic and phenotypic needs of their dog to learn more about the selected need and how different factors can affect that need. The guardian can also select 'Meal Recommendations' to determine what food and supplements and in what amounts are recommended for their dog.

After 2 months following the initial recommendation, the guardian brings the dog to the veterinarian to get a checkup. The dog now weighs 100 pounds (has lost 4 pounds). The guardian updates their dog's weight in the App. The App uses the new weight and calculates that their dog now needs 115 grams of kibble which may contain fish, duck or lamb twice a day (an increase in 2 grams per feeding).

After 4 months from the second recommendation, the guardian has a blood test performed for the dog. This blood test may be performed at a veterinarian for the dog or at home using a point of need test kit. The dog's blood is drawn and analyzed for essential nutrients. The blood test reveals that all circulating levels of essential nutrients are within expected levels. The results of the blood test are uploaded to the personalized wellness system, which uses the results to provide an updated recommendation. The updated recommendation is the same as the former recommendation. The dog continues his current plan until new parameters are entered that change the existing recommendations for the dog's plan. These recommendations continue to change as the dog's needs change for the life of the dog while on the personalized wellness system.

Example 2: Domestic Short-Haired Feline Wellness System

The guardian of a 1-year-old female, spayed domestic short-haired feline signs up for a personalized wellness system. Once the guardian signs up for the personalized wellness system, the guardian answers a questionnaire about their cat including details about their cat's weight, activity level, and stool on the App for the personalized wellness system. In addition to the questionnaire, the guardian receives a collection kit and instructions to swab their cat's cheeks.

In the questionnaire on the App, the guardian indicates that their cat is spayed, is of average activity level, does not like beef-based foods, and does not display any symptoms/signs of conditions such as diabetes.

After the guardian swabs their cat's cheeks, a genotype assay is performed on the swab of the cat. The DNA profiling assay indicates that their cat's DNA contains SNP chrA2.4150731 as in Forcada et al. (PLoS One (2021) 16(12)). The SNP chrA2.4150731 is associated with diabetes mellitus risk in cats.

The phenotype information (e.g., weight, activity level, and stool) and the results from the genotype test are combined to create a phenotype-genotype profile for the cat. The phenotype-genotype profile is input into a clustering algorithm that clusters the cat for each observation, including clusters for a high, moderate, or low likelihood of having or developing diabetes mellitus.

The clustering algorithm outputs a cluster: a high likelihood of having or developing diabetes mellitus. The algorithmic analysis cluster labels carrier status of SNP chrA2.4150731 (heterozygous for risk allele) as an exclusive need. This exclusive need calls for weight and sugar management to avoid diabetes. The risk of weight gain reveals a phenotypic need for increased exercise.

Another algorithm retrieves from a data base a list of foods formulated for weight and glucose management and that do not contain beef. The algorithm recommends a weight and glucose management diet which may contain fish duck or chicken. The algorithm also recommends a daily fiber supplement to assist with glucose metabolism. The algorithm also recommends activity-stimulating toys to encourage increased activity along with a smart collar that acts as an activity tracker.

The personalized wellness system automatically uploads the recommendations to the App, where it is visible to the guardian via their smart phone. To access the genotypic and phenotypic information, the guardian will launch the personalized wellness system App. The bottom menu on the home page will include a 'Reports' icon. When the 'Reports' icon is selected, the guardian will be able to review their cat's DNA report. When the 'Your Pet's DNA Report' is selected, the guardian will be directed to an interface that provides information on the genotypic and phenotypic needs. The guardian can select the different genotypic and phenotypic needs of their cat to learn more about the selected need and how different factors can affect that need. The guardian can also select 'Meal Recommendations' to determine what food and supplements and in what amounts are recommended for their cat. Once the smart collar is activated, the cat's activity will be visible on the App by selecting the 'Reports' icon followed by 'Your Pet's Activity Report.' On the 'Your Pet's Activity Report' main page the guardian can not only view the cat's activity but also manually input information relating to their cat's activity and food consumption.

After a week of data collection from the smart collar, the App models the activity-related caloric intake from the cat and adjusts the caloric accordingly. The monitoring of the activity and the caloric intake of the cat will continue while on the personalized wellness system.

After 2 months on the personalized wellness system, the guardian brings the cat to the veterinarian to check the cat's fasting glucose. The guardian updates the App with the weight and results of the fasting glucose check. The cat is still within healthy weight and glucose levels. The App continues with its recommendations making no changes aside from those which merits alterations such as the automatic inputs by the smart collar or manual inputs from the guardian.

After 4 months from the second recommendation, the guardian has a blood test performed for the cat. This blood test may be performed at a veterinarian for the cat or at home using a point of need test kit. The cat's blood is drawn and analyzed for glucose levels. The blood test reveals that the fasting glucose levels for the cat are outside the normal range. The results of the blood test are uploaded to the personalized wellness system, which uses the results to provide an updated recommendation. From the new glucose results, the algorithm re-analyzes the parameter's associated with the cat to generate a reduced-sugar diet and increased supplementation. The guardian is notified of the new recommendations through the App. The recommendation has new food serving recommendations as well as additional vitamins to add as supplements to make up for the reduced caloric intake of the cat. This plan continues until new parameters are entered that change the existing recommendations for the cat's plan. These recommendations continue to change as the cat's needs change for the life of the cat while on the personalized wellness system.

Example 3: Mixed Breed Canine Wellness System

The guardian of a 2-year-old female, spayed mixed breed canine signs up for a personalized wellness system. Once the guardian signs up for the personalized wellness system, the guardian answers a questionnaire about their dog including details about their dog's weight, activity level, and stool on the App for the personalized wellness system. In addition to the questionnaire, the guardian receives a collection kit and instructions to swab their dog's cheeks.

In the questionnaire on the App, the guardian indicates that their dog is very active, frequently going on runs with them. The guardian also mentions that their dog is very treat motivated and that they often give the dogs treats.

After the guardian swabs their dog's cheeks, a genotype assay is performed on the swab of the dog. The DNA profiling assay indicates that their dog's DNA contains a deletion in immunoglobulin superfamily member 1 (IGSF1) gene as in Plassais et al. (PLOS Genetics (2017) 13(3)) which is associated with thyroid function and in turn influences growth and size in dogs.

The phenotype information (e.g., weight, activity level, and stool) and the results from the genotype test are combined to create a phenotype-genotype profile for the dog. The phenotype-genotype profile is input into a clustering algorithm that clusters the dog for each observation, including clusters for a high, moderate, or low likelihood of having or developing a thyroid condition.

The clustering algorithm outputs one cluster: a high likelihood of having or developing a thyroid condition. The algorithmic analysis cluster labels carrier status of the IGSF1 deletion as an inclusive need. This inclusive need calls for the use of a thyroid supplement containing L-tyrosine. The dog's increased activity and increased number of treats indicates a need to balance caloric intake appropriately.

Another algorithm retrieves from a data base a list of foods formulated for high activity dogs and pairs these options with complete and balanced treat options. The algorithm recommends a rotational diet comprising of beef, chicken, and seafood coupled with a rotating selection of training treats as well as a thyroid supplement. The algorithm also recommends support items for running with dogs such as belt leaches.

The personalized wellness system automatically uploads the recommendations to the App, where it is visible to the guardian via their smart phone. To access the genotypic and phenotypic information, the guardian will launch the personalized wellness system App. The bottom menu on the home page will include a 'Reports' icon. When the 'Reports' icon is selected, the guardian will be able to review their dog's DNA report. When the 'Your Pet's DNA Report' is selected, the guardian will be directed to an interface that provides information on the genotypic and phenotypic needs. The guardian can select the different genotypic and phenotypic needs of their dog to learn more about the selected need and how different factors can affect that need. The guardian can also select 'Meal Recommendations' to determine what food and supplements and in what amounts are recommended for their dog.

During the first week on the personalized wellness system the guardian is asked to indicate the number of treats being provided to their dog. After collecting the data for a week on guardian supplied treats, the App adjusts the recommended servings for the dog to account for the increased calories from treats. Following the initial treat number supplied in the first week, the App will continue to inquire as to the average number of treats supplied daily every month.

A month after starting the personalized wellness system, the guardian indicates on the App that their dog will be more active than usual for one week during their family camping trip. The guardian estimates the increase in activity level for the dog for that week and the App responds by generating a new caloric intake recommendation for the dog for that week. After the camping trip, the dog's caloric intake recommendations return to those given prior to the camping trip.

Five months after the camping trip, the guardian has a blood test performed for the dog. This blood test may be performed at a veterinarian for the dog or at home using a point of need test kit. The dog's blood is drawn and analyzed. The blood test reveals no items of concern. The results of the blood test are uploaded to the personalized wellness system, which uses the results to provide an updated recommendation. The updated recommendation is the same as the former recommendation. The dog continues her current plan until new parameters are entered that change the existing recommendations for the dog's plan. These recommendations continue to change as the dog's needs change for the life of the dog while on the personalized wellness system.

What is claimed is:

1. A method for identifying a nutritional product recommended for a non-human animal subject, the method comprising:
   (a) receiving genetic data at a plurality of genomic loci of the non-human animal subject, wherein at least one genomic locus of the plurality of genomic loci is associated with a first condition, wherein the first condition is not a breed type;
   (b) receiving phenotypic data pertaining to a plurality of phenotypes of the non-human animal subject, wherein at least one phenotype of the plurality of phenotypes is associated with a second condition;
   (c) producing a genotype-phenotype profile for the non-human animal subject by processing a data set comprising the genetic data and the phenotypic data to determine qualitative or quantitative measures of the at least one genomic locus of the plurality of genomic loci, and qualitative or quantitative measures of the at least one phenotype of the plurality of phenotypes;
(d) applying a machine learning prediction model to the genotype-phenotype profile of the non-human animal subject to identify the nutritional product recommended for the non-human subject, based at least in part, on a likelihood that the non-human animal subject has:
 (i) the first condition or a risk of developing the first condition; and
 (ii) the second condition or a risk of developing the second condition;
(e) ranking the first condition and the second condition based, at least in part, on severity of the first condition and the second condition to identify a highest ranking condition of the first condition and the second condition; and
(f) administering the nutritional product to the non-human animal subject, wherein the nutritional product:
 (i) comprises a food; and
 (ii) improves, ameliorates, or prevents at least the highest ranking condition or the risk of developing at least the highest ranking condition in the non-human animal subject.

2. The method of claim 1, wherein the first condition or the second condition comprises one or more genetic conditions, one or more nutritional conditions, one or more clinical conditions, one or more fitness conditions, one or more dermatological conditions, one or more allergy conditions, or any combination thereof.

3. The method of claim 1, wherein the non-human animal subject is a feline, a canine, or a farm animal.

4. The method of claim 3, wherein the non-human animal subject is a companion animal.

5. The method of claim 1, wherein the genetic data is determined by:
 (i) obtaining or having obtained a biological sample from the non-human animal subject; and
 (ii) performing or having performed a genotyping assay on the biological sample.

6. The method of claim 1, further comprising receiving the genetic data from a nucleic acid sequencing device, wherein the nucleic acid sequencing device comprises a whole genome sequencer, a skim sequencer, a quantitative PCR (qPCR) device, or a DNA microarray.

7. The method of claim 1, wherein the at least one genomic locus comprises one or more polymorphisms associated with the first condition.

8. The method of claim 1, further comprising receiving the phenotypic data from a guardian of the non-human animal subject, a veterinarian of the non-human animal subject, or a combination thereof.

9. The method of claim 1, wherein the plurality of phenotypes comprises any combination of weight, body mass index, sex, age, or breed of the non-human animal subject.

10. The method of claim 1, further comprising:
receiving activity data of the non-human animal subject;
updating the genotype-phenotype profile with the activity data to produce an updated profile; and
applying the machine learning prediction model to the updated profile.

11. The method of claim 10, wherein the activity data comprises activity level, activity type, calories burned, time asleep, or any combination thereof.

12. The method of claim 10, wherein the activity data comprises information obtained from an activity tracking device.

13. The method of claim 1, further comprising:
receiving environmental data of the non-human animal subject;
updating the genotype-phenotype profile with the environmental data to produce an updated profile; and
applying the machine learning prediction model to the updated profile.

14. The method of claim 13, wherein the environmental data comprise a city environment, a rural environment, geographic location of residence, presence of allergens, time spent inside/outside, frequency of stair use, or any combination thereof.

15. The method of claim 1, further comprising:
receiving biomarker data for the non-human animal subject, wherein the biomarker data comprises a presence or a level of one or more biomarkers detected in a biological sample obtained from the non-human animal subject, wherein the one or more biomarkers comprises a protein, a sugar, a lipid, a hormone, a vitamin, a cell, a metabolite, an electrolyte, a mineral, or any combination thereof;
updating the genotype-phenotype profile with the biomarker data to produce an updated profile; and
applying the machine learning prediction model to the updated profile.

16. The method of claim 1, wherein the machine learning prediction model comprises a clustering algorithm, a decision tree algorithm, a statistical algorithm, gradient boosted machine (GBM), or any combination thereof.

17. The method of claim 16, wherein the clustering algorithm is a centroid-based clustering algorithm.

18. The method of claim 16, wherein the machine learning prediction model is a genomic best linear unbiased prediction (GBLUP) or a Bayesian variable selection model.

19. The method of claim 1, further comprising validating the machine learning prediction model using samples from a validation cohort of non-human animal subjects of the same species that have the first condition or the second condition.

20. The method of claim 1, further comprising training the machine learning prediction model using samples from a training cohort of non-human animal subjects of the same species.

21. The method of claim 20, wherein the training data set comprises:
 (i) genetic data at a plurality of genomic loci of the training cohort, wherein at least one genomic locus of the plurality of genomic loci is associated with the first condition; and
 (ii) phenotypic data pertaining to a plurality of phenotypes of the training cohort of non-human animal subjects, wherein at least one phenotype of the plurality of phenotypes is associated with the second condition.

22. The method of claim 1, further comprising providing a notification to a guardian of the non-human animal subject or a veterinarian of the non-human animal subject, wherein the notification comprises:
 (i) the first condition or a risk of developing the first condition and the second condition or the risk of developing the second condition in the non-human animal subject;
 (ii) the genotype-phenotype profile of the non-human animal subject;

(iii) the nutritional product recommended for a non-human animal subject;
(iv) a recommendation for a behavioral modification for the non-human animal subject;
(v) a prescription of a therapeutic or prophylactic intervention for the non-human animal subject; or
(vi) any combination of (i) to (v).

23. The method of claim 22, wherein the behavioral modification comprises increasing, reducing, or avoiding one or more activities, wherein the one or more activities (i) increases or decreases the risk that the non-human animal subject will develop the first condition or the second condition, or (ii) worsens or improves the first condition or the second condition in the non-human animal subject.

24. The method of claim 23, wherein the one or more activities comprises:
(i) performance of a physical exercise;
(ii) ingestion of a type or quantity of the nutritional product, wherein the nutritional product further comprises feed, a supplement, a treat, or both;
(iii) exposure to a product;
(iv) usage of the product; or
(v) any combination of (i) to (iv).

25. The method of claim 1, further comprising:
performing (a) to (b) at a plurality of time points to obtain new genotype data or new phenotype data;
updating the genotype-phenotype profile with the new genotype data, the new phenotype data, or a combination thereof, at the plurality of time points to produce an updated profile; and
applying the machine learning prediction model to the updated profile.

26. The method of claim 25, further comprising providing a notification to a guardian of the non-human animal subject or a veterinarian of the non-human animal subject at one or more of the plurality of time points, wherein the notification comprises:
(i) the first condition or the risk of developing the first condition and the second condition or the risk of developing the second condition in the non-human animal subject;
(ii) the updated profile of the non-human animal subject;
(iii) a recommendation for a product, a behavioral modification, or any combination thereof, for the non-human animal subject;
(iv) a prescription of a therapeutic or prophylactic intervention for the non-human animal subject; or
(v) any combination of (i) to (iv).

27. The method of claim 1, further comprising:
receiving biomarker data, activity data, environment data, behavioral data, or clinical data for the non-human animal subject;
producing an updated genotype-phenotype profile for the non-human animal subject by processing the biomarker data, the activity data, the environment data, the behavioral data, or the clinical data, or the combination thereof, to determine quantitative or qualitative measures thereof; and
applying the machine learning prediction model to the updated genotype-phenotype profile of the non-human animal subject to identify:
a new nutritional product or a new amount of the nutritional product recommended for the non-human animal subject; or
a behavioral modification for the non-human animal subject.

28. The method of claim 27, wherein the clinical data comprises medical history of the non-human animal subject or medical history of a biological relative of the non-human animal subject.

29. The method of claim 27, wherein the behavioral data comprises chewing, itching, aggression, neurosis, anxiety, energy level, or any combination thereof.

30. The method of claim 1, wherein the nutritional product further comprises a food, supplement, treat, or both.

* * * * *